US007510863B2

(12) United States Patent
Samal et al.

(10) Patent No.: US 7,510,863 B2
(45) Date of Patent: Mar. 31, 2009

(54) AVIAN PNEUMOVIRUS GENES, RECOMBINANT AVIAN PNEUMOVIRUSES AND METHODS OF MAKING

(75) Inventors: Siba K. Samal, College Park, MD (US); Govindarajan Dhanasekaran, Silver Spring, MD (US)

(73) Assignee: University of Maryland, College Park, College Park, MD (US)

( * ) Notice: Subject to any disclaimer, the term of this patent is extended or adjusted under 35 U.S.C. 154(b) by 411 days.

(21) Appl. No.: 10/868,381

(22) Filed: Jun. 16, 2004

(65) Prior Publication Data

US 2005/0037479 A1 Feb. 17, 2005

Related U.S. Application Data

(63) Continuation-in-part of application No. PCT/US03/38123, filed on Dec. 2, 2003.

(60) Provisional application No. 60/430,301, filed on Dec. 2, 2002.

(51) Int. Cl.
*C12N 7/00* (2006.01)
*C12N 7/04* (2006.01)
*A61K 39/155* (2006.01)

(52) U.S. Cl. .................. 435/235.1; 435/236; 424/211.1

(58) Field of Classification Search ...................... 435/5, 435/6, 235.1; 424/199.1, 211.1, 204.1, 93.2, 424/209.1
See application file for complete search history.

(56) References Cited

U.S. PATENT DOCUMENTS

| 5,747,045 | A | 5/1998 | Ritchie et al. | |
|---|---|---|---|---|
| 6,605,283 | B1 | 8/2003 | Seal et al. | |
| 6,605,460 | B1 | 8/2003 | Goyal | |
| 2003/0232326 | A1* | 12/2003 | Fouchier et al. ................. | 435/5 |
| 2004/0005544 | A1* | 1/2004 | Fouchier et al. ................. | 435/5 |
| 2004/0005545 | A1* | 1/2004 | Fouchier et al. ................. | 435/5 |
| 2004/0258713 | A1* | 12/2004 | Mast et al. ............... | 424/199.1 |
| 2005/0287540 | A1* | 12/2005 | Murphy et al. ................. | 435/6 |

OTHER PUBLICATIONS

Fields et al., Third Edition, pp. 1187-1189 (1995).*
Gulati et al., "Protective Efficacy of high-passage avian pneumovirus (APV/MN/turkey/1-a/97) in Turkeys," Avian Diseases 45(3), pp. 593-597 (2001).*
Patnayak et al., "Experimental and field evaluation of a live vaccine against avian pneumovirus," Avian Pathology, 31, pp. 377-382 (2002).*
Van De Zande et al., "Duration of cross-protection between subtypes A and B avian pneumovirus in turkeys," Veterinary Record, 147 (5), pp. 132-134 (2000).*
Lwamba et al (CAB International 3(2): 107-117, 2002).*
Randhawa et al (Journal of Virology 71:9849-9854, 1997).*
Shin et al (Journal of Clinical Microbiology 40:1687-1693, May 2002).*
Peeters et al (Journal of Virology 73:5001-5009, 1999).*
Seal et al (Virus REsearch 66:139-147, 2000).*
Alexander, D.J., "Newcastle Disease and Other Avian *Paramyxoviridae* Infections," in *Diseases of Poultry*, 10th Edition, Calnek, B.W., et al., eds., Iowa State University Press, Ames, IA, pp. 541-569 (1997).
Alvarez, R., et al., "Nucleotide and Predicted Amino Acid Sequence-Based Analysis of the Avian Metapneumovirus Type C Cell Attachment Glycoprotein Gene: Phylogenetic Analysis and Molecular Epidemiology of U.S. Pneumoviruses," *J. Clin. Microbiol.* 41:1730-1735, American Society for Microbiology (Apr. 2003).
Anderson, L.J., et al., "Antigenic Characterization of Respiratory Syncytial Virus Strains with Monoclonal Antibodies," *J. Inf. Dis.* 151:626-633, University of Chicago Press (1985).
Aviv, H., and Leder, P., "Purification of Biologically Active Globin Messenger RNA by Chromatography on Oligothymidylic acid-Cellulose," *Proc. Natl. Acad. Sci. USA* 69:1408-1412, National Academy of Sciences (1972).
Baron, M.D., and Barrett, T., "Rescue of Rinderpest Virus from Cloned cDNA," *J. Virol.* 71:1265-1271, American Society for Microbiology (1997).
Bäyon-Auboyer, M.H., et al., "Comparison of the F-, G- and N-based RT-PCR protocols with conventional virological procedures for the detection and typing of turkey rhinotracheitis virus," *Arch. Virol.* 144:1091-1109, Springer-Verlag (1999).
Bäyon-Auboyer, M-H., et al., "Nucleotide sequences of the F, L and G protein genes of two non-A/non-B avian pneumoviruses (APV) reveal a novel APV subgroup," *J. Gen. Virol.* 81:2723-2733, Society for General Microbiology (2000).
Botstein, D., and Shortle, D., "Strategies and Applications of in Vitro Mutagenesis," *Science* 229:1193-1201, American Association for the Advancement of Science (1985).
Bowie, J.U., et al., "Deciphering the Message in Protein Sequences: Tolerance to Amino Acid Substitutions," *Science* 247:1306-1310, American Association for the Advancement of Science (1990).
Brutlag, D.L., et al., "Improved sensitivity of biological sequence database searches," *Comput. Appl. Biosci.* 6:237-245, Oxford University Press (1990).
Buys, S.B., and du Preez, J.H., "A preliminary report on the isolation of a virus causing sinusitis in turkeys in South Africa and attempts to attenuate the virus," *Turkeys* 28:36, 46, Fancy Fowl Publications Ltd. (1980).
Byrappa, S., et al., "A Highly Efficient Procedure for Site-specific Mutagenesis of Full-length Plasmids Using *Vent* DNA Polymerase," *Genome Res.* 5:404-407, Cold Spring Harbor Laboratory Press (1995).
Cavanagh, D., and Barrett, T., "Pneumovirus-like characteristics of the mRNA and proteins of turkey rhinotracheitis virus," *Virus Res.* 11:241-256, Elsevier (1988).

(Continued)

*Primary Examiner*—Mary E Mosher
(74) *Attorney, Agent, or Firm*—Sterne, Kessler, Goldstein & Fox P.L.L.C.

(57) ABSTRACT

The present invention is directed to novel avian pneumovirus strain Colorado (APV/CO) genes and intergenic sequences. Also disclosed are methods of making recombinant avian pneumovirus and live-attenuated APV/CO. Further disclosed are methods of diagnosing avian pneumovirus.

2 Claims, 17 Drawing Sheets

OTHER PUBLICATIONS

Chirgwin, J.M., et al., "Isolation of Biologically Active Ribonucleic Acid from Sources Enriched in Ribonuclease," *Biochemistry* 18:5294-5299, American Chemical Society (1979).

Chomczynski, P., and Sacchi, N., "Single-Step Method of RNA Isolation by Acid Guanidinium Thiocyanate-Phenol-Chloroform Extraction," *Anal. Biochem.* 162:156-159, Academic Press (1987).

Clarke, D.K., et al., "Rescue of Mumps Virus from cDNA," *J. Virol.* 74:4831-4838, American Society for Microbiology (2000).

Collins, P.L., et al., "Parainfluenza Viruses," in *Fields Virology, Third Edition*, Fields, B.N., et al., eds., Lippincott-Raven, Philadelphia, PA, pp. 1205-1241 (1996).

Collins, P.L., et al., "Production of infectious human respiratory syncytial virus from cloned cDNA confirms an essential role for the transcription elongation factor from the 5' proximal open reading frame of the M2 mRNA in gene expression and provides a capability for vaccine development," *Proc. Natl. Acad. Sci. USA* 92:11563-11567, National Academy of Sciences (1995).

Collins, P.L., et al., "The small hydrophobic protein of human respiratory syncytial virus: comparison between antigenic subgroups A and B," *J. Gen. Virol.* 71:1571-1576, Society for General Microbiology (1990).

Cook, J.K.A., "Avian rhinotracheitis," *Rev. Sci. Tech. Off. Int. Epiz.* 19:602-613, Office International des Épizooties (2000).

Cook, J.K.A., et al., "A Live Attenuated Turkey Rhinotracheitis Virus Vaccine. 1. Stability of the Attenuated Strain," *Avian Pathol.* 18:511-522, World Veterinary Poultry Association (1989).

Cook, J.K.A., et al., "Antigenic differentiation of strains of turkey rhinotracheitis virus using monoclonal antibodies," *Avian Pathol.* 22:257-273, World Veterinary Poultry Association (1993).

Cook, J.K.A., et al., "Preliminary antigenic characterization of an avian pneumovirus isolated from commercial turkeys in Colorado, USA," *Avian Pathol.* 28:607-617, Taylor & Francis (1999).

Dar, A.M., et al., "Sequence analysis of the nucleocapsid and phosphoprotein genes of avian pneumoviruses circulating in the US," *Virus Res.* 79:15-25, Elsevier (Nov. 2001).

Easton, A.J., and Chambers, P., "Nucleotide sequence of the genes encoding the matrix and small hydrophobic proteins of pneumonia virus of mice," *Virus Res.* 48:27-33, Elsevier (1997).

Fujita, T., et al., "Interferon-β Gene Regulation: Tandemly Repeated Sequences of a Synthetic 6 bp Oligomer Function As a Virus-Inducible Enhancer," *Cell* 49:357-367, Cell Press (1987).

Garcin, D., et al., "A highly recombinogenic system for the recovery of infectious Sendai paramyxovirus from cDNA: generation of a novel copy-back nondefective interfering virus," *EMBO J.* 14:6087-6094, Oxford University Press (1995).

Gassen, U., et al., "Establishment of a Rescue System for Canine Distemper Virus," *J. Virol.* 74:10737-10744, American Society for Microbiology (2000).

Goyal, S.M., "Vaccination against avian pneumovirus," *North Central Avian Disease Conference and Symposium on Emerging Respiratory Diseases*, Minneapolis, MN, p. 51 (Oct. 1999).

Gulati, B.R., et al., "Development of a Highly Sensitive and Specific Enzyme-Linked Immunosorbent Assay Based on Recombinant Matrix Protein for Detection of Avian Pneumovirus Antibodies," *J. Clin. Microbiol.* 38:4010-4014, American Society for Microbiology (2000).

Harada, H., et al., "Absence of the Type I IFN System in EC Cells: Transcriptional Activator (IRF-1) and Repressor (IRF-2) Genes Are Developmentally Regulated," *Cell* 63:303-312, Cell Press (1990).

Hoffman, M.A., and Banerjee, A.K., "An Infectious Clone of Human Parainfluenza Virus Type 3," *J. Virol* 71:4272-4277, American Society for Microbiology (1997).

Huang, Z., et al., "High-level expression of a foreign gene from the most 3'-proximal locus of a recombinant Newcastle disease virus," *J. Gen. Virol.* 82:1729-1736, Society for General Microbiology (Jul. 2001).

Jalkanen, M., et al., "Cell Surface Proteoglycan of Mouse Mammary Epithelial Cells is Shed by Cleavage of its Matrix-binding Ectodomain from its Membrane-associated Domain," *J. Cell. Biol.* 105:3087-3096, Rockefeller University Press (1987).

Jalkanen, M., et al., "Heparan Sulfate Proteoglycans from Mouse Mammary Epithelial Cells: Localization on the Cell Surface with a Monoclonal Antibody," *J. Cell. Biol.* 101:976-985, Rockefeller University Press (1985).

Johnson, P.R., et al., "The G glycoprotein of human respiratory syncytial viruses of subgroups A and B: Extensive sequence divergence between antigenically related proteins," *Proc. Natl. Acad. Sci. USA* 84:5625-5629, National Academy of Sciences (1987).

Jones, R.C., et al., "Demonstration of a candidate virus for turkey rhinotracheitis in experimentally inoculated turkeys," *Vet. Rec.* 119:599-600, British Veterinary Association (1986).

Juhasz, K., and Easton, A.J., "Extensive sequence variation in the attachments (G) protein gene of avian pneumovirus: evidence for two distinct subgroups," *J. Gen. Virol.* 75:2873-2880, Society for General Microbiology (1994).

Kleven, S.H., et al., "Report of the Committee on Transmissible Diseases of Poultry and Other Avian Species," in *Proceedings of the 101st Annual Meeting of the U.S. Animal Health Association*, Pat Campbell and Associates and Spectrum Press, Richmond, VA, pp. 473-519 (1997).

Krishnamurthy, S., and Samal, S.K., "Nucleotide sequences of the trailer, nucleocapsid protein gene and intergenic regions of Newcastle disease virus strain Beaudette C and completion of the entire genome sequence," *J. Gen. Virol.* 79:2419-2424, Society for General Microbiology (1998).

Ling, R., et al., "Sequence analysis of the 22K, SH and G genes of turkey rhinotracheitis virus and their intergenic regions reveals a gene order different from that of other pneumoviruses," *J. Gen. Virol.* 73:1709-1715, Society for General Microbiology (1992).

Lwamba, H.C.M., et al., "Antigenic Cross-Reactivity Among Avian Pneumoviruses of Subgroups A, B, and C at the Matrix but not Nucleocapsid Proteins," *Avian Dis.* 46:725-729, American Association of Avian Pathologists (Jul.-Sep. 2002).

Makino, R., et al., "Evaluation of Quantitative Detection of mRNA by the Reverse Transcription-Polymerase Chain Reaction," *Technique* 2:295-301, W.B. Saunders Co. (1990).

Mallipeddi, S.K., and Samal, S.K., "Sequence variability of the glycoprotein gene of bovine respiratory syncytial virus," *J. Gen. Virol.* 74:2001-2004, Society for General Micriobiology (1993).

McDougall, J.S., and Cook, J.K.A., "Turkey rhinotracheitis: Preliminary investigations," *Vet. Rec.* 118:206-207, British Veterinary Association (1986).

Nagai, Y., et al., "Proteolytic Cleavage of the Viral Glycoproteins and Its Significance for the Virulence of Newcastle Disease Virus," *Virol.* 72:494-508, Academic Press (1976).

Njenga, M.K., et al., "Metapneumoviruses in birds and humans," *Virus Res.* 91:163-169, Elsevier (Feb. 2003).

O'Loan, C.J., et al., "An improved ELISA and serum neutralisation test for the detection of turkey rhinotracheitis virus antibodies," *J. Virol. Meth.* 25:271-282, Elsevier (1989).

Panigrahy, B., et al., "Experimental and Serologic Observations on Avian Pneumovirus (APV/turkey/Colorado/97) Infection in Turkeys," *Avian Dis.* 44:17-22, American Association of Avian Pathologists (2000).

Peeters, B.P.H., et al., "Rescue of Newcastle Disease Virus from Cloned cDNA: Evidence that Cleavability of the Fusion Protein is a Major Determinant for Virulence," *J. Virol.* 73:5001-5009, American Society for Microbiology (1999).

Pringle, C.R., "The universal system of virus taxonomy of the International Committee on Virus Taxonomy (ICTV), including new proposals ratified since publication of the Sixth ICTV Report in 1995," *Arch. Virol.* 143:203-210, Springer-Verlag (1998).

Pringle, C.R., "Virus Taxonomy—San Diego 1998," *Arch. Virol.* 143:1449-1459, Springer-Verlag (1998).

Radecke, F., et al., "Rescue of measles viruses from cloned DNA," *EMBO J.* 14:5773-5784, Oxford Unviversity Press (1995).

Randhawa, J.S., et al., "Rescue of Synthetic Minireplicons Establishes the Absence of the NS1 and NS2 Genes from Avian Pneumovirus," *J. Virol.* 71:9849-9854, American Society for Microbiology (1997).

Samal, S.K., and Zamora, M., "Nucleotide sequence analysis of a matrix and small hydrophobic protein dicistronic mRNA of bovine respiratory syncytial virus demonstrates extensive sequence divergence of the small hydrophobic protein from that of human respiratory syncytial virus," *J. Gen. Virol.* 72:1715-1720, Society for General Micriobiology (1991).

Seal, B.S., "Avian pneumoviruses and emergence of a new type in the United States of America," *Anim. Health Res. Rev. 1*:67-72, CAB International (2000).

Seal, B.S., "Matrix protein gene nucleotide and predicted amino acid sequence demonstrate that the first US avian pneumovirus isolate is distinct from European strains," *Virus Res. 58*:45-52, Elsevier (1998).

Seal, B.S., et al., "Fusion protein predicted amino acid sequence of the first US avian pneumovirus isolate and lack of heterogeneity among other US isolates," *Virus Res. 66*:139-147, Elsevier (2000).

Shin, H-J., et al., "Molecular Epidemiology of Subgroup C Avian Pneumoviruses Isolated in the United States and Comparison with Subgroup A and B Viruses," *J. Clin. Micriobiol. 40*:1687-1693, American Society for Microbiology (May 2002).

Toquin, D., et al., "Lack of Antigenic Relationship Between French and Recent North American Non-A/Non-B Turkey Rhinotracheitis Viruses," *Avian Dis. 44*977-982, American Association of Avian Pathologists (2000).

Toquin, D., et al., "Subgroup C avian metapneumovirus (MPV) and the recently isolated human MPV exhibit a common organization but have extensive sequence divergence in their putative SH and G genes," *J. Gen. Virol. 84*:2169-2178, Society For General Microbiology (Aug. 2003).

van den Hoogen, B.G., et al., "A newly discovered human pneumovirus isolated from young children with respiratory tract disease," *Nat. Med. 7*:719-724, Nature Publishing Group (Jun. 2001).

van den Hoogen, B.G., et al., "Analysis of the Genomic Sequence of a Human Metapneumovirus," *Virology 295*:119-132, Elsevier (Mar. 2002).

Whelan, S.P.J., et al., "Efficient recovery of infectious vesicular stomatitis virus entirely from cDNA clones," *Proc. Natl. Acad. Sci. USA 92*:8388-8392, National Academy of Sciences (1995).

Wilding, G.P., et al., "Ciliostatic agent found in rhinotracheitis," *Vet. Rec. 118*:735, British Veterinary Association (1986).

Wilson, I.A., et al., "The Structure of an Antigenic Determinant in a Protein," *Cell 37*:767-778, MIT (1984).

Yunus, A.S., et al., "Deduced amino acid sequence of the small hydrophobic protein of US avian pneumovirus has greater identity with that of human metapneumovirus than those of non-US avian pneumoviruses," *Virus Res. 93*:91-97, Elsevier (May 2003).

Yunus, A.S., et al., "Rescue of Bovine Respiratory Syncytial Virus from Cloned cDNA: Entire Genome Sequence of BRSV Strain A51908," *Virus Genes 23*:157-164, Kluwer Academic Publishers (Oct. 2001).

Zoller, M.J., and Smith, M., "Oligonucleotide-Directed Mutagenesis: A Simple Method Using Two Oligonucleotide Primers and a Single-Stranded DNA Template," *DNA 3*:479-488, Mary Ann Liebert, Inc. (1984).

International Search Report for International Patent Application No. PCT/US03/38123, mailed Aug. 23, 2004, ISA/US, Alexandria, VA.

NCBI Entrez, GenBank Report, Accession No. AF176592, 1999.

NCBI Entrez, GenBank Report, Accession No. AF187152 (replaced by Accession No. AY579780), 2000.

NCBI Entrez, GenBank Report, Accession No. AY579780 (replaced Accession No. AF187152), 2004.

NCBI Entrez, GenBank Report, Accession No. AF262571, 2000.

NCBI Entrez, GenBank Report, Accession No. CAD42709, 2002.

* cited by examiner

A

```
              10        20        30        40   N gene
APV-CO   : 3' UGCUCUUUUUGCGUAUAUUCUGUGUUGAAGGUUGUUUG-CCCUGUUCA    SEQ ID NO: 1
APV-A 3...M gene...UCGAACUAUAUAAUAAAUCUUUUUUAACUUUUUUAACCCUGUUCACUUUUACAGAACC...F gene... (SEQ ID NO 4)
          M-GE                    (M-F IGS)              F-GS ..UCAAUGAUUUUUUAACCCUGUUCAGGUUCUACAGCG......M2 gene... (SEQ ID NO 5)
  F-GE        (F-M2 IGS)    M2-GS ..UCAAUUAUUUUUUAACCCUGUUCAGUUGUACCUC........SH gene... (SEQ ID NO 6)
  M2-GE        (M2-SH IGS)    SH-GS ..UCAAUAAAUUUUUAGUACUAAUUUUGCUAGUCUCCUCCUUUUGCCCUGUUCAGUUGUAC...G gene...5' (SEQ ID NO 7)
  SH-GE              (SH-G IGS)                        G-GS
GUGCUCUGUCCACUAGGUUACUAAUUUUUGCUAGUCUCCUCCUUUUGCCCUGGUUCUUUUGGUU

FIG.3

Gene Start
5' GGGACAAGTCAACATGGAGCCCCTGAAAGTCTCTGGAAGTGGAGGGATACCGATGAAGACA 61
             M  E  P  L  K  V  S  G  S  G  G  I  P  M  K  T  16

AGGCTTAATATCATACTTGAGAAGTCAATCAATAAAATCTTGATCATTTTAGGATTACTA 121
 R  L  N  I  I  L  E  K  S  I  N  K  I  L  I  I  L  G  L  L  36

TTAACTGCCTCAACTGTAATTACAATCACACTCACAGTGGAGTATATAAGAGTAGAAAAT 181
 L  T  A  S  T  V  I  T  I  T  L  T  V  E  Y  I  R  V  E  N  56

GTAATTGCAACTTTGCCAAAGATGGAAGCAGAGGTGGCCAAGTACAACTCCGGAACCACC 241
 V  I  A  T  L  P  K  M  E  A  E  V  A  K  Y  N  S  G  T  T  76

AACACAGCCAACGAAGACAACTCCTACACTAACCAGAACCAGATCAACGCACCGCATCCC 301
 N  T  A  N  E  D  N  S  Y  T  N  Q  N  Q  I  N  A  P  H  P  96

TCAAAACCAGACTCAGTTTCAAGGACCACTCATCCCCACCACTCATCCTACTAACCCATCTCTACCT 361
 S  K  P  D  S  V  S  R  R  T  T  H  P  T  N  P  S  C  W  R  E  116

GAGAAAAAGTGCCAGAATATCACAGCTAAATGGTCCAATTGTTTTGGCACATCTCTACCT 421
 E  K  K  C  Q  N  I  T  A  K  W  S  N  C  F  G  T  S  L  P  136

GTGAGGGTGAACTGCACGGTACTAAGAGAATTGTGTGATGAGCAGCCAGGCAATCACACA 481
 V  R  V  N  C  T  V  L  R  E  L  C  D  E  Q  P  G  N  H  T  156

ACAGTTCAAGTATCAAGGAGGTGTACTAGCCATATATGCATTAAATTGGGATTGTAGTTAT 541
 T  V  Q  V  S  R  R  C  T  C  I  Y  A  L  N  W  D  C  S  Y  176

GCTTGAGAGAGAACTACACTAGCCGACCCTAATGAGGTCCACAAAAAAGATTAAAAGC 601
 A  *  (SEQ ID NO 9)                                        177

Gene End
ATAAACCAATTTTTT*AGTTATTT*AAAA 3' (SEQ ID NO 8)               628

FIG.4

Gene Start
GGGACAAGTCAACATGGAGCCCTGAAGTCTCTGGAAGTGGAGGATACCGATGAAGACA 61
                M   E   P   L   K   V   S   G   S   G   G   I   P   M   K   T  16
AGGCTTAATATCATACTTGAGAGTCAATCAATAAAATCTTGATCATTTTAGGATTACTA 121
 R   L   N   I   L   E   K   S   I   N   *K*  *I*  *L*  *I*  *L*  *G*  *L*  *L*  36
TTAACTGCCTCAACTGTAATTACAATCACACTCACAGTGGAGTATATAAGAGTAGAAAAT 181
*L*  *T*  *A*  *S*  *T*  *V*  *I*  *T*  *I*  *T*  *L*  *T*  *V*  *E*  *Y*  *I*  *R*  *V*  *E*  N  56
GAATTGCAACTTGCAAGATGGAAGCAGAGGTGGCAAGAACTCCGAACCACCAACA 241
 E   L   Q   L   C   K   M   E   A   E   V   A   K   T   T   P   E   P   P   T  76
CAGCCAACGAGAACAACTCCTACACTAACCAGATCAACCACCGCATCCCTCAAA 301
 Q   P   T   K   T   P   T   L   T   R   T   R   S   T   T   A   S   L   K  96
ACCAGACCAGTTCAAGGACCACTCACATCCCACCAGTGCTGGAGAGGAGGAA 361
 T   R   P   V   S   R   T   T   H   P   T   N   P   S   C   W   R   E   E   E  116
AAGTGCCAGAATATCACAGCTAAAGTGTCCAATTGTTTGGCACATCTCTACTGTGTGAGG 421
 K   C   Q   *N*  *I*  *T*   A   K   W   S   N   C   F   G   T   S   L   P   V   R  136
GTGAACTGCAGGTACTAAGAGAGCTGTGTGATGAGCAATCACACAACAGTT 481
 V   *N*  *C*  T   V   L   R   E   L   C   D   E   Q   P   G   *N*  *H*  *T*  *T*  V  156
CAAGTATCAAGGAGGTGTACATGCATTAAATTGGGATTGTAGTTATGCTTGA 541
 Q   V   S   R   *R*  *C*  *T*  *C*  I   Y   A   L   N   W   D   C   S   Y   A  (SEQ ID NO: 88) 176
GAGAGAGACTACACTAGCCGACCCTAATGAGGTCCACAGAAAAGATTAAAGCATAAAC 601
Gene End
CAATTTTTAGTTATTTAAAAA 3'   (SEQ ID NO: 87) 622

FIG. 4a

```
APV/CO  MEPLKVSGSGGIP-MKTRLNIILEKSINKILILGLLLTASTVITITLTVEYIRVENVIA      59
HMPV    .IT.D.IK.D.SSKTC.H.KK.IKDHSG.V..V.K.I.ALL.FL.V.I.IN..K...NLQ    60
APV/A   ---MTSTVNL.SD-TASKRTV.KSRCNSCCR.LVSCVAVICAILALIFL.AT.GLSVKL.    56
APV/B   ---MTSTVNL.SS-TSSRWT.AKSQCMLCLRTMMNCAVVICA.LVLIFL.AT.GLSVKL.    56
HRSV    ------------------------MENTS.TIEFSSKFWPYF.LIHMITT.IS---LL      31
BRSV    ------------------------MNNTST.IEFTGEFW.YF.LAFMMLT.GF---FF      31
PVM     ---------------------MDPNMTSHQ.T.EINMTSSRIG.H.TPAPTAPL----      33

APV/CO  TLPKMEAEVAKYNSGTTNTANEDNSYTNQNQINAPHPSKPDSVSRTTHPTNPSCWREEKK    119
HMPV    ICQSKTESDK.DS.--S..TSVTTKT.LNHD.TQYFK.LIQRYTNSAINSDTCWKINRNQ    118
APV/A   FTVQEVHNCKQKL.GAST.TAAIYTTPSTMIEALQTNQLKLTTNERRSTPP-D.LV.K.L    115
APV/B   VTI.ERNTCQLRL.ELST.TAPILRS...PYLGGSTSTPKLTTVTSITDLTHQ.PQRKEL    116
HRSV    IIIS---------------IMIAILN---------------------------.L        44
BRSV    IVTS---------------LVAAILN---------------------------.L        44
PVM     -------------------L.CAVIN---------------------------TV        42

APV/CO  CQNITAKWSN--CFGTSLPVRVNCTVLRELCDEQPGNHTTVQVSRRCTCIYALNWDCSYA    177
HMPV    .T..TTYKFL-...KSEDTKTN..DK.TD..RNK.KPAVG.YHIVE.H...TVK.K.YHY    176
APV/A   .EGEVRYLKTKG.LGAREGEDL..ID.VVE.VGK.CG.NEDYKECI..NNGTATKC.YN-    174
APV/B   .NGTITYINSDG.LDEKEGESID.IE.IAR.V.TLCDPNPNYNHCM..KNSTGL.C.YN-    175
HRSV    .EYNVFHNKT---FELP-RA..:-----------------------------            64
BRSV    .DFNDHHTNS---LDIRTRL.ND-.Q.ITRAH.GSI.QSSN----------            81
PVM     .ALIMACSSR------STATSGIVSSQ.TVH.NHPPPSYG-VNV.GLPGNLYSRNTT      92

APV/CO  -----           (SEQ ID No.9)
HMPV    PTDETQ 182      (SEQ ID No.10)
APV/A   -----           (SEQ ID No.11)
APV/B   -----           (SEQ ID No.12)
HRSV    -----           (SEQ ID No.13)
BRSV    -----           (SEQ ID No.14)
PVM     -----           (SEQ ID No.15)
        *
```

FIG. 6

```
APV/CO   MEPLKVSGSSGGIP-MKTRINIILEKSINKILILGLLLTASTVITITLTVEYIRVENELQ    59
HMPV     .IT.D.IK.D.SSKTC.H.KK.IKDHSG.V..V.K.I.ALL.FL.V.I.IN..K...N..     60
APV/A    ---MTSTVNL.SD-TASKRTV.KSRCNSCCR.LVSCVAVICAILALIFL.AT.GLSVK.A    56
APV/B    ---MTSTVNL.SS-TSS.WT.AKSQCMLCLRTMMNCAVVICA.LVLIFL.AT.GLSVK.A    56
HRSV     ------------------------MENTS.TIEFSSKFWPYF.LIHMITT.IS----.L    31
BRSV     -------------------------M.NTST.IEFTGEFW.YF.LAFMMLT.GF----FF    31
PVM      --------------MDPNMTSHQ.T.EINM.S.RIG.H.TPAPTAPL-----.A          35

APV/CO   LCKMEAEVAKTTPEPPTQPTKTTPTLTRTRSTTASL

```
                 ┌─── p (+) APV ───┐
                 │N│P│M│F│M2│SH│G│  L  │
                         ╲╲__╱╱
```

Wild type........AGA AAA GCC CGG.......(SEQ ID NO 44)
         Arg Lys Ala Arg        (SEQ ID NO 21)

F-Mutant.........* CAG GGA *.......(SEQ ID NO 45)
         Arg Gln Gly Arg        (SEQ ID NO 20)

FIG.9

```
           |<-- Intra-cellular domain -->|<-- Transmembrane domain -->|<-- Extra-cellular domain ......
APV-CO  MEVKVENVGKSQELKVKVKNFIKRSDCKKKLFALILGLVSFELTMNIMLSVMYVESNEALSLCRIQGTPAPRDNKTNTENATKETTLHTT   90
Mn-1a   ..........................................................................................   90
Mn-2a   ..........................................................................................   90

APV-CO  TTTRDPEVRETKTTKPQANEGATNPSRNLTTKGDKHQTTRATTEAELEKQSKQTTEPGTSTQKHTPTRPSSKSPTTTQAIAQLTTPTTPK  180
Mn-1a   ..........................................................................................  180
Mn-2a   ..................................................................A............T..P....A..  180

APV-CO  ASTAPKNRQATTKKTETDTTTASRARNTNNPTETATTTPKATTETGKSKEGPTQHTTKEQPETTAGETTTPQPRRTASRPAPTTKIEEEA  270
Mn-1a   ............................DS..G...A....AA.A................GA.....A.....................  270
Mn-2a   ...............................................G.................R........................  270

APV-CO  ETTKTRTTKSTQTSTGPPRPTGGAPSGAATEGSGRAAAAGGPSAASAGGRRRTEAAAERDRRTRAGAGPTAGGARARTAAASERGADTAG  360
Mn-1a   ..........................................................................................  360
Mn-2a   .........N...........RST..KT...NNK.TTTTKR.NT..TDS.QQ.RIT..Q.QQ.QTR.K..TN..HPQ.TTTP.HNT..TN  360

APV-CO  SAGGGPGGDGATGGLSGGAPAEREDASGGTAAAGPGDGTEADGRAPPAAALAGRTTESAAGAAGDSGRAGTAGWGSAADGRSTGGNAAAE  450
Mn-1a   .......................G..................................................................  450
Mn-2a   .TK.S.KE.KT.RDP.SKT.T.Q....K.....N..GSA...R.....TTPT.........TT..DSG.E.TRRR....R.....ST...  450

APV-CO  AGAAQSGRAAPRQPSGGTAPESTAPPNSGGSGRADAAPTEEVGVGSGLWRGRYVCGPCGESVPEHPMNPCFGDGTAWICSDDGGSLPAGC  540
Mn-1a   ..........................................................................................  540
Mn-2a   ..T......T.K.......AGN.....NES........A.......SI..........R...L..................G..N.....  540

APV-CO  YDGGTDGVVCCGVCGGNSCCCGRVECTCGGGAGLLSCCCGSYSWS       585 (SEQ ID NO:56)
Mn-1a   .............................................       585 (SEQ ID NO:57)
Mn-2a   ..S.A.......I.............................N..       585 (SEQ ID NO:58)
```

```
                    1                LEADER (40nt)              40
                    5' acgagaaaaaaacgcatataagcaactcccaaacaaaac (SEQ ID NO:24)

gene end            intergenic          gene start
                                                  41
                                                  GGGACAAGTgAA-AATGtctct (SEQ ID NO:59)
                          1246
(SEQ ID NO:60) ttatgAGTaAtTaAAAAA-       c
                                                  1248
                                                  GGGACAAGTcAA-AATGtcctt (SEQ ID NO:61)
                          2156
(SEQ ID NO:62) tatgTAGTTAaTaAAAAA-       c
                                                  2158
                                                  GGGACAAGTggA-AATGgagtc (SEQ ID NO:63)
                          3025
(SEQ ID NO:64) gataTtaTTttagaAAAAA-      tt
                                                  3028
                                                  GGGACAAGTgAA-AATGtcttg (SEQ ID NO:65)
                          4671
(SEQ ID NO:66) atttTAGTTAcTaAAAAA-       tt
                                                  4674
                                                  GGGACAAGTgAA-gATGtctcg (SEQ ID NO:67)
                          5421
(SEQ ID NO:68) ttctaAGTTAaTaAAAAA-       tt
                                                  5424
                                                  GGGACAAGTcAA-cATGgagcc (SEQ ID NO:69)
                          6046
(SEQ ID NO:70) ttttTAGTTATtTtAAAAA-   tcatg - 81 nt - aaaac  GGGACAAGTcAA-cATGgaggt (SEQ ID NO:72)
                                       (SEQ ID NO:71)       6138
                          7935
(SEQ ID NO:73) aagtTAGTTAaTtAAAAA-       gaa
                                                  7939
                                                  GGaCAAGTtAAaAATGgatcc (SEQ ID NO:74)
                          14111
(SEQ ID NO:75) caatTAGTTAtTtAAAAA Consensus  TAGTTAnTnAAAAA (SEQ ID NO:76)              GGGACAAGTnAAnATG (SEQ ID NO:77)

14112     TRAILER (39 nt)     14150
                 tgaggaactaaaattggatgaatacggtttttttgccgt 3' (SEQ ID NO:78)
```

Fig. 13

SEQUENCE LISTING

```
<160> NUMBER OF SEQ ID NOS: 101

<210> SEQ ID NO 1
<211> LENGTH: 49
<212> TYPE: RNA
<213> ORGANISM: Avian pneumovirus

<400> SEQUENCE: 1
ugcucuuuuu uugcguauau ucuguugaag guuuguuuug cccuguuca          49

<210> SEQ ID NO 2
<211> LENGTH: 50
<212> TYPE: RNA
<213> ORGANISM: Avian pneumovirus

<400> SEQUENCE: 2
ugcucuuuuu uugcguaagu ucguccaaga ucuuuuauu acccuguuca           50

<210> SEQ ID NO 3
<211> LENGTH: 35
<212> TYPE: RNA
<213> ORGANISM: Avian pneumovirus

<400> SEQUENCE: 3
cauauuuaau cuaagguuuu uuuauacccu guuca                         35

<210> SEQ ID NO 4
<211> LENGTH: 47
<212> TYPE: RNA
<213> ORGANISM: Avian pneumovirus

<400> SEQUENCE: 4
ucgaacuaua auaaaucuuu uuuaacccug uucacuuuua cagaacc             47

<210> SEQ ID NO 5
<211> LENGTH: 36
<212> TYPE: RNA
<213> ORGANISM: Avian pneumovirus

<400> SEQUENCE: 5
ucaaugauuu uuuaacccug uucagguucu acagcg                        36

<210> SEQ ID NO 6
<211> LENGTH: 35
<212> TYPE: RNA
<213> ORGANISM: Avian pneumovirus

<400> SEQUENCE: 6
ucaauuauuu uuuuaacccu guucaguugu accuc                         35

<210> SEQ ID NO 7
<211> LENGTH: 120
<212> TYPE: RNA
<213> ORGANISM: Avian pneumovirus
```

<400> SEQUENCE: 7
ucaauaaauu uuuaguacuu auacagaccu gucacgguuc cgguucuuuu ugguugugcu    60
cuuguccacu agguuacuaa uuuuugcuag ucucuuccuu uuugcccugu cauguugac    120

<210> SEQ ID NO 8
<211> LENGTH: 629
<212> TYPE: DNA
<213> ORGANISM: Avian pneumovirus
<220> FEATURE:
<221> NAME/KEY: CDS
<222> LOCATION: (14)..(547)

<400> SEQUENCE: 8

```
gggacaagtc aac atg gag ccc ctg aaa gtc tct gga agt gga ggg ata      49
            Met Glu Pro Leu Lys Val Ser Gly Ser Gly Gly Ile
            1               5                  10 ccg atg aag aca agg ctt aat atc ata ctt gag aag tca atc aat aaa     97
Pro Met Lys Thr Arg Leu Asn Ile Ile Leu Glu Lys Ser Ile Asn Lys
         15                  20                  25 atc ttg atc att tta gga tta cta tta act gcc tca act gta att aca    145
Ile Leu Ile Ile Leu Gly Leu Leu Leu Thr Ala Ser Thr Val Ile Thr
     30                  35                  40 atc aca ctc aca gtg gag tat ata aga gta gaa aat gta att gca act    193
Ile Thr Leu Thr Val Glu Tyr Ile Arg Val Glu Asn Val Ile Ala Thr
 45                  50                  55                  60 ttg cca aag atg gaa gca gag gtg gcc aag tac aac tcc gga acc acc    241
Leu Pro Lys Met Glu Ala Glu Val Ala Lys Tyr Asn Ser Gly Thr Thr
                 65                  70                  75 aac aca gcc aac gaa gac aac tcc tac act aac cag aac cag atc aac    289
Asn Thr Ala Asn Glu Asp Asn Ser Tyr Thr Asn Gln Asn Gln Ile Asn
             80                  85                  90 gca ccg cat ccc tca aaa cca gac tca gtt tca agg acc act cat ccc    337
Ala Pro His Pro Ser Lys Pro Asp Ser Val Ser Arg Thr Thr His Pro
         95                 100                 105 acc aat ccc agc tgc tgg aga gag gag aaa aag tgc cag aat atc aca    385
Thr Asn Pro Ser Cys Trp Arg Glu Glu Lys Lys Cys Gln Asn Ile Thr
     110                 115                 120 gct aaa tgg tcc aat tgt ttt ggc aca tct cta cct gtg agg gtg aac    433
Ala Lys Trp Ser Asn Cys Phe Gly Thr Ser Leu Pro Val Arg Val Asn
 125                 130                 135                 140 tgc acg gta cta aga gaa ttg tgt gat gag cag cca ggc aat cac aca    481
Cys Thr Val Leu Arg Glu Leu Cys Asp Glu Gln Pro Gly Asn His Thr
                 145                 150                 155 aca gtt caa gta tca agg agg tgt aca tgc ata tat gca tta aat tgg    529
Thr Val Gln Val Ser Arg Arg Cys Thr Cys Ile Tyr Ala Leu Asn Trp
             160                 165                 170 gat tgt agt tat gct tga gagagagact acactagccg accctaatga            577
Asp Cys Ser Tyr Ala
         175 ggtccacaaa aaaagattaa aagcataaac caatttttta gttatttaaa aa           629
```

<210> SEQ ID NO 9
<211> LENGTH: 177
<212> TYPE: PRT
<213> ORGANISM: Avian pneumovirus

<400> SEQUENCE: 9

Met Glu Pro Leu Lys Val Ser Gly Ser Gly Gly Ile Pro Met Lys Thr
1               5                  10                  15

```
Arg Leu Asn Ile Ile Leu Glu Lys Ser Ile Asn Lys Ile Leu Ile Ile
             20                  25                  30

Leu Gly Leu Leu Leu Thr Ala Ser Thr Val Ile Thr Ile Thr Leu Thr
         35                  40                  45

Val Glu Tyr Ile Arg Val Glu Asn Val Ile Ala Thr Leu Pro Lys Met
 50                  55                  60

Glu Ala Glu Val Ala Lys Tyr Asn Ser Gly Thr Thr Asn Thr Ala Asn
 65                  70                  75                  80

Glu Asp Asn Ser Tyr Thr Asn Gln Asn Gln Ile Asn Ala Pro His Pro
                 85                  90                  95

Ser Lys Pro Asp Ser Val Ser Arg Thr Thr His Pro Thr Asn Pro Ser
            100                 105                 110

Cys Trp Arg Glu Glu Lys Lys Cys Gln Asn Ile Thr Ala Lys Trp Ser
            115                 120                 125

Asn Cys Phe Gly Thr Ser Leu Pro Val Arg Val Asn Cys Thr Val Leu
    130                 135                 140

Arg Glu Leu Cys Asp Glu Gln Pro Gly Asn His Thr Thr Val Gln Val
145                 150                 155                 160

Ser Arg Arg Cys Thr Cys Ile Tyr Ala Leu Asn Trp Asp Cys Ser Tyr
                165                 170                 175

Ala

<210> SEQ ID NO 10
<211> LENGTH: 134
<212> TYPE: PRT
<213> ORGANISM: Human metapneumovirus

<400> SEQUENCE: 10

Ile Thr Asp Ile Lys Asp Ser Ser Lys Thr Cys His Lys Leu Ile Lys
 1               5                  10                  15

Asp His Ser Gly Val Val Lys Ile Ala Leu Leu Phe Leu Val Ile Ile
             20                  25                  30

Asn Lys Asn Leu Gln Ile Cys Gln Ser Lys Thr Glu Ser Asp Lys Asp
         35                  40                  45

Ser Ser Thr Ser Val Thr Thr Lys Thr Leu Asn His Asp Thr Gln Tyr
 50                  55                  60

Phe Lys Leu Ile Gln Arg Tyr Thr Asn Ser Ala Ile Asn Ser Asp Thr
 65                  70                  75                  80

Cys Trp Lys Ile Asn Arg Asn Gln Thr Thr Thr Tyr Lys Phe Leu Lys
                 85                  90                  95

Ser Glu Asp Thr Lys Thr Asn Asp Lys Thr Asp Arg Asn Lys Lys Pro
            100                 105                 110

Ala Val Gly Tyr His Ile Val Glu His Thr Val Lys Lys Tyr His Tyr
            115                 120                 125

Pro Thr Asp Glu Thr Gln
    130

<210> SEQ ID NO 11
<211> LENGTH: 152
<212> TYPE: PRT
<213> ORGANISM: Avian pneumovirus

<400> SEQUENCE: 11

Met Thr Ser Thr Val Asn Leu Ser Asp Thr Ala Ser Lys Arg Thr Val
 1               5                  10                  15

Lys Ser Arg Cys Asn Ser Cys Cys Arg Leu Val Ser Cys Val Ala Val
```

```
                 20                  25                  30
Ile Cys Ala Ile Leu Ala Leu Ile Phe Leu Ala Thr Gly Leu Ser Val
             35                  40                  45

Lys Leu Phe Thr Val Gln Glu Val His Asn Cys Lys Gln Lys Leu Gly
 50                  55                  60

Ala Ser Thr Thr Ala Ala Ile Tyr Thr Thr Pro Ser Thr Met Ile Glu
65                  70                  75                  80

Ala Leu Gln Thr Asn Gln Leu Lys Leu Thr Thr Asn Glu Arg Arg Ser
                 85                  90                  95

Thr Pro Pro Asp Leu Val Lys Leu Glu Gly Glu Val Arg Tyr Leu Lys
             100                 105                 110

Thr Lys Gly Leu Gly Ala Arg Glu Gly Glu Asp Leu Ile Asp Val Val
         115                 120                 125

Glu Val Gly Lys Cys Gly Asn Glu Asp Tyr Lys Glu Cys Ile Asn Asn
     130                 135                 140

Gly Thr Ala Thr Lys Cys Tyr Asn
145                 150

<210> SEQ ID NO 12
<211> LENGTH: 152
<212> TYPE: PRT
<213> ORGANISM: Avian pneumovirus

<400> SEQUENCE: 12

Met Thr Ser Thr Val Asn Leu Ser Ser Thr Ser Ser Arg Trp Thr Ala
1               5                   10                  15

Lys Ser Gln Cys Met Leu Cys Leu Arg Thr Met Met Asn Cys Ala Val
             20                  25                  30

Val Ile Cys Ala Leu Val Leu Ile Phe Leu Ala Thr Gly Leu Ser Val
             35                  40                  45

Lys Leu Val Thr Ile Glu Arg Asn Thr Cys Gln Leu Arg Leu Glu Leu
 50                  55                  60

Ser Thr Thr Ala Pro Ile Leu Arg Ser Pro Tyr Leu Gly Gly Ser Thr
65                  70                  75                  80

Ser Thr Pro Lys Leu Thr Thr Val Thr Ser Ile Thr Asp Leu Thr His
                 85                  90                  95

Gln Pro Gln Arg Lys Glu Leu Asn Gly Thr Ile Thr Tyr Ile Asn Ser
             100                 105                 110

Asp Gly Leu Asp Glu Lys Glu Gly Glu Ser Ile Asp Ile Glu Ile Ala
         115                 120                 125

Arg Val Thr Leu Cys Asp Pro Asn Pro Asn Tyr Asn His Cys Met Lys
     130                 135                 140

Asn Ser Thr Gly Leu Cys Tyr Asn
145                 150

<210> SEQ ID NO 13
<211> LENGTH: 55
<212> TYPE: PRT
<213> ORGANISM: Human respiratory syncytial virus

<400> SEQUENCE: 13

Met Glu Asn Thr Ser Thr Ile Glu Phe Ser Ser Lys Phe Trp Pro Tyr
1               5                   10                  15

Phe Leu Ile His Met Ile Thr Thr Ile Ser Leu Leu Ile Ile Ile Ser
             20                  25                  30

Ile Met Ile Ala Ile Leu Asn Leu Glu Tyr Asn Val Phe His Asn Lys
```

```
                35                  40                  45

Thr Phe Glu Leu Pro Arg Ala
    50                  55

<210> SEQ ID NO 14
<211> LENGTH: 70
<212> TYPE: PRT
<213> ORGANISM: Bovine respiratory syncytial virus

<400> SEQUENCE: 14

Met Asn Asn Thr Ser Thr Ile Glu Phe Thr Gly Glu Phe Trp Tyr Phe
1               5                   10                  15

Leu Ala Phe Met Met Leu Thr Gly Phe Phe Ile Val Thr Ser Leu
            20                  25                  30

Val Ala Ala Ile Leu Asn Leu Asp Phe Asn Asp His Thr Asn Ser
            35                  40                  45

Leu Asp Ile Arg Thr Arg Leu Asn Asp Gln Ile Thr Arg Ala His Gly
        50                  55                  60

Ser Ile Gln Ser Ser Asn
65                  70

<210> SEQ ID NO 15
<211> LENGTH: 83
<212> TYPE: PRT
<213> ORGANISM: Mouse pneumonia virus

<400> SEQUENCE: 15

Met Asp Pro Asn Met Thr Ser His Gln Thr Glu Ile Asn Met Thr Ser
1               5                   10                  15

Ser Arg Ile Gly His Thr Pro Ala Pro Thr Ala Pro Leu Leu Cys Ala
            20                  25                  30

Val Ile Asn Thr Val Ala Leu Ile Met Ala Cys Ser Ser Arg Ser Thr
        35                  40                  45

Ala Thr Ser Gly Ile Val Ser Ser Gln Thr Val His Asn His Pro Pro
    50                  55                  60

Pro Ser Tyr Gly Val Asn Val Gly Leu Pro Gly Asn Leu Tyr Ser Arg
65                  70                  75                  80

Asn Thr Thr

<210> SEQ ID NO 16
<211> LENGTH: 27
<212> TYPE: DNA
<213> ORGANISM: Avian pneumovirus

<400> SEQUENCE: 16
ggtgcaggag ttcaggtaat agtggag                                    27

<210> SEQ ID NO 17
<211> LENGTH: 29
<212> TYPE: DNA
<213> ORGANISM: Avian pneumovirus

<400> SEQUENCE: 17
gcatggtggc cttatcacca ctgggtgct                                  29

<210> SEQ ID NO 18
<211> LENGTH: 27
<212> TYPE: DNA
<213> ORGANISM: Avian pneumovirus
```

```
<400> SEQUENCE: 18
gcggagaaca tggcctgatc ttcctga                                          27

<210> SEQ ID NO 19
<211> LENGTH: 4
<212> TYPE: PRT
<213> ORGANISM: Avian pneumovirus

<400> SEQUENCE: 19

Arg Gln Lys Arg
1

<210> SEQ ID NO 20
<211> LENGTH: 4
<212> TYPE: PRT
<213> ORGANISM: Avian pneumovirus

<400> SEQUENCE: 20

Arg Gln Gly Arg
1

<210> SEQ ID NO 21
<211> LENGTH: 4
<212> TYPE: PRT
<213> ORGANISM: Avian pneumovirus

<400> SEQUENCE: 21

Arg Lys Ala Arg
1

<210> SEQ ID NO 22
<213> ORGANISM: Avian pneumovirus

<400> SEQUENCE: 22

000

<210> SEQ ID NO 23
<213> ORGANISM: Avian pneumovirus

<400> SEQUENCE: 23

000

<210> SEQ ID NO 24
<211> LENGTH: 40
<212> TYPE: DNA
<213> ORGANISM: Avian pneumovirus

<400> SEQUENCE: 24
acgagaaaaa aacgcatata agacaacttc caaacaaaac                            40

<210> SEQ ID NO 25
<211> LENGTH: 1206
<212> TYPE: DNA
<213> ORGANISM: Avian pneumovirus
<220> FEATURE:
<221> NAME/KEY: CDS
<222> LOCATION: (14)..(1198)

<400> SEQUENCE: 25
gggacaagtg aaa atg tct ctt cag ggg att cag ctt agt gat ttg tcc        49
             Met Ser Leu Gln Gly Ile Gln Leu Ser Asp Leu Ser
                 1               5                  10 tat aag cat gca atc ctt aaa gaa tca cag tac aca atc aaa aga gat       97
```

```
Tyr Lys His Ala Ile Leu Lys Glu Ser Gln Tyr Thr Ile Lys Arg Asp
         15                  20                  25 gtg ggg aca acc aca gct gtc act cca tct tct ctg cag agg gaa gta        145
Val Gly Thr Thr Thr Ala Val Thr Pro Ser Ser Leu Gln Arg Glu Val
     30                  35                  40 tca ctc tta tgt gga gag ata ctg tat acc aag cac aca gat tac tca        193
Ser Leu Leu Cys Gly Glu Ile Leu Tyr Thr Lys His Thr Asp Tyr Ser
 45                  50                  55                  60 cat aca gct gaa gta gga atg cag tat gtg agc acc aca ctg gga gca        241
His Thr Ala Glu Val Gly Met Gln Tyr Val Ser Thr Thr Leu Gly Ala
                 65                  70                  75 gaa cgt aca caa cag ata cta aag aac tca ggt agt gag gtg cag gca        289
Glu Arg Thr Gln Gln Ile Leu Lys Asn Ser Gly Ser Glu Val Gln Ala
             80                  85                  90 gtg ttg acc aag aca tac tct ctt ggg aag ggc aaa aac agc aaa ggg        337
Val Leu Thr Lys Thr Tyr Ser Leu Gly Lys Gly Lys Asn Ser Lys Gly
         95                 100                 105 gag gag ttg caa atg tta gac ata cat ggg gtt gaa aaa agt tgg gtt        385
Glu Glu Leu Gln Met Leu Asp Ile His Gly Val Glu Lys Ser Trp Val
    110                 115                 120 gaa gaa gtt gac aag gag gca agg aaa acc atg gcc tca gct aca aag        433
Glu Glu Val Asp Lys Glu Ala Arg Lys Thr Met Ala Ser Ala Thr Lys
125                 130                 135                 140 gac aac tca gga ccg ata cca caa aat caa aga cca tca tcc ccg gat        481
Asp Asn Ser Gly Pro Ile Pro Gln Asn Gln Arg Pro Ser Ser Pro Asp
                145                 150                 155 gct cct atc ata cta ctc tgc ata gga gca tta ata ttc acg aag ctg        529
Ala Pro Ile Ile Leu Leu Cys Ile Gly Ala Leu Ile Phe Thr Lys Leu
            160                 165                 170 gca tca aca atc gaa gtt ggg ctg gag aca gct gtt aga agg gca aac        577
Ala Ser Thr Ile Glu Val Gly Leu Glu Thr Ala Val Arg Arg Ala Asn
        175                 180                 185 cgc gtg ctg aat gat gca ttg aaa agg ttc cca agg atc gac atc ccc        625
Arg Val Leu Asn Asp Ala Leu Lys Arg Phe Pro Arg Ile Asp Ile Pro
    190                 195                 200 aaa att gca agg tcc ttt tat gat ctg ttt gag cag aaa gtt tac tat        673
Lys Ile Ala Arg Ser Phe Tyr Asp Leu Phe Glu Gln Lys Val Tyr Tyr
205                 210                 215                 220 agg agc ttg ttt ata gag tat ggc aaa gcc ctt ggg tct tct tcc aca        721
Arg Ser Leu Phe Ile Glu Tyr Gly Lys Ala Leu Gly Ser Ser Ser Thr
                225                 230                 235 gga agc aag gca gaa agt ctg ttt gtg aac att ttc atg caa gct tat        769
Gly Ser Lys Ala Glu Ser Leu Phe Val Asn Ile Phe Met Gln Ala Tyr
            240                 245                 250 ggt gca ggt cag aca atg cta agg tgg ggg gta att gcc aga tca tcc        817
Gly Ala Gly Gln Thr Met Leu Arg Trp Gly Val Ile Ala Arg Ser Ser
        255                 260                 265 aac aat ata atg ttg ggc cat gtc tcc gta caa gcg gaa ctc aaa cag        865
Asn Asn Ile Met Leu Gly His Val Ser Val Gln Ala Glu Leu Lys Gln
    270                 275                 280 gtc acg gag gta tat gat cta gtc aga gag atg ggc cct gag tca ggt        913
Val Thr Glu Val Tyr Asp Leu Val Arg Glu Met Gly Pro Glu Ser Gly
285                 290                 295                 300 ctt ctc cac ctg agg caa agc cct aag gct gga ttg ttg tca ctt gct        961
Leu Leu His Leu Arg Gln Ser Pro Lys Ala Gly Leu Leu Ser Leu Ala
                305                 310                 315 aat tgt cca aat ttt gca agt gtg gta cta gga aat gcc tca gga ttg       1009
Asn Cys Pro Asn Phe Ala Ser Val Val Leu Gly Asn Ala Ser Gly Leu
            320                 325                 330
```

```
                                                                     -continued ggg ata ctt ggt atg tac aga gga aga gta cca aac aca gag cta ttt      1057
Gly Ile Leu Gly Met Tyr Arg Gly Arg Val Pro Asn Thr Glu Leu Phe
        335                 340                 345 gct gca gca gaa agc tat gca aga agc cta aaa gaa agc aat aag ata      1105
Ala Ala Ala Glu Ser Tyr Ala Arg Ser Leu Lys Glu Ser Asn Lys Ile
350                 355                 360 aat ttc tca tct ctt ggt ctg aca gaa gag gaa aaa gaa gct gcc gag      1153
Asn Phe Ser Ser Leu Gly Leu Thr Glu Glu Glu Lys Glu Ala Ala Glu
365                 370                 375                 380 aac ttt ctc aac ata aat gag gaa ggc cag aat gat tat gag taa          1198
Asn Phe Leu Asn Ile Asn Glu Glu Gly Gln Asn Asp Tyr Glu
                    385                 390 ttaaaaaa                                                             1206

<210> SEQ ID NO 26
<211> LENGTH: 394
<212> TYPE: PRT
<213> ORGANISM: Avian pneumovirus

<400> SEQUENCE: 26

Met Ser Leu Gln Gly Ile Gln Leu Ser Asp Leu Ser Tyr Lys His Ala
1               5                   10                  15

Ile Leu Lys Glu Ser Gln Tyr Thr Ile Lys Arg Asp Val Gly Thr Thr
            20                  25                  30

Thr Ala Val Thr Pro Ser Ser Leu Gln Arg Glu Val Ser Leu Leu Cys
        35                  40                  45

Gly Glu Ile Leu Tyr Thr Lys His Thr Asp Tyr Ser His Thr Ala Glu
    50                  55                  60

Val Gly Met Gln Tyr Val Ser Thr Thr Leu Gly Ala Glu Arg Thr Gln
65                  70                  75                  80

Gln Ile Leu Lys Asn Ser Gly Ser Glu Val Gln Ala Val Leu Thr Lys
                85                  90                  95

Thr Tyr Ser Leu Gly Lys Gly Lys Asn Ser Lys Gly Glu Glu Leu Gln
            100                 105                 110

Met Leu Asp Ile His Gly Val Glu Lys Ser Trp Val Glu Glu Val Asp
        115                 120                 125

Lys Glu Ala Arg Lys Thr Met Ala Ser Ala Thr Lys Asp Asn Ser Gly
    130                 135                 140

Pro Ile Pro Gln Asn Gln Arg Pro Ser Ser Pro Asp Ala Pro Ile Ile
145                 150                 155                 160

Leu Leu Cys Ile Gly Ala Leu Ile Phe Thr Lys Leu Ala Ser Thr Ile
                165                 170                 175

Glu Val Gly Leu Glu Thr Ala Val Arg Arg Ala Asn Arg Val Leu Asn
            180                 185                 190

Asp Ala Leu Lys Arg Phe Pro Arg Ile Asp Ile Pro Lys Ile Ala Arg
        195                 200                 205

Ser Phe Tyr Asp Leu Phe Glu Gln Lys Val Tyr Tyr Arg Ser Leu Phe
    210                 215                 220

Ile Glu Tyr Gly Lys Ala Leu Gly Ser Ser Thr Gly Ser Lys Ala
225                 230                 235                 240

Glu Ser Leu Phe Val Asn Ile Phe Met Gln Ala Tyr Gly Ala Gly Gln
                245                 250                 255

Thr Met Leu Arg Trp Gly Val Ile Ala Arg Ser Ser Asn Asn Ile Met
            260                 265                 270

Leu Gly His Val Ser Val Gln Ala Glu Leu Lys Gln Val Thr Glu Val
        275                 280                 285
```

```
Tyr Asp Leu Val Arg Glu Met Gly Pro Glu Ser Gly Leu Leu His Leu
    290                 295                 300

Arg Gln Ser Pro Lys Ala Gly Leu Leu Ser Leu Ala Asn Cys Pro Asn
305                 310                 315                 320

Phe Ala Ser Val Val Leu Gly Asn Ala Ser Leu Gly Ile Leu Gly
                325                 330                 335

Met Tyr Arg Gly Arg Val Pro Asn Thr Glu Leu Phe Ala Ala Ala Glu
            340                 345                 350

Ser Tyr Ala Arg Ser Leu Lys Glu Ser Asn Lys Ile Asn Phe Ser Ser
        355                 360                 365

Leu Gly Leu Thr Glu Glu Lys Glu Ala Ala Glu Asn Phe Leu Asn
    370                 375                 380

Ile Asn Glu Glu Gly Gln Asn Asp Tyr Glu
385                 390

<210> SEQ ID NO 27
<211> LENGTH: 909
<212> TYPE: DNA
<213> ORGANISM: Avian pneumovirus
<220> FEATURE:
<221> NAME/KEY: CDS
<222> LOCATION: (14)..(898)

<400> SEQUENCE:

-continued

```
                 175                 180                 185
ttg cta aga aca ctc aat gtt gcc acg gct ggg ccc acc gca gcc aga      625
Leu Leu Arg Thr Leu Asn Val Ala Thr Ala Gly Pro Thr Ala Ala Arg
    190                 195                 200 gac ggc att cgg gat gca atg gta gga ttg aga gaa gaa tta att gct      673
Asp Gly Ile Arg Asp Ala Met Val Gly Leu Arg Glu Glu Leu Ile Ala
205                 210                 215                 220 gat atc atc aaa gaa gca aaa ggg aag gca gcc gag atg atg aaa gag      721
Asp Ile Ile Lys Glu Ala Lys Gly Lys Ala Ala Glu Met Met Lys Glu
                225                 230                 235 gaa gca aag cag aag tca aaa ata ggg aat ggg agc gta ggc cta act      769
Glu Ala Lys Gln Lys Ser Lys Ile Gly Asn Gly Ser Val Gly Leu Thr
            240                 245                 250 gag aag gcc aag gaa ctg aac aaa ata gtg gag gac gag agc aca agt      817
Glu Lys Ala Lys Glu Leu Asn Lys Ile Val Glu Asp Glu Ser Thr Ser
        255                 260                 265 ggt gag tca gag gaa gaa gaa gag gaa gaa gat gaa gaa gag agc aac      865
Gly Glu Ser Glu Glu Glu Glu Glu Glu Asp Glu Glu Glu Ser Asn
    270                 275                 280 cca gat gat gac cta tac tcc ctt act atg tag ttaataaaaa a            909
Pro Asp Asp Asp Leu Tyr Ser Leu Thr Met
285                 290

<210> SEQ ID NO 28
<211> LENGTH: 294
<212> TYPE: PRT
<213> ORGANISM: Avian pneumovirus

<400> SEQUENCE: 28

Met Ser Phe Pro Glu Gly Lys Asp Ile Leu Leu Met Gly Asn Glu Ala
1               5                   10                  15

Ala Lys Ala Ala Glu Ala Phe Gln Arg Ser Leu Lys Lys Ile Gly His
                20                  25                  30

Arg Arg Thr Gln Ser Ile Val Gly Asp Lys Ile Ile Thr Val Ser Glu
            35                  40                  45

Thr Val Glu Lys Pro Thr Ile Ser Lys Ser Thr Lys Val Thr Thr Pro
        50                  55                  60

Pro Glu Arg Lys Asn Ala Trp Gly Glu Lys Pro Asp Thr Thr Arg Ser
65                  70                  75                  80

Gln Thr Glu Glu Ala Arg Asn Glu Ala Thr Pro Glu Asp Ala Ser Arg
                85                  90                  95

Leu Tyr Glu Glu Val Phe Ala Pro Thr Ser Asp Gly Lys Thr Pro Ala
            100                 105                 110

Glu Lys Gly Lys Glu Thr Pro Glu Lys Pro Lys Lys Val Thr Phe
        115                 120                 125

Lys Asn Asp Glu Ser Gly Arg Tyr Thr Lys Leu Glu Met Glu Ala Leu
    130                 135                 140

Glu Leu Leu Ser Asp Asn Glu Asp Asp Ala Glu Ser Ser Val Leu
145                 150                 155                 160

Thr Phe Glu Glu Lys Asp Thr Ser Ala Leu Ser Leu Glu Ala Arg Leu
                165                 170                 175

Glu Ser Ile Asp Glu Lys Leu Ser Met Ile Leu Gly Leu Leu Arg Thr
            180                 185                 190

Leu Asn Val Ala Thr Ala Gly Pro Thr Ala Ala Arg Asp Gly Ile Arg
        195                 200                 205

Asp Ala Met Val Gly Leu Arg Glu Glu Leu Ile Ala Asp Ile Ile Lys
    210                 215                 220
```

```
Glu Ala Lys Gly Lys Ala Ala Glu Met Met Lys Glu Ala Lys Gln
225                 230                 235                 240

Lys Ser Lys Ile Gly Asn Gly Ser Val Gly Leu Thr Glu Lys Ala Lys
            245                 250                 255

Glu Leu Asn Lys Ile Val Glu Asp Glu Ser Thr Ser Gly Glu Ser Glu
                260                 265                 270

Glu Glu Glu Glu Glu Asp Glu Glu Ser Asn Pro Asp Asp
        275                 280                 285

Leu Tyr Ser Leu Thr Met
    290
```

<210> SEQ ID NO 29
<211> LENGTH: 868
<212> TYPE: DNA
<213> ORGANISM: Avian pneumovirus
<220> FEATURE:
<221> NAME/KEY: CDS
<222> LOCATION: (14)..(778)

<400> SEQUENCE: 29

```
gggacaagtg  gaa atg gag tcc tat cta gta gac act tac caa ggt gtc         49
            Met Glu Ser Tyr Leu Val Asp Thr Tyr Gln Gly Val
              1               5                  10 cct tac act gct gct gta caa act gat ttg gtg gag aaa gac caa ctg         97
Pro Tyr Thr Ala Ala Val Gln Thr Asp Leu Val Glu Lys Asp Gln Leu
         15                  20                  25 cct gca agg tta aca gtg tgg gtc cct tta ttc caa acc aac aca cct        145
Pro Ala Arg Leu Thr Val Trp Val Pro Leu Phe Gln Thr Asn Thr Pro
 30                  35                  40 cct aca gtg cta cta gag cag ctt aag act ctg aca att aca act ttg        193
Pro Thr Val Leu Leu Glu Gln Leu Lys Thr Leu Thr Ile Thr Thr Leu
 45                  50                  55                  60 tac aca gcc tct cag aat ggc cca ata ctg aag gtc aat gca tca gca        241
Tyr Thr Ala Ser Gln Asn Gly Pro Ile Leu Lys Val Asn Ala Ser Ala
                 65                  70                  75 caa ggg gct gca atg tca gca ttg cca aaa agc ttt gat gtt agt gca        289
Gln Gly Ala Ala Met Ser Ala Leu Pro Lys Ser Phe Asp Val Ser Ala
             80                  85                  90 tca gta gca cta gat gac tac agc aaa cta gag ttt gac aaa ctg aca        337
Ser Val Ala Leu Asp Asp Tyr Ser Lys Leu Glu Phe Asp Lys Leu Thr
         95                 100                 105 gtg tgt gag tta aaa gca gtc tat ttg aca aca atg aaa cct tat ggt        385
Val Cys Glu Leu Lys Ala Val Tyr Leu Thr Thr Met Lys Pro Tyr Gly
110                 115                 120 atg gtc tca aag ttt gtc aac tca gcc aaa gca gtc ggg aag aaa aca        433
Met Val Ser Lys Phe Val Asn Ser Ala Lys Ala Val Gly Lys Lys Thr
125                 130                 135                 140 cac gat ttg att gct ctc tgt gac ttc ctt gac cta gag aag gga gtt        481
His Asp Leu Ile Ala Leu Cys Asp Phe Leu Asp Leu Glu Lys Gly Val
                145                 150                 155 cca gtg act ata cca gcc tat ata aag tct gtg tca ata aaa gag agt        529
Pro Val Thr Ile Pro Ala Tyr Ile Lys Ser Val Ser Ile Lys Glu Ser
            160                 165                 170 gaa tca gca act gtt gaa gct gca att agt ggg gag gca gat caa gct        577
Glu Ser Ala Thr Val Glu Ala Ala Ile Ser Gly Glu Ala Asp Gln Ala
        175                 180                 185 ata act caa gct agg att gct cca tac gct ggc ttg atc atg ata atg        625
Ile Thr Gln Ala Arg Ile Ala Pro Tyr Ala Gly Leu Ile Met Ile Met
    190                 195                 200
```

```
aca atg aac aac cct aag ggg atc ttc aaa aaa ctg ggt gca gga gtt    673
Thr Met Asn Asn Pro Lys Gly Ile Phe Lys Lys Leu Gly Ala Gly Val
205                 210                 215                 220 cag gta ata gtg gag tta ggg gca tac gtt caa gca gaa agc ata agc    721
Gln Val Ile Val Glu Leu Gly Ala Tyr Val Gln Ala Glu Ser Ile Ser
            225                 230                 235 aga atc tgc agg aac tgg agc cac cag ggt acg aga tat gtc ctg aag    769
Arg Ile Cys Arg Asn Trp Ser His Gln Gly Thr Arg Tyr Val Leu Lys
        240                 245                 250 tca aga taa acacagagag tacacttacc aaatcacagt aacaatttcg             818
Ser Arg tttttaaccc tctcatagtt attacctagc ttgatattat ttagaaaaaa              868

<210> SEQ ID NO 30
<211> LENGTH: 254
<212> TYPE: PRT
<213> ORGANISM: Avian pneumovirus

<400> SEQUENCE: 30

Met Glu Ser Tyr Leu Val Asp Thr Tyr Gln Gly Val Pro Tyr Thr Ala
1               5                   10                  15

Ala Val Gln Thr Asp Leu Val Glu Lys Asp Gln Leu Pro Ala Arg Leu
            20                  25                  30

Thr Val Trp Val Pro Leu Phe Gln Thr Asn Thr Pro Thr Val Leu
        35                  40                  45

Leu Glu Gln Leu Lys Thr Leu Thr Ile Thr Thr Leu Tyr Thr Ala Ser
    50                  55                  60

Gln Asn Gly Pro Ile Leu Lys Val Asn Ala Ser Ala Gln Gly Ala Ala
65                  70                  75                  80

Met Ser Ala Leu Pro Lys Ser Phe Asp Val Ser Ala Ser Val Ala Leu
                85                  90                  95

Asp Asp Tyr Ser Lys Leu Glu Phe Asp Lys Leu Thr Val Cys Glu Leu
            100                 105                 110

Lys Ala Val Tyr Leu Thr Thr Met Lys Pro Tyr Gly Met Val Ser Lys
        115                 120                 125

Phe Val Asn Ser Ala Lys Ala Val Gly Lys Lys Thr His Asp Leu Ile
    130                 135                 140

Ala Leu Cys Asp Phe Leu Asp Leu Glu Lys Gly Val Pro Val Thr Ile
145                 150                 155                 160

Pro Ala Tyr Ile Lys Ser Val Ser Ile Lys Glu Ser Glu Ser Ala Thr
                165                 170                 175

Val Glu Ala Ala Ile Ser Gly Glu Ala Asp Gln Ala Ile Thr Gln Ala
            180                 185                 190

Arg Ile Ala Pro Tyr Ala Gly Leu Ile Met Ile Met Thr Met Asn Asn
        195                 200                 205

Pro Lys Gly Ile Phe Lys Lys Leu Gly Ala Gly Val Gln Val Ile Val
    210                 215                 220

Glu Leu Gly Ala Tyr Val Gln Ala Glu Ser Ile Ser Arg Ile Cys Arg
225                 230                 235                 240

Asn Trp Ser His Gln Gly Thr Arg Tyr Val Leu Lys Ser Arg
                245                 250

<210> SEQ ID NO 31
<211> LENGTH: 1644
<212> TYPE: DNA
<213> ORGANISM: Avian pneumovirus
<220> FEATURE:
```

<221> NAME/KEY: CDS
<222> LOCATION: (14)..(1627)

<400> SEQUENCE: 31

```
gggacaagtg aaa atg tct tgg aaa gtg gta ctg cta ttg gta ttg cta              49
            Met Ser Trp Lys Val Val Leu Leu Leu Val Leu Leu
             1               5                  10 gct acc cca acg ggg ggg cta gaa gaa agt tat cta gag gag tca tgc              97
Ala Thr Pro Thr Gly Gly Leu Glu Glu Ser Tyr Leu Glu Glu Ser Cys
            15                  20                  25 agt act gtt act aga gga tac ctg agt gtt ttg agg aca gga tgg tat             145
Ser Thr Val Thr Arg Gly Tyr Leu Ser Val Leu Arg Thr Gly Trp Tyr
 30                  35                  40 aca aat gtg ttc aca ctt gag gtt gga gat gtg gaa aat ctc aca tgt             193
Thr Asn Val Phe Thr Leu Glu Val Gly Asp Val Glu Asn Leu Thr Cys
 45                  50                  55                  60 acc gac ggg ccc agc tta ata aga aca gaa ctt gaa ctg aca aaa aat             241
Thr Asp Gly Pro Ser Leu Ile Arg Thr Glu Leu Glu Leu Thr Lys Asn
                 65                  70                  75 gca ctt gag gaa ctc aag aca gta tca gca gat caa ttg gca aag gaa             289
Ala Leu Glu Glu Leu Lys Thr Val Ser Ala Asp Gln Leu Ala Lys Glu
             80                  85                  90 gct agg ata atg tca cca aga aaa gcc cgg ttt gtt ctg ggt gcc ata             337
Ala Arg Ile Met Ser Pro Arg Lys Ala Arg Phe Val Leu Gly Ala Ile
         95                  100                 105 gca tta ggt gtg gca act gct gct gct gtg acg gct ggt gta gcg ata             385
Ala Leu Gly Val Ala Thr Ala Ala Ala Val Thr Ala Gly Val Ala Ile
 110                 115                 120 gcc aag aca att agg cta gaa gga gaa gtg gct gca atc aag ggt gcg             433
Ala Lys Thr Ile Arg Leu Glu Gly Glu Val Ala Ala Ile Lys Gly Ala
 125                 130                 135                 140 ctc agg aaa aca aat gag gct gta tct aca tta gga aat ggc gtg agg             481
Leu Arg Lys Thr Asn Glu Ala Val Ser Thr Leu Gly Asn Gly Val Arg
                 145                 150                 155 gta ctt gca aca gct gtg aat gat ctc aag gac ttt ata agt aaa aaa             529
Val Leu Ala Thr Ala Val Asn Asp Leu Lys Asp Phe Ile Ser Lys Lys
             160                 165                 170 ttg aca cct gca ata aac agg aac aag tgt gac atc tca gac ctt aag             577
Leu Thr Pro Ala Ile Asn Arg Asn Lys Cys Asp Ile Ser Asp Leu Lys
         175                 180                 185 atg gca gtg agc ttt gga caa tac aat cgg agg ttc ctc aat gtg gta             625
Met Ala Val Ser Phe Gly Gln Tyr Asn Arg Arg Phe Leu Asn Val Val
 190                 195                 200 aga cag ttt tct gac aat gca ggt att acg cct gca ata tct cta gat             673
Arg Gln Phe Ser Asp Asn Ala Gly Ile Thr Pro Ala Ile Ser Leu Asp
 205                 210                 215                 220 tta atg act gac gct gag ctt gta aga gct gta agc aac atg ccc aca             721
Leu Met Thr Asp Ala Glu Leu Val Arg Ala Val Ser Asn Met Pro Thr
                 225                 230                 235 tct tca gga cag atc aat ctg atg ctt gag aat cgg gca atg gtc aga             769
Ser Ser Gly Gln Ile Asn Leu Met Leu Glu Asn Arg Ala Met Val Arg
             240                 245                 250 agg aaa gga ttt ggg att ttg att gga gtt tat ggt agc tct gtg gtc             817
Arg Lys Gly Phe Gly Ile Leu Ile Gly Val Tyr Gly Ser Ser Val Val
         255                 260                 265 tat ata gtg cag ctt cct att ttc ggt gtg ata gat aca ccg tgt tgg             865
Tyr Ile Val Gln Leu Pro Ile Phe Gly Val Ile Asp Thr Pro Cys Trp
 270                 275                 280 aag gtg aag gct gct cca tta tgt tca ggg aaa gac ggg aat tat gca             913
Lys Val Lys Ala Ala Pro Leu Cys Ser Gly Lys Asp Gly Asn Tyr Ala
```

```
                285                 290                 295                 300
tgt ctc ttg cga gag gac caa ggt tgg tat tgt caa aat gct gga tcc         961
Cys Leu Leu Arg Glu Asp Gln Gly Trp Tyr Cys Gln Asn Ala Gly Ser
                305                 310                 315 aca gtt tat tat cca aat gag gag gac tgt gaa gta aga agt gat cat        1009
Thr Val Tyr Tyr Pro Asn Glu Glu Asp Cys Glu Val Arg Ser Asp His
        320                 325                 330 gtg ttt tgt gac aca gca gct ggg ata aat gta gca aag gag tca gaa        1057
Val Phe Cys Asp Thr Ala Ala Gly Ile Asn Val Ala Lys Glu Ser Glu
            335                 340                 345 gag tgc aac agg aat atc tca aca aca aag tac cct tgc aag gta agt        1105
Glu Cys Asn Arg Asn Ile Ser Thr Thr Lys Tyr Pro Cys Lys Val Ser
    350                 355                 360 aca ggg cgt cac cca ata agc atg gtg gcc tta tca cca ctg ggt gct        1153
Thr Gly Arg His Pro Ile Ser Met Val Ala Leu Ser Pro Leu Gly Ala
365                 370                 375                 380 ttg gta gcc tgt tat gac ggt atg agt tgt tcc att gga agc aac aag        1201
Leu Val Ala Cys Tyr Asp Gly Met Ser Cys Ser Ile Gly Ser Asn Lys
                385                 390                 395 gtt gga ata atc aga cct ttg ggg aaa ggg tgt tca tac atc agc aat        1249
Val Gly Ile Ile Arg Pro Leu Gly Lys Gly Cys Ser Tyr Ile Ser Asn
        400                 405                 410 caa gat gct gac act gtt aca att gac aac aca gtg tac caa ttg agc        1297
Gln Asp Ala Asp Thr Val Thr Ile Asp Asn Thr Val Tyr Gln Leu Ser
            415                 420                 425 aaa gtt gaa gga gaa caa cac aca att aaa ggg aag cca gta tct agc        1345
Lys Val Glu Gly Glu Gln His Thr Ile Lys Gly Lys Pro Val Ser Ser
    430                 435                 440 aat ttt gac cct ata gag ttc cct gaa gat cag ttc aac ata gcc ctg        1393
Asn Phe Asp Pro Ile Glu Phe Pro Glu Asp Gln Phe Asn Ile Ala Leu
445                 450                 455                 460 gat cag gtg ttt gaa agt gtt gag aag agt cag aat ctg ata gac cag        1441
Asp Gln Val Phe Glu Ser Val Glu Lys Ser Gln Asn Leu Ile Asp Gln
                465                 470                 475 tca aac aag ata ttg gat agc att gaa aag ggg aat gca gga ttt gtc        1489
Ser Asn Lys Ile Leu Asp Ser Ile Glu Lys Gly Asn Ala Gly Phe Val
        480                 485                 490 ata gtg ata gtc ctc att gtc ctg ctc atg ctg gca gca gtt ggt gtg        1537
Ile Val Ile Val Leu Ile Val Leu Leu Met Leu Ala Ala Val Gly Val
            495                 500                 505 ggt gtc ttc ttt gtg gtt aag aag aga aaa gct gct ccc aaa ttc cca        1585
Gly Val Phe Phe Val Val Lys Lys Arg Lys Ala Ala Pro Lys Phe Pro
    510                 515                 520 atg gaa atg aat ggt gtg aac aac aaa gga ttt atc cct taa               1627
Met Glu Met Asn Gly Val Asn Asn Lys Gly Phe Ile Pro
525                 530                 535 ttttagttac taaaaaa                                                     1644

<210> SEQ ID NO 32
<211> LENGTH: 537
<212> TYPE: PRT
<213> ORGANISM: Avian pneumovirus

<400> SEQUENCE: 32

Met Ser Trp Lys Val Val Leu Leu Val Leu Leu Ala Thr Pro Thr
1               5                   10                  15

Gly Gly Leu Glu Glu Ser Tyr Leu Glu Glu Ser Cys Ser Thr Val Thr
            20                  25                  30

Arg Gly Tyr Leu Ser Val Leu Arg Thr Gly Trp Tyr Thr Asn Val Phe
```

-continued

```
                35                  40                  45
Thr Leu Glu Val Gly Asp Val Glu Asn Leu Thr Cys Thr Asp Gly Pro
 50                  55                  60

Ser Leu Ile Arg Thr Glu Leu Glu Leu Thr Lys Asn Ala Leu Glu Glu
65                  70                  75                  80

Leu Lys Thr Val Ser Ala Asp Gln Leu Ala Lys Glu Ala Arg Ile Met
                 85                  90                  95

Ser Pro Arg Lys Ala Arg Phe Val Leu Gly Ala Ile Ala Leu Gly Val
            100                 105                 110

Ala Thr Ala Ala Ala Val Thr Ala Gly Val Ala Ile Ala Lys Thr Ile
        115                 120                 125

Arg Leu Glu Gly Glu Val Ala Ala Ile Lys Gly Ala Leu Arg Lys Thr
130                 135                 140

Asn Glu Ala Val Ser Thr Leu Gly Asn Gly Val Arg Val Leu Ala Thr
145                 150                 155                 160

Ala Val Asn Asp Leu Lys Asp Phe Ile Ser Lys Lys Leu Thr Pro Ala
                165                 170                 175

Ile Asn Arg Asn Lys Cys Asp Ile Ser Asp Leu Lys Met Ala Val Ser
            180                 185                 190

Phe Gly Gln Tyr Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
    210                 215                 220

Ala Glu Leu Val Arg Ala Val Ser Asn Met Pro Thr Ser Ser Gly Gln
225                 230                 235                 240

Ile Asn Leu Met Leu Glu Asn Arg Ala Met Val Arg Arg Lys Gly Phe
                245                 250                 255

Gly Ile Leu Ile Gly Val Tyr Gly Ser Ser Val Val Tyr Ile Val Gln
            260                 265                 270

Leu Pro Ile Phe Gly Val Ile Asp Thr Pro Cys Trp Lys Val Lys Ala
        275                 280                 285

Ala Pro Leu Cys Ser Gly Lys Asp Gly Asn Tyr Ala Cys Leu Leu Arg
    290                 295                 300

Glu Asp Gln Gly Trp Tyr Cys Gln Asn Ala Gly Ser Thr Val Tyr Tyr
305                 310                 315                 320

Pro Asn Glu Glu Asp Cys Glu Val Arg Ser Asp His Val Phe Cys Asp
                325                 330                 335

Thr Ala Ala Gly Ile Asn Val Ala Lys Glu Ser Glu Glu Cys Asn Arg
            340                 345                 350

Asn Ile Ser Thr Thr Lys Tyr Pro Cys Lys Val Ser Thr Gly Arg His
        355                 360                 365

Pro Ile Ser Met Val Ala Leu Ser Pro Leu Gly Ala Leu Val Ala Cys
    370                 375                 380

Tyr Asp Gly Met Ser Cys Ser Ile Gly Ser Asn Lys Val Gly Ile Ile
385                 390                 395                 400

Arg Pro Leu Gly Lys Gly Cys Ser Tyr Ile Ser Asn Gln Asp Ala Asp
                405                 410                 415

Thr Val Thr Ile Asp Asn Thr Val Tyr Gln Leu Ser Lys Val Glu Gly
            420                 425                 430

Glu Gln His Thr Ile Lys Gly Lys Pro Val Ser Ser Asn Phe Asp Pro
        435                 440                 445

Ile Glu Phe Pro Glu Asp Gln Phe Asn Ile Ala Leu Asp Gln Val Phe
    450                 455                 460
```

```
Glu Ser Val Glu Lys Ser Gln Asn Leu Ile Asp Gln Ser Asn Lys Ile
465                 470                 475                 480

Leu Asp Ser Ile Glu Lys Gly Asn Ala Gly Phe Val Ile Val Ile Val
                485                 490                 495

Leu Ile Val Leu Leu Met Leu Ala Ala Val Gly Val Gly Val Phe Phe
                500                 505                 510

Val Val Lys Lys Arg Lys Ala Ala Pro Lys Phe Pro Met Glu Met Asn
                515                 520                 525

Gly Val Asn Asn Lys Gly Phe Ile Pro
        530                 535

<210> SEQ ID NO 33
<211> LENGTH: 748
<212> TYPE: DNA
<213> ORGANISM: Avian pneumovirus
<220> FEATURE:
<221> NAME/KEY: CDS
<222> LOCATION: (14)..(568)

<400> SEQUENCE: 33
```

| | | | |
|---|---|---|---|
| gggacaagtg aag atg tct cgc aag gct ccc tgc aaa tat gaa gta cgg | | | 49 |
| Met Ser Arg Lys Ala Pro Cys Lys Tyr Glu Val Arg | | | |
| 1 5 10 | | | |
| ggc aag tgc aat aga ggc agt gaa tgc aaa ttt aac cat aat tat tgg | | | 97 |
| Gly Lys Cys Asn Arg Gly Ser Glu Cys Lys Phe Asn His Asn Tyr Trp | | | |
| 15 20 25 | | | |
| tcc tgg cct gac agg tac ctg tta cta agg tcc aat tac ctg ctg aat | | | 145 |
| Ser Trp Pro Asp Arg Tyr Leu Leu Leu Arg Ser Asn Tyr Leu Leu Asn | | | |
| 30 35 40 | | | |
| caa tta ctg aga aat aca gat aga tca gat ggc ctg tca tta atc tca | | | 193 |
| Gln Leu Leu Arg Asn Thr Asp Arg Ser Asp Gly Leu Ser Leu Ile Ser | | | |
| 45 50 55 60 | | | |
| gga gca ggg cga gat gat agg aca caa gat ttt gtt ttg ggg tca aca | | | 241 |
| Gly Ala Gly Arg Asp Asp Arg Thr Gln Asp Phe Val Leu Gly Ser Thr | | | |
| 65 70 75 | | | |
| aat gtg gtc cag aac tac att gat aac aat gag aat ata aca aaa gca | | | 289 |
| Asn Val Val Gln Asn Tyr Ile Asp Asn Asn Glu Asn Ile Thr Lys Ala | | | |
| 80 85 90 | | | |
| tca act tgt tat agt ctg tat aat atc ata aaa caa ctg caa gag act | | | 337 |
| Ser Thr Cys Tyr Ser Leu Tyr Asn Ile Ile Lys Gln Leu Gln Glu Thr | | | |
| 95 100 105 | | | |
| gac gta agg cag gcc aga gac aac aaa gtt gat gac agc aag cat gtt | | | 385 |
| Asp Val Arg Gln Ala Arg Asp Asn Lys Val Asp Asp Ser Lys His Val | | | |
| 110 115 120 | | | |
| gct cta cat aat tta gtg ttg tca tat atg gaa atg agc aaa acc cct | | | 433 |
| Ala Leu His Asn Leu Val Leu Ser Tyr Met Glu Met Ser Lys Thr Pro | | | |
| 125 130 135 140 | | | |
| gca tcc ttg ata aac aat ttg aag aag ctt ccc aag gaa aaa cta aag | | | 481 |
| Ala Ser Leu Ile Asn Asn Leu Lys Lys Leu Pro Lys Glu Lys Leu Lys | | | |
| 145 150 155 | | | |
| aaa ttg gca aag ctg atc att gaa ttg tca gca gga gtg gaa aat gac | | | 529 |
| Lys Leu Ala Lys Leu Ile Ile Glu Leu Ser Ala Gly Val Glu Asn Asp | | | |
| 160 165 170 | | | |
| tct aca gct gcc atg caa gat agt gca aac tct gat taa atgcggagaa | | | 578 |
| Ser Thr Ala Ala Met Gln Asp Ser Ala Asn Ser Asp | | | |
| 175 180 | | | |
| catggcctga tcttcctgaa gatgaaatta gatgatatgg tatggactaa aaatgaattg | | | 638 |
| gtagacataa tttccactga aatagttaaa gtgcatgcta atatattcaa atgtaggcta | | | 698 | gaggatattg aaatcattta tgttaaaaca tttctaagtt aataaaaaaa           748

<210> SEQ ID NO 34
<211> LENGTH: 184
<212> TYPE: PRT
<213> ORGANISM: Avian pneumovirus

<400> SEQUENCE: 34

Met Ser Arg Lys Ala Pro Cys Lys Tyr Glu Val Arg Gly Lys Cys Asn
1               5                   10                  15

Arg Gly Ser Glu Cys Lys Phe Asn His Asn Tyr Trp Ser Trp Pro Asp
            20                  25                  30

Arg Tyr Leu Leu Leu Arg Ser Asn Tyr Leu Leu Asn Gln Leu Leu Arg
        35                  40                  45

Asn Thr Asp Arg Ser Asp Gly Leu Ser Leu Ile Ser Gly Ala Gly Arg
    50                  55                  60

Asp Asp Arg Thr Gln Asp Phe Val Leu Gly Ser Thr Asn Val Val Gln
65                  70                  75                  80

Asn Tyr Ile Asp Asn Asn Glu Asn Ile Thr Lys Ala Ser Thr Cys Tyr
                85                  90                  95

Ser Leu Tyr Asn Ile Ile Lys Gln Leu Gln Glu Thr Asp Val Arg Gln
            100                 105                 110

Ala Arg Asp Asn Lys Val Asp Asp Ser Lys His Val Ala Leu His Asn
        115                 120                 125

Leu Val Leu Ser Tyr Met Glu Met Ser Lys Thr Pro Ala Ser Leu Ile
    130                 135                 140

Asn Asn Leu Lys Lys Leu Pro Lys Glu Lys Leu Lys Lys Leu Ala Lys
145                 150                 155                 160

Leu Ile Ile Glu Leu Ser Ala Gly Val Glu Asn Asp Ser Thr Ala Ala
                165                 170                 175

Met Gln Asp Ser Ala Asn Ser Asp
            180

<210> SEQ ID NO 35
<211> LENGTH: 783
<212> TYPE: DNA
<213> ORGANISM: Avian pneumovirus
<220> FEATURE:
<221> NAME/KEY: CDS
<222> LOCATION: (14)..(772)

<400> SEQUENCE: 35
gggacaagtc aac atg gag gtc aag gta gag aat gtt ggc aag tca cag           49
            Met Glu Val Lys Val Glu Asn Val Gly Lys Ser Gln
            1               5                   10 gag ctt aaa gtc aaa gtc aag aat ttt ata aaa agg tct gat tgc aag          97
Glu Leu Lys Val Lys Val Lys Asn Phe Ile Lys Arg Ser Asp Cys Lys
        15                  20                  25 aaa aaa ctt ttt gcc ttg att tta ggg cta gtc agc ttt gaa ctc act         145
Lys Lys Leu Phe Ala Leu Ile Leu Gly Leu Val Ser Phe Glu Leu Thr
    30                  35                  40 atg aat ata atg ctg tct gtc atg tat gtg gag tca aat gag gcc cta         193
Met Asn Ile Met Leu Ser Val Met Tyr Val Glu Ser Asn Glu Ala Leu
45                  50                  55                  60 agt tta tgt agg atc caa ggg act cct gct cca agg gat aat aag aca         241
Ser Leu Cys Arg Ile Gln Gly Thr Pro Ala Pro Arg Asp Asn Lys Thr
                65                  70                  75 aac aca gaa aac gca aca aag gaa aca aca ctc cac aca acg acc aca         289
Asn Thr Glu Asn Ala Thr Lys Glu Thr Thr Leu His Thr Thr Thr Thr

```
                80                  85                  90
aca agg gat cca gag gtg agg gaa aca aaa acc acc aag ccc cag gcc       337
Thr Arg Asp Pro Glu Val Arg Glu Thr Lys Thr Thr Lys Pro Gln Ala
         95                 100                 105 aat gaa gga gca aca aac cca agc agg aac ctc acc acc aag gga gac       385
Asn Glu Gly Ala Thr Asn Pro Ser Arg Asn Leu Thr Thr Lys Gly Asp
110                 115                 120 aaa cac caa acg aca aga gca aca aca gag gca gaa ctg gaa aaa caa       433
Lys His Gln Thr Thr Arg Ala Thr Thr Glu Ala Glu Leu Glu Lys Gln
125                 130                 135                 140 agc aaa caa acc aca gag cca ggc acc agc acc caa aag cac acc ccc       481
Ser Lys Gln Thr Thr Glu Pro Gly Thr Ser Thr Gln Lys His Thr Pro
            145                 150                 155 aca aga cca agc agc aaa tcc ccc acc aca aca caa gca ata gca caa       529
Thr Arg Pro Ser Ser Lys Ser Pro Thr Thr Thr Gln Ala Ile Ala Gln
        160                 165                 170 ctg aca aca cca aca acc cca aaa gca agc aca gca ccc aag aac aga       577
Leu Thr Thr Pro Thr Thr Pro Lys Ala Ser Thr Ala Pro Lys Asn Arg
    175                 180                 185 cag gca aca acc aaa aaa acc gaa acg gac acc aca aca gca agc aga       625
Gln Ala Thr Thr Lys Lys Thr Glu Thr Asp Thr Thr Thr Ala Ser Arg
190                 195                 200 gca agg aac acc aac aac ccc aca gag aca gca aca aca act ccc aaa       673
Ala Arg Asn Thr Asn Asn Pro Thr Glu Thr Ala Thr Thr Thr Pro Lys
205                 210                 215                 220 gca aca aca gaa aca ggc aag agc aaa gag ggg cca aca cag cac aca       721
Ala Thr Thr Glu Thr Gly Lys Ser Lys Glu Gly Pro Thr Gln His Thr
            225                 230                 235 acc aaa gaa cag ccc gag aca aca gca gga gtt agt tta gaa gca agt       769
Thr Lys Glu Gln Pro Glu Thr Thr Ala Gly Val Ser Leu Glu Ala Ser
        240                 245                 250 tag ttaattaaaa a                                                      783

<210> SEQ ID NO 36
<211> LENGTH: 252
<212> TYPE: PRT
<213> ORGANISM: Avian pneumovirus

<400> SEQUENCE: 36

Met Glu Val Lys Val Glu Asn Val Gly Lys Ser Gln Glu Leu Lys Val
1               5                   10                  15

Lys Val Lys Asn Phe Ile Lys Arg Ser Asp Cys Lys Lys Lys Leu Phe
            20                  25                  30

Ala Leu Ile Leu Gly Leu Val Ser Phe Glu Leu Thr Met Asn Ile Met
        35                  40                  45

Leu Ser Val Met Tyr Val Glu Ser Asn Glu Ala Leu Ser Leu Cys Arg
    50                  55                  60

Ile Gln Gly Thr Pro Ala Pro Arg Asp Asn Lys Thr Asn Thr Glu Asn
65                  70                  75                  80

Ala Thr Lys Glu Thr Thr Leu His Thr Thr Thr Thr Arg Asp Pro
            85                  90                  95

Glu Val Arg Glu Thr Lys Thr Thr Lys Pro Gln Ala Asn Glu Gly Ala
                100                 105                 110

Thr Asn Pro Ser Arg Asn Leu Thr Thr Lys Gly Asp Lys His Gln Thr
        115                 120                 125

Thr Arg Ala Thr Thr Glu Ala Glu Leu Glu Lys Gln Ser Lys Gln Thr
    130                 135                 140
```

Thr Glu Pro Gly Thr Ser Thr Gln Lys His Thr Pro Thr Arg Pro Ser
145                 150                 155                 160

Ser Lys Ser Pro Thr Thr Thr Gln Ala Ile Ala Gln Leu Thr Thr Pro
                165                 170                 175

Thr Thr Pro Lys Ala Ser Thr Ala Pro Lys Asn Arg Gln Ala Thr Thr
            180                 185                 190

Lys Lys Thr Glu Thr Asp Thr Thr Thr Ala Ser Arg Ala Arg Asn Thr
        195                 200                 205

Asn Asn Pro Thr Glu Thr Ala Thr Thr Thr Pro Lys Ala Thr Thr Glu
    210                 215                 220

Thr Gly Lys Ser Lys Glu Gly Pro Thr Gln His Thr Thr Lys Glu Gln
225                 230                 235                 240

Pro Glu Thr Thr Ala Gly Val Ser Leu Glu Ala Ser
                245                 250

<210> SEQ ID NO 37
<211> LENGTH: 91
<212> TYPE: DNA
<213> ORGANISM: Avian pneumovirus

<400> SEQUENCE: 37
tcatgaatat gtctggacag tgccaaggcc aagaaaaacc aacacgagaa caggtgatcc        60
aatgattaaa aacgatcaga gaaggaaaaa c                                      91

<210> SEQ ID NO 38
<211> LENGTH: 40
<212> TYPE: DNA
<213> ORGANISM: Avian pneumovirus

<400> SEQUENCE: 38
atgaggaact aaaattggat gaatacggtt ttttctcgt                              40

<210> SEQ ID NO 39
<211> LENGTH: 49
<212> TYPE: RNA
<213> ORGANISM: Avian pneumovirus

<400> SEQUENCE: 39
ugcucuuuuu uugcguauau ucguugaag guuuguuug cccuguuca                     49

<210> SEQ ID NO 40
<211> LENGTH: 41
<212> TYPE: RNA
<213> ORGANISM: Avian pneumovirus

<400> SEQUENCE: 40
acgagaaaaa aaccguauuc auccaauuuu aguuccucau u                           41

<210> SEQ ID NO 41
<211> LENGTH: 9
<212> TYPE: RNA
<213> ORGANISM: Avian pneumovirus

<400> SEQUENCE: 41 gggacaagu                                                               9

<210> SEQ ID NO 42
<211> LENGTH: 9
<212> TYPE: RNA
<213> ORGANISM: Avian pneumovirus

```
<400> SEQUENCE: 42 aggaccaau                                                                9

<210> SEQ ID NO 43
<211> LENGTH: 12
<212> TYPE: RNA
<213> ORGANISM: Avian pneumovirus

<400> SEQUENCE: 43
uaguuauaaa aa                                                           12

<210> SEQ ID NO 44
<211> LENGTH: 12
<212> TYPE: DNA
<213> ORGANISM: Avian pneumovirus

<400> SEQUENCE: 44
agaaaagccc gg                                                           12

<210> SEQ ID NO 45
<211> LENGTH: 12
<212> TYPE: DNA
<213> ORGANISM: Avian pneumovirus
<220> FEATURE:
<221> NAME/KEY: misc_feature
<222> LOCATION: (3)..(3)
<223> OTHER INFORMATION: N can represent any nucleotide: a, t, c, or g
<220> FEATURE:
<221> NAME/KEY: misc_feature
<222> LOCATION: (12)..(12)
<223> OTHER INFORMATION: N can represent any nucleotide: a, t, c, or g

<400> SEQUENCE: 45
cgncagggac gn                                                           12

<210> SEQ ID NO 46
<211> LENGTH: 12
<212> TYPE: RNA
<213> ORGANISM: Avian pneumovirus

<400> SEQUENCE: 46
ucaauaaauu uu                                                           12

<210> SEQ ID NO 47
<211> LENGTH: 51
<212> TYPE: RNA
<213> ORGANISM: Avian pneumovirus

<400> SEQUENCE: 47
ugcgcuuuuu uugcgcauau uuaauucaau guuuuuugg uacccuguuc a                  51

<210> SEQ ID NO 48
<211> LENGTH: 49
<212> TYPE: RNA
<213> ORGANISM: Avian pneumovirus

<400> SEQUENCE: 48
ugcgcuuuuu uugcgcauau uuaauuuaag guuuguuuug cccuguuua                    49

<210> SEQ ID NO 49
<211> LENGTH: 39
<212> TYPE: RNA
<213> ORGANISM: Avian pneumovirus

<400> SEQUENCE: 49
```

```
acggcaaaaa aaccguauuc auccaauuuu aguuccuca                    39

<210> SEQ ID NO 50
<211> LENGTH: 40
<212> TYPE: RNA
<213> ORGANISM: Avian pneumovirus

<400> SEQUENCE: 50
acgagaaaaa aaccguauuc aucaaauuuu uagcuuuuag                   40

<210> SEQ ID NO 51
<211> LENGTH: 41
<212> TYPE: RNA
<213> ORGANISM: Avian pneumovirus

<400> SEQUENCE: 51
acggcaaaaa aaccguauua cauucaauua uaauuucuua u                 41

<210> SEQ ID NO 52
<211> LENGTH: 40
<212> TYPE: RNA
<213> ORGANISM: Avian pneumovirus

<400> SEQUENCE: 52
acggcaaaaa aaccguauac auucaauuuc aauucuuau                    40

<210> SEQ ID NO 53
<211> LENGTH: 28
<212> TYPE: RNA
<213> ORGANISM: Avian pneumovirus

<400> SEQUENCE: 53
ccguauacau ucaauuauaa uuucuuau                                28

<210> SEQ ID NO 54
<211> LENGTH: 40
<212> TYPE: RNA
<213> ORGANISM: Avian pneumovirus

<400> SEQUENCE: 54
ugcucuuuuu uugcguauau ucuguugaag guuuguuuug                   40

<210> SEQ ID NO 55
<211> LENGTH: 39
<212> TYPE: RNA
<213> ORGANISM: Avian pneumovirus

<400> SEQUENCE: 55
acggcaaaaa aaccguauuc auccaauuuu aguuccuca                    39

<210> SEQ ID NO 56
<211> LENGTH: 585
<212> TYPE: PRT
<213> ORGANISM: Avian pneumovirus

<400> SEQUENCE: 56

Met Glu Val Lys Val Glu Asn Val Gly Lys Ser Gln Glu Leu Lys Val
1               5                   10                  15

Lys Val Lys Asn Phe Ile Lys Arg Ser Asp Cys Lys Lys Lys Leu Phe
            20                  25                  30

Ala Leu Ile Leu Gly Leu Val Ser Phe Glu Leu Thr Met Asn Ile Met
        35                  40                  45
```

-continued

```
Leu Ser Val Met Tyr Val Glu Ser Asn Glu Ala Leu Ser Leu Cys Arg
     50                  55                  60

Ile Gln Gly Thr Pro Ala Pro Arg Asp Asn Lys Thr Asn Thr Glu Asn
 65                  70                  75                  80

Ala Thr Lys Glu Thr Thr Leu His Thr Thr Thr Thr Arg Asp Pro
                 85                  90                  95

Glu Val Arg Glu Thr Lys Thr Thr Lys Pro Gln Ala Asn Glu Gly Ala
                100                 105                 110

Thr Asn Pro Ser Arg Asn Leu Thr Thr Lys Gly Asp Lys His Gln Thr
            115                 120                 125

Thr Arg Ala Thr Thr Glu Ala Glu Leu Glu Lys Gln Ser Lys Gln Thr
            130                 135                 140

Thr Glu Pro Gly Thr Ser Thr Gln Lys His Thr Pro Thr Arg Pro Ser
145                 150                 155                 160

Ser Lys Ser Pro Thr Thr Thr Gln Ala Ile Ala Gln Leu Thr Thr Pro
                165                 170                 175

Thr Thr Pro Lys Ala Ser Thr Ala Pro Lys Asn Arg Gln Ala Thr Thr
            180                 185                 190

Lys Lys Thr Glu Thr Asp Thr Thr Ala Ser Arg Ala Arg Asn Thr
            195                 200                 205

Asn Asn Pro Thr Glu Thr Ala Thr Thr Pro Lys Ala Thr Thr Glu
210                 215                 220

Thr Gly Lys Ser Lys Glu Gly Pro Thr Gln His Thr Thr Lys Glu Gln
225                 230                 235                 240

Pro Glu Thr Thr Ala Gly Glu Thr Thr Pro Gln Pro Arg Arg Thr
                245                 250                 255

Ala Ser Arg Pro Ala Pro Thr Thr Lys Ile Glu Glu Ala Glu Thr
            260                 265                 270

Thr Lys Thr Arg Thr Thr Lys Ser Thr Gln Thr Ser Thr Gly Pro Pro
            275                 280                 285

Arg Pro Thr Gly Gly Ala Pro Ser Gly Ala Ala Thr Glu Gly Ser Gly
290                 295                 300

Arg Ala Ala Ala Ala Gly Gly Pro Ser Ala Ala Ser Ala Gly Gly Arg
305                 310                 315                 320

Arg Arg Thr Glu Ala Ala Glu Arg Asp Arg Thr Arg Ala Gly
                325                 330                 335

Ala Gly Pro Thr Ala Gly Gly Ala Arg Ala Arg Thr Ala Ala Ala Ser
            340                 345                 350

Glu Arg Gly Ala Asp Thr Ala Gly Ser Ala Gly Gly Pro Gly Gly
            355                 360                 365

Asp Gly Ala Thr Gly Gly Leu Ser Gly Gly Ala Pro Ala Glu Arg Glu
    370                 375                 380

Asp Ala Ser Gly Gly Thr Ala Ala Gly Pro Gly Asp Gly Thr Glu
385                 390                 395                 400

Ala Asp Gly Arg Ala Pro Pro Ala Ala Leu Ala Gly Arg Thr Thr
                405                 410                 415

Glu Ser Ala Ala Gly Ala Ala Gly Asp Ser Gly Arg Ala Gly Thr Ala
                420                 425                 430

Gly Trp Gly Ser Ala Ala Asp Gly Arg Ser Thr Gly Gly Asn Ala Ala
            435                 440                 445

Ala Glu Ala Gly Ala Ala Gln Ser Gly Arg Ala Ala Pro Arg Gln Pro
450                 455                 460
```

```
Ser Gly Gly Thr Ala Pro Glu Ser Thr Ala Pro Pro Asn Ser Gly Gly
465                 470                 475                 480

Ser Gly Arg Ala Asp Ala Ala Pro Thr Glu Glu Val Gly Val Gly Ser
                    485                 490                 495

Gly Leu Trp Arg Gly Arg Tyr Val Cys Gly Pro Cys Gly Glu Ser Val
                500                 505                 510

Pro Glu His Pro Met Asn Pro Cys Phe Gly Asp Gly Thr Ala Trp Ile
            515                 520                 525

Cys Ser Asp Asp Gly Gly Ser Leu Pro Ala Gly Cys Tyr Asp Gly Gly
        530                 535                 540

Thr Asp Gly Val Val Cys Gly Val Cys Gly Asn Ser Cys Cys
545                 550                 555                 560

Cys Gly Arg Val Glu Cys Thr Cys Gly Gly Ala Gly Leu Leu Ser
                565                 570                 575

Cys Cys Cys Gly Ser Tyr Ser Trp Ser
            580                 585

<210> SEQ ID NO 57
<211> LENGTH: 585
<212> TYPE: PRT
<213> ORGANISM: Avian pneumovirus

<400> SEQUENCE: 57

Met Glu Val Lys Val Glu Asn Val Gly Lys Ser Gln Glu Leu Lys Val
1               5                   10                  15

Lys Val Lys Asn Phe Ile Lys Arg Ser Asp Cys Lys Lys Lys Leu Phe
                20                  25                  30

Ala Leu Ile Leu Gly Leu Val Ser Phe Glu Leu Thr Met Asn Ile Met
            35                  40                  45

Leu Ser Val Met Tyr Val Glu Ser Asn Glu Ala Leu Ser Leu Cys Arg
        50                  55                  60

Ile Gln Gly Thr Pro Ala Pro Arg Asp Asn Lys Thr Asn Thr Glu Asn
65                  70                  75                  80

Ala Thr Lys Glu Thr Thr Leu His Thr Thr Thr Thr Arg Asp Pro
                85                  90                  95

Glu Val Arg Glu Thr Lys Thr Thr Lys Pro Gln Ala Asn Glu Gly Ala
                100                 105                 110

Thr Asn Pro Ser Arg Asn Leu Thr Thr Lys Gly Asp Lys His Gln Thr
            115                 120                 125

Thr Arg Ala Thr Thr Glu Ala Glu Leu Glu Lys Gln Ser Lys Gln Thr
        130                 135                 140

Thr Glu Pro Gly Thr Ser Thr Gln Lys His Thr Pro Thr Arg Pro Ser
145                 150                 155                 160

Ser Lys Ser Pro Thr Thr Thr Gln Ala Ile Ala Gln Leu Thr Thr Pro
                165                 170                 175

Thr Thr Pro Lys Ala Ser Thr Ala Pro Lys Asn Arg Gln Ala Thr Thr
            180                 185                 190

Lys Lys Thr Glu Thr Asp Thr Thr Ala Ser Arg Ala Arg Asn Thr
        195                 200                 205

Asp Ser Pro Thr Gly Thr Ala Thr Ala Thr Pro Lys Ala Ala Ala Glu
    210                 215                 220

Ala Gly Lys Ser Lys Glu Gly Pro Thr Gln His Thr Thr Lys Glu Gln
225                 230                 235                 240

Pro Gly Ala Thr Ala Gly Glu Thr Ala Thr Pro Gln Pro Arg Arg Thr
                245                 250                 255
```

```
Ala Ser Arg Pro Ala Pro Thr Thr Lys Ile Glu Glu Ala Glu Thr
            260                 265                 270

Thr Lys Thr Arg Thr Thr Lys Ser Thr Gln Thr Ser Thr Gly Pro Pro
        275                 280                 285

Arg Pro Thr Gly Gly Ala Pro Ser Gly Ala Ala Thr Glu Gly Ser Gly
        290                 295                 300

Arg Ala Ala Ala Gly Gly Pro Ser Ala Ala Ser Ala Gly Gly Arg
305                 310                 315                 320

Arg Arg Thr Glu Ala Ala Glu Arg Asp Arg Arg Thr Arg Ala Gly
                325                 330                 335

Ala Gly Pro Thr Ala Gly Gly Arg Ala Arg Thr Ala Ala Ser
        340                 345                 350

Glu Arg Gly Ala Asp Thr Ala Gly Ser Ala Gly Gly Pro Gly Gly
        355                 360                 365

Asp Gly Ala Thr Gly Gly Leu Ser Gly Gly Ala Pro Ala Glu Arg Gly
        370                 375                 380

Asp Ala Ser Gly Gly Thr Ala Ala Ala Gly Pro Gly Asp Gly Thr Glu
385                 390                 395                 400

Ala Asp Gly Arg Ala Pro Ala Ala Ala Leu Ala Gly Arg Thr Thr
                405                 410                 415

Glu Ser Ala Ala Gly Ala Ala Gly Asp Ser Gly Arg Ala Gly Thr Ala
                420                 425                 430

Gly Trp Gly Ser Ala Ala Asp Gly Arg Ser Thr Gly Gly Asn Ala Ala
        435                 440                 445

Ala Glu Ala Gly Ala Ala Gln Ser Gly Arg Ala Ala Pro Arg Gln Pro
    450                 455                 460

Ser Gly Gly Thr Ala Pro Glu Ser Thr Ala Pro Pro Asn Ser Gly Gly
465                 470                 475                 480

Ser Gly Arg Ala Asp Ala Ala Pro Thr Glu Glu Val Gly Val Gly Ser
                485                 490                 495

Gly Leu Trp Arg Gly Arg Tyr Val Cys Gly Pro Cys Gly Glu Ser Val
        500                 505                 510

Pro Glu His Pro Met Asn Pro Cys Phe Gly Asp Gly Thr Ala Trp Ile
    515                 520                 525

Cys Ser Asp Asp Gly Gly Ser Leu Pro Ala Gly Cys Tyr Asp Gly Gly
530                 535                 540

Thr Asp Gly Val Val Cys Cys Gly Val Cys Gly Gly Asn Ser Cys Cys
545                 550                 555                 560

Cys Gly Arg Val Glu Cys Thr Cys Gly Gly Ala Gly Leu Leu Ser
                565                 570                 575

Cys Cys Cys Gly Ser Tyr Ser Trp Ser
            580                 585

<210> SEQ ID NO 58
<211> LENGTH: 585
<212> TYPE: PRT
<213> ORGANISM: Avian pneumovirus

<400> SEQUENCE: 58

Met Glu Val Lys Val Glu Asn Val Gly Lys Ser Gln Glu Leu Lys Val
1               5                   10                  15

Lys Val Lys Asn Phe Ile Lys Arg Ser Asp Cys Lys Lys Lys Leu Phe
            20                  25                  30

Ala Leu Ile Leu Gly Leu Val Ser Phe Glu Leu Thr Met Asn Ile Met
```

-continued

```
                35                  40                  45
Leu Ser Val Met Tyr Val Glu Ser Asn Glu Ala Leu Ser Leu Cys Arg
 50                  55                  60
Ile Gln Gly Thr Pro Ala Pro Arg Asp Asn Lys Thr Asn Thr Glu Asn
 65                  70                  75                  80
Ala Thr Lys Glu Thr Thr Leu His Thr Thr Thr Thr Arg Asp Pro
                 85                  90                  95
Glu Val Arg Glu Thr Lys Thr Thr Lys Pro Gln Ala Asn Glu Gly Ala
                100                 105                 110
Thr Asn Pro Ser Arg Asn Leu Thr Thr Lys Gly Asp Lys His Gln Thr
                115                 120                 125
Thr Arg Ala Thr Thr Glu Ala Glu Leu Glu Lys Gln Ser Lys Gln Thr
                130                 135                 140
Thr Glu Pro Gly Thr Ser Thr Gln Lys His Thr Pro Ala Arg Pro Ser
145                 150                 155                 160
Ser Lys Ser Pro Thr Thr Thr Gln Ala Thr Ala Gln Pro Thr Thr Pro
                165                 170                 175
Thr Ala Pro Lys Ala Ser Thr Ala Pro Lys Asn Arg Gln Ala Thr Thr
                180                 185                 190
Lys Lys Thr Glu Thr Asp Thr Thr Ala Ser Arg Ala Arg Asn Thr
                195                 200                 205
Asn Asn Pro Thr Glu Thr Ala Thr Thr Pro Lys Ala Thr Thr Glu
210                 215                 220
Thr Gly Lys Gly Lys Glu Gly Pro Thr Gln His Thr Lys Glu Gln
225                 230                 235                 240
Pro Glu Thr Thr Ala Arg Glu Thr Thr Thr Pro Gln Pro Arg Arg Thr
                245                 250                 255
Ala Ser Arg Pro Ala Pro Thr Thr Lys Ile Glu Glu Ala Glu Thr
                260                 265                 270
Thr Lys Thr Arg Thr Thr Lys Asn Thr Gln Thr Ser Thr Gly Pro Pro
                275                 280                 285
Arg Pro Thr Arg Ser Thr Pro Ser Lys Thr Ala Thr Glu Asn Asn Lys
                290                 295                 300
Arg Thr Thr Thr Thr Lys Arg Pro Asn Thr Ala Ser Thr Asp Ser Arg
305                 310                 315                 320
Gln Gln Thr Arg Ile Thr Ala Glu Gln Asp Gln Thr Gln Thr Arg
                325                 330                 335
Ala Lys Pro Thr Thr Asn Gly Ala His Pro Gln Thr Thr Thr Thr Pro
                340                 345                 350
Glu His Asn Thr Asp Thr Thr Asn Ser Thr Lys Gly Ser Pro Lys Glu
                355                 360                 365
Asp Lys Thr Thr Arg Asp Pro Ser Ser Lys Thr Pro Thr Glu Gln Glu
                370                 375                 380
Asp Ala Ser Lys Gly Thr Ala Ala Asn Pro Gly Gly Ser Ala Glu
385                 390                 395                 400
Ala Asp Arg Arg Ala Pro Pro Ala Thr Thr Pro Thr Gly Arg Thr Thr
                405                 410                 415
Glu Ser Ala Ala Gly Thr Thr Gly Asp Asp Ser Gly Ala Glu Thr Thr
                420                 425                 430
Arg Arg Arg Ser Ala Ala Asp Arg Arg Ser Thr Gly Gly Ser Thr Ala
                435                 440                 445
Ala Glu Ala Gly Thr Ala Gln Ser Gly Arg Ala Thr Pro Lys Gln Pro
450                 455                 460
```

```
Ser Gly Gly Thr Ala Ala Gly Asn Thr Ala Pro Pro Asn Asn Glu Ser
465                 470                 475                 480

Ser Gly Arg Ala Asp Ala Ala Pro Ala Glu Glu Val Gly Val Gly Ser
                485                 490                 495

Ser Ile Trp Arg Gly Arg Tyr Val Cys Gly Pro Cys Arg Glu Ser Val
            500                 505                 510

Leu Glu His Pro Met Asn Pro Cys Phe Gly Asp Gly Thr Ala Trp Ile
        515                 520                 525

Cys Ser Asp Gly Gly Asn Leu Pro Ala Gly Cys Tyr Asp Ser Gly
    530                 535                 540

Ala Asp Gly Val Val Cys Cys Gly Ile Cys Gly Asn Ser Cys Cys
545                 550                 555                 560

Cys Gly Arg Val Glu Cys Thr Cys Gly Gly Ala Gly Leu Leu Ser
                565                 570                 575

Cys Cys Cys Gly Ser Tyr Asn Trp Ser
            580                 585

<210> SEQ ID NO 59
<211> LENGTH: 21
<212> TYPE: DNA
<213> ORGANISM: Avian pneumovirus

<400> SEQUENCE: 59
gggacaagtg aaaatgtctc t                                       21

<210> SEQ ID NO 60
<211> LENGTH: 18
<212> TYPE: DNA
<213> ORGANISM: Avian pneumovirus

<400> SEQUENCE: 60
ttatgagtaa ttaaaaaa                                           18

<210> SEQ ID NO 61
<211> LENGTH: 21
<212> TYPE: DNA
<213> ORGANISM: Avian pneumovirus

<400> SEQUENCE: 61
gggacaagtc aaaatgtcct t                                       21

<210> SEQ ID NO 62
<211> LENGTH: 18
<212> TYPE: DNA
<213> ORGANISM: Avian pneumovirus

<400> SEQUENCE: 62
tatgtagtta ataaaaaa                                           18

<210> SEQ ID NO 63
<211> LENGTH: 21
<212> TYPE: DNA
<213> ORGANISM: Avian pneumovirus

<400> SEQUENCE: 63
gggacaagtg gaaatggagt c                                       21

<210> SEQ ID NO 64
<211> LENGTH: 18
<212> TYPE: DNA
```

<210> SEQ ID NO 64
<211> LENGTH: 18
<212> TYPE: DNA
<213> ORGANISM: Avian pneumovirus

<400> SEQUENCE: 64
gatattattt agaaaaaa                                                 18

<210> SEQ ID NO 65
<211> LENGTH: 21
<212> TYPE: DNA
<213> ORGANISM: Avian pneumovirus

<400> SEQUENCE: 65
gggacaagtg aaaatgtctt g                                             21

<210> SEQ ID NO 66
<211> LENGTH: 18
<212> TYPE: DNA
<213> ORGANISM: Avian pneumovirus

<400> SEQUENCE: 66
attttagtta ctaaaaaa                                                 18

<210> SEQ ID NO 67
<211> LENGTH: 21
<212> TYPE: DNA
<213> ORGANISM: Avian pneumovirus

<400> SEQUENCE: 67
gggacaagtg aagatgtctc g                                             21

<210> SEQ ID NO 68
<211> LENGTH: 19
<212> TYPE: DNA
<213> ORGANISM: Avian pneumovirus

<400> SEQUENCE: 68
ttctaagtta ataaaaaaa                                                19

<210> SEQ ID NO 69
<211> LENGTH: 21
<212> TYPE: DNA
<213> ORGANISM: Avian pneumovirus

<400> SEQUENCE: 69
gggacaagtc aacatggagc c                                             21

<210> SEQ ID NO 70
<211> LENGTH: 18
<212> TYPE: DNA
<213> ORGANISM: Avian pneumovirus

<400> SEQUENCE: 70
tttttagtta tttaaaaa                                                 18

<210> SEQ ID NO 71
<211> LENGTH: 91
<212> TYPE: DNA
<213> ORGANISM: Avian pneumovirus
<220> FEATURE:
<221> NAME/KEY: misc_feature
<222> LOCATION: (6)..(86)
<223> OTHER INFORMATION: n is a, c, g, or t

<400> SEQUENCE: 71
tcatgnnnnn nnnnnnnnnn nnnnnnnnnn nnnnnnnnnn nnnnnnnnnn nnnnnnnnnn    60

-continued nnnnnnnnnn nnnnnnnnnn nnnnnnaaaa c            91

<210> SEQ ID NO 72
<211> LENGTH: 21
<212> TYPE: DNA
<213> ORGANISM: Avian pneumovirus

<400> SEQUENCE: 72
gggacaagtc aacatggagg t            21

<210> SEQ ID NO 73
<211> LENGTH: 18
<212> TYPE: DNA
<213> ORGANISM: Avian pneumovirus

<400> SEQUENCE: 73
aagttagtta attaaaaa            18

<210> SEQ ID NO 74
<211> LENGTH: 22
<212> TYPE: DNA
<213> ORGANISM: Avian pneumovirus

<400> SEQUENCE: 74
ggaccaagtt aaaaatggat cc            22

<210> SEQ ID NO 75
<211> LENGTH: 18
<212> TYPE: DNA
<213> ORGANISM: Avian pneumovirus

<400> SEQUENCE: 75
caattagtta tttaaaaa            18

<210> SEQ ID NO 76
<211> LENGTH: 14
<212> TYPE: DNA
<213> ORGANISM: Avian pneumovirus
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t

<400> SEQUENCE: 76
tagttantna aaaa            14

<210> SEQ ID NO 77
<211> LENGTH: 16
<212> TYPE: DNA
<213> ORGANISM: Avian pneumovirus
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 77
gggacaagtn aanatg            16

<210> SEQ ID NO 78
<211> LENGTH: 39
<212> TYPE: DNA
<213> ORGANISM: Avian pneumovirus

<400> SEQUENCE: 78
tgaggaacta aaattggatg aatacggttt ttttgccgt                    39

<210> SEQ ID NO 79
<211> LENGTH: 20
<212> TYPE: DNA
<213> ORGANISM: Avian pneumovirus

<400> SEQUENCE: 79
ggaggacgag aaaaaaacgc                                         20

<210> SEQ ID NO 80
<211> LENGTH: 24
<212> TYPE: DNA
<213> ORGANISM: Avian pneumovirus

<400> SEQUENCE: 80
gattgttgat gccagcttcg tgaa                                    24

<210> SEQ ID NO 81
<211> LENGTH: 26
<212> TYPE: DNA
<213> ORGANISM: Avian pneumovirus

<400> SEQUENCE: 81
gttggaggca gcagggtcat agaatc                                  26

<210> SEQ ID NO 82
<211> LENGTH: 23
<212> TYPE: DNA
<213> ORGANISM: Avian pneumovirus

<400> SEQUENCE: 82
ggaggacgag aaaaaaaccg tat                                     23

<210> SEQ ID NO 83
<211> LENGTH: 20
<212> TYPE: DNA
<213> ORGANISM: Avian pneumovirus

<400> SEQUENCE: 83
cagtgccgtc cccaaaacat                                         20

<210> SEQ ID NO 84
<211> LENGTH: 20
<212> TYPE: DNA
<213> ORGANISM: Avian pneumovirus

<400> SEQUENCE: 84
catcatagca accagccggc                                         20

<210> SEQ ID NO 85
<211> LENGTH: 9
<212> TYPE: RNA
<213> ORGANISM: Avian pneumovirus

<400> SEQUENCE: 85 gggacaagu                                                      9

<210> SEQ ID NO 86
<211> LENGTH: 14
<212> TYPE: RNA
<213> ORGANISM: Avian pneumovirus

<400> SEQUENCE: 86
uaguuaauua aaaa                                                        14

<210> SEQ ID NO 87
<211> LENGTH: 623
<212> TYPE: DNA
<213> ORGANISM: Avian pneumovirus
<220> FEATURE:
<221> NAME/KEY: CDS
<222> LOCATION: (14)..(541)

<400> SEQUENCE: 87

```
gggacaagtc aac atg gag ccc ctg aaa gtc tct gga agt gga ggg ata           49
           Met Glu Pro Leu Lys Val Ser Gly Ser Gly Gly Ile
             1               5                  10 ccg atg aag aca agg ctt aat atc ata ctt gag aag tca atc aat aaa          97
Pro Met Lys Thr Arg Leu Asn Ile Ile Leu Glu Lys Ser Ile Asn Lys
         15                  20                  25 atc ttg atc att tta gga tta cta tta act gcc tca act gta att aca         145
Ile Leu Ile Ile Leu Gly Leu Leu Leu Thr Ala Ser Thr Val Ile Thr
 30                  35                  40 atc aca ctc aca gtg gag tat ata aga gta gaa aat gaa ttg caa ctt         193
Ile Thr Leu Thr Val Glu Tyr Ile Arg Val Glu Asn Glu Leu Gln Leu
 45                  50                  55                  60 tgc aag atg gaa gca gag gtg gcc aag aca act ccg gaa cca cca aca         241
Cys Lys Met Glu Ala Glu Val Ala Lys Thr Thr Pro Glu Pro Pro Thr
                 65                  70                  75 cag cca acg aag aca act cct aca cta acc aga acc aga tca acc acc         289
Gln Pro Thr Lys Thr Thr Pro Thr Leu Thr Arg Thr Arg Ser Thr Thr
             80                  85                  90 gca tcc ctc aaa acc aga cca gtt tca agg acc act cat ccc acc aat         337
Ala Ser Leu Lys Thr Arg Pro Val Ser Arg Thr Thr His Pro Thr Asn
         95                 100                 105 ccc agc tgc tgg aga gag gag gaa aag tgc cag aat atc aca gct aaa         385
Pro Ser Cys Trp Arg Glu Glu Glu Lys Cys Gln Asn Ile Thr Ala Lys
    110                 115                 120 tgg tcc aat tgt ttt ggc aca tct cta cct gtg agg gtg aac tgc acg         433
Trp Ser Asn Cys Phe Gly Thr Ser Leu Pro Val Arg Val Asn Cys Thr
125                 130                 135                 140 gta cta aga gaa ttg tgt gat gag cag cca ggc aat cac aca aca gtt         481
Val Leu Arg Glu Leu Cys Asp Glu Gln Pro Gly Asn His Thr Thr Val
                145                 150                 155 caa gta tca agg agg tgt aca tgc ata tat gca tta aat tgg gat tgt         529
Gln Val Ser Arg Arg Cys Thr Cys Ile Tyr Ala Leu Asn Trp Asp Cys
            160                 165                 170 agt tat gct tga gagagagact acactagccg accctaatga ggtccacaga             581
Ser Tyr Ala
        175 aaaagattaa aagcataaac caatttttta gttatttaaa aa                          623
```

<210> SEQ ID NO 88
<211> LENGTH: 175
<212> TYPE: PRT
<213> ORGANISM: Avian pneumovirus

<400> SEQUENCE: 88

```
Met Glu Pro Leu Lys Val Ser Gly Ser Gly Gly Ile Pro Met Lys Thr
1               5                   10                  15

Arg Leu Asn Ile Ile Leu Glu Lys Ser Ile Asn Lys Ile Leu Ile Ile
            20                  25                  30

Leu Gly Leu Leu Leu Thr Ala Ser Thr Val Ile Thr Ile Thr Leu Thr
        35                  40                  45

Val Glu Tyr Ile Arg Val Glu Asn Glu Leu Gln Leu Cys Lys Met Glu
50                  55                  60

Ala Glu Val Ala Lys Thr Thr Pro Glu Pro Pro Thr Gln Pro Thr Lys
65                  70                  75                  80

Thr Thr Pro Thr Leu Thr Arg Thr Arg Ser Thr Thr Ala Ser Leu Lys
            85                  90                  95

Thr Arg Pro Val Ser Arg Thr Thr His Pro Thr Asn Pro Ser Cys Trp
            100                 105                 110

Arg Glu Glu Glu Lys Cys Gln Asn Ile Thr Ala Lys Trp Ser Asn Cys
        115                 120                 125

Phe Gly Thr Ser Leu Pro Val Arg Val Asn Cys Thr Val Leu Arg Glu
    130                 135                 140

Leu Cys Asp Glu Gln Pro Gly Asn His Thr Thr Val Gln Val Ser Arg
145                 150                 155                 160

Arg Cys Thr Cys Ile Tyr Ala Leu Asn Trp Asp Cys Ser Tyr Ala
                165                 170                 175

<210> SEQ ID NO 89
<211> LENGTH: 528
<212> TYPE: DNA
<213> ORGANISM: Avian pneumovirus
<220> FEATURE:
<221> NAME/KEY: CDS
<222> LOCATION: (1)..(528)

<400> SEQUENCE: 89 atg gag

```
                130                 135                 140
ttg tgt gat gag cag cca ggc aat cac aca aca gtt caa gta tca agg      480
Leu Cys Asp Glu Gln Pro Gly Asn His Thr Thr Val Gln Val Ser Arg
145                 150                 155                 160 agg tgt aca tgc ata tat gca tta aat tgg gat tgt agt tat gct tga      528
Arg Cys Thr Cys Ile Tyr Ala Leu Asn Trp Asp Cys Ser Tyr Ala
                165                 170                 175
```

<210> SEQ ID NO 90
<211> LENGTH: 175
<212> TYPE: PRT
<213> ORGANISM: Avian pneumovirus

<400> SEQUENCE: 90

```
Met Glu Pro Leu Lys Val Ser Gly Ser Gly Gly Ile Pro Met Lys Thr
1               5                   10                  15

Arg Leu Asn Ile Ile Leu Glu Lys Ser Ile Asn Lys Ile Leu Ile Ile
            20                  25                  30

Leu Gly Leu Leu Leu Thr Ala Ser Thr Val Ile Thr Ile Thr Leu Thr
        35                  40                  45

Val Glu Tyr Ile Arg Val Glu Asn Glu Leu Gln Leu Cys Lys Met Glu
    50                  55                  60

Ala Glu Val Ala Lys Thr Thr Pro Glu Pro Pro Thr Gln Pro Thr Lys
65                  70                  75                  80

Thr Thr Pro Thr Leu Thr Arg Thr Arg Ser Thr Thr Ala Ser Leu Lys
                85                  90                  95

Thr Arg Pro Val Ser Arg Thr Thr His Pro Thr Asn Pro Ser Cys Trp
            100                 105                 110

Arg Glu Glu Lys Cys Gln Asn Ile Thr Ala Lys Trp Ser Asn Cys
        115                 120                 125

Phe Gly Thr Ser Leu Pro Val Arg Val Asn Cys Thr Val Leu Arg Glu
    130                 135                 140

Leu Cys Asp Glu Gln Pro Gly Asn His Thr Thr Val Gln Val Ser Arg
145                 150                 155                 160

Arg Cys Thr Cys Ile Tyr Ala Leu Asn Trp Asp Cys Ser Tyr Ala
                165                 170                 175
```

<210> SEQ ID NO 91
<211> LENGTH: 528
<212> TYPE: DNA
<213> ORGANISM: Avian pneumovirus
<220> FEATURE:
<221> NAME/KEY: CDS
<222> LOCATION: (1)..(528)

<400> SEQUENCE: 91

```
atg gag ccc ctg aaa gtc tct gga agt gga ggg ata ccg atg aag aca      48
Met Glu Pro Leu Lys Val Ser Gly Ser Gly Gly Ile Pro Met Lys Thr
1               5                   10                  15 agg ctt aat atc ata ctt gag aag tca atc aat aaa atc ttg atc att      96
Arg Leu Asn Ile Ile Leu Glu Lys Ser Ile Asn Lys Ile Leu Ile Ile
            20                  25                  30 tta gga tta cta tta act gcc tca act gta att aca atc aca ctc aca      144
Leu Gly Leu Leu Leu Thr Ala Ser Thr Val Ile Thr Ile Thr Leu Thr
        35                  40                  45 gtg gag tat ata aga gta gaa aat gaa ttg cta ctt tgc aag atg gga      192
Val Glu Tyr Ile Arg Val Glu Asn Glu Leu Leu Leu Cys Lys Met Gly
    50                  55                  60 gca gag gtg gcc aag aca act ccg gaa cca cca aca cag cca acg aag      240
```

```
Ala Glu Val Ala Lys Thr Thr Pro Glu Pro Pro Thr Gln Pro Thr Lys
 65                  70                  75                  80 aca act cct aca cta acc aga acc aga tca acc acc gca tcc ctc aaa    288
Thr Thr Pro Thr Leu Thr Arg Thr Arg Ser Thr Thr Ala Ser Leu Lys
                 85                  90                  95 acc aga cca gtt tca agg acc act cat ccc acc aat ccc agc tgc tgg    336
Thr Arg Pro Val Ser Arg Thr Thr His Pro Thr Asn Pro Ser Cys Trp
            100                 105                 110 aga gag gag gaa aag tgc cag aat atc aca gct aaa tgg tcc aat tgt    384
Arg Glu Glu Glu Lys Cys Gln Asn Ile Thr Ala Lys Trp Ser Asn Cys
        115                 120                 125 ttt ggc aca tct cta cct gtg agg gtg aac tgc acg gta cta aga gaa    432
Phe Gly Thr Ser Leu Pro Val Arg Val Asn Cys Thr Val Leu Arg Glu
    130                 135                 140 ttg tgt gat gag cag cca ggc aat cac aca aca gtt caa gta tca agg    480
Leu Cys Asp Glu Gln Pro Gly Asn His Thr Thr Val Gln Val Ser Arg
145                 150                 155                 160 agg tgt aca tgc ata tat gca tta aat tgg gat tgt agt cat gct tga    528
Arg Cys Thr Cys Ile Tyr Ala Leu Asn Trp Asp Cys Ser His Ala
                165                 170                 175

<210> SEQ ID NO 92
<211> LENGTH: 175
<212> TYPE: PRT
<213> ORGANISM: Avian pneumovirus

<400> SEQUENCE: 92

Met Glu Pro Leu Lys Val Ser Gly Ser Gly Gly Ile Pro Met Lys Thr
  1               5                  10                  15

Arg Leu Asn Ile Ile Leu Glu Lys Ser Ile Asn Lys Ile Leu Ile Ile
             20                  25                  30

Leu Gly Leu Leu Leu Thr Ala Ser Thr Val Ile Thr Ile Thr Leu Thr
         35                  40                  45

Val Glu Tyr Ile Arg Val Glu Asn Glu Leu Leu Leu Cys Lys Met Gly
     50                  55                  60

Ala Glu Val Ala Lys Thr Thr Pro Glu Pro Pro Thr Gln Pro Thr Lys
 65                  70                  75                  80

Thr Thr Pro Thr Leu Thr Arg Thr Arg Ser Thr Thr Ala Ser Leu Lys
                 85                  90                  95

Thr Arg Pro Val Ser Arg Thr Thr His Pro Thr Asn Pro Ser Cys Trp
            100                 105                 110

Arg Glu Glu Glu Lys Cys Gln Asn Ile Thr Ala Lys Trp Ser Asn Cys
        115                 120                 125

Phe Gly Thr Ser Leu Pro Val Arg Val Asn Cys Thr Val Leu Arg Glu
    130                 135                 140

Leu Cys Asp Glu Gln Pro Gly Asn His Thr Thr Val Gln Val Ser Arg
145                 150                 155                 160

Arg Cys Thr Cys Ile Tyr Ala Leu Asn Trp Asp Cys Ser His Ala
                165                 170                 175

<210> SEQ ID NO 93
<211> LENGTH: 1798
<212> TYPE: DNA
<213> ORGANISM: Avian pneumovirus
<220> FEATURE:
<221> NAME/KEY: CDS
<222> LOCATION: (14)..(1771)

<400> SEQUENCE: 93
```

-continued

```
gggacaagtc aac atg gag gtc aag gta gag aat gtt ggt aag tca cag        49
            Met Glu Val Lys Val Glu Asn Val Gly Lys Ser Gln
            1               5                   10 gag ctt aaa gtc aaa gtc aag aat ttt ata aaa agg tct gat tgc aag       97
Glu Leu Lys Val Lys Val Lys Asn Phe Ile Lys Arg Ser Asp Cys Lys
        15                  20                  25 aaa aaa ctt ttt gcc ttg att tta ggg cta gtc agc ttt gaa ctc act      145
Lys Lys Leu Phe Ala Leu Ile Leu Gly Leu Val Ser Phe Glu Leu Thr
    30                  35                  40 atg aat ata atg ctg tct gtc atg tat gtg gag tca aat gag gcc cta      193
Met Asn Ile Met Leu Ser Val Met Tyr Val Glu Ser Asn Glu Ala Leu
45                  50                  55                  60 agt tta tgt agg atc caa ggg act cct gct cca agg gat aat aag aca      241
Ser Leu Cys Arg Ile Gln Gly Thr Pro Ala Pro Arg Asp Asn Lys Thr
                65                  70                  75 aac aca gaa aac gca aca aag gaa aca aca ctc cac aca acg acc aca      289
Asn Thr Glu Asn Ala Thr Lys Glu Thr Thr Leu His Thr Thr Thr Thr
            80                  85                  90 aca agg gat cca gag gtg agg gaa aca aaa acc acc aag ccc cag gcc      337
Thr Arg Asp Pro Glu Val Arg Glu Thr Lys Thr Thr Lys Pro Gln Ala
        95                  100                 105 aat gaa gga gca aca aac cca agc agg aac ctc acc acc aag gga gac      385
Asn Glu Gly Ala Thr Asn Pro Ser Arg Asn Leu Thr Thr Lys Gly Asp
    110                 115                 120 aaa cac caa acg aca aga gca aca aca gag gca gaa ctg gaa aaa caa      433
Lys His Gln Thr Thr Arg Ala Thr Thr Glu Ala Glu Leu Glu Lys Gln
125                 130                 135                 140 agc aaa caa acc aca gag cca ggc acc agc acc caa aag cac acc ccc      481
Ser Lys Gln Thr Thr Glu Pro Gly Thr Ser Thr Gln Lys His Thr Pro
                145                 150                 155 aca aga cca agc agc aaa tcc ccc acc aca aca caa gca ata gca caa      529
Thr Arg Pro Ser Ser Lys Ser Pro Thr Thr Thr Gln Ala Ile Ala Gln
            160                 165                 170 ctg aca aca cca aca acc cca aaa gca agc aca gca ccc aag aac aga      577
Leu Thr Thr Pro Thr Thr Pro Lys Ala Ser Thr Ala Pro Lys Asn Arg
        175                 180                 185 cag gca aca acc aaa aaa acc gaa acg gac acc aca aca gca agc aga      625
Gln Ala Thr Thr Lys Lys Thr Glu Thr Asp Thr Thr Thr Ala Ser Arg
    190                 195                 200 gca agg aac acc aac aac ccc aca gag aca gca aca aca act ccc aaa      673
Ala Arg Asn Thr Asn Asn Pro Thr Glu Thr Ala Thr Thr Thr Pro Lys
205                 210                 215                 220 gca aca aca gaa aca ggc aag agc aaa gag ggg cca aca cag cac aca      721
Ala Thr Thr Glu Thr Gly Lys Ser Lys Glu Gly Pro Thr Gln His Thr
                225                 230                 235 acc aaa gaa cag ccc gag aca aca gca gga gag aca aca acc cca cag      769
Thr Lys Glu Gln Pro Glu Thr Thr Ala Gly Glu Thr Thr Thr Pro Gln
            240                 245                 250 cca aga aga aca gcc agc agg cca gcc cca aca aca aaa atc gaa gag      817
Pro Arg Arg Thr Ala Ser Arg Pro Ala Pro Thr Thr Lys Ile Glu Glu
        255                 260                 265 gag gca gaa acc acc aaa acc aga aca acc aaa agc acc caa aca agc      865
Glu Ala Glu Thr Thr Lys Thr Arg Thr Thr Lys Ser Thr Gln Thr Ser
    270                 275                 280 aca ggc cca cca aga cca acg ggg ggc gca ccc agc ggg gca gcg acg      913
Thr Gly Pro Pro Arg Pro Thr Gly Gly Ala Pro Ser Gly Ala Ala Thr
285                 290                 295                 300 gag ggc agc ggg aga gcc gcg gcg ggg ggg ccg agc gcg gcg agc          961
Glu Gly Ser Gly Arg Ala Ala Ala Gly Gly Pro Ser Ala Ala Ser
                305                 310                 315
```

```
gca ggc ggc agg cgg cgg acc gag gca gcc gcg gag cgg gac cgg cgg     1009
Ala Gly Gly Arg Arg Arg Thr Glu Ala Ala Ala Glu Arg Asp Arg Arg
            320                 325                 330 acc cgg gcc ggg gcc ggg ccc acc gca ggt ggg gcc cgc gcg cgg acc     1057
Thr Arg Ala Gly Ala Gly Pro Thr Ala Gly Gly Ala Arg Ala Arg Thr
        335                 340                 345 gcc gcc gcc tcg gag cgc ggc gcg gac acg gcg ggc agc gca ggg ggg     1105
Ala Ala Ala Ser Glu Arg Gly Ala Asp Thr Ala Gly Ser Ala Gly Gly
    350                 355                 360 ggt ccc ggg ggg gac ggg gcg acc gga ggc ctc agc ggc gga gcg ccg     1153
Gly Pro Gly Gly Asp Gly Ala Thr Gly Gly Leu Ser Gly Gly Ala Pro
365                 370                 375                 380 gcc gag cgg gag gac gcc agc ggg ggg acg gcc gcg gcc ggt ccc ggg     1201
Ala Glu Arg Glu Asp Ala Ser Gly Gly Thr Ala Ala Ala Gly Pro Gly
                385                 390                 395 gac ggc acc gag gcg gac ggg agg gcg ccc ccg gcg gcc gcc ctg gcg     1249
Asp Gly Thr Glu Ala Asp Gly Arg Ala Pro Pro Ala Ala Ala Leu Ala
            400                 405                 410 ggg cgc acc acg gag tcg gcc gcg ggc gcg gcg ggg gac agc ggc agg     1297
Gly Arg Thr Thr Glu Ser Ala Ala Gly Ala Ala Gly Asp Ser Gly Arg
        415                 420                 425 gca ggg acc gcg gga tgg ggg agc gca gcg gac gga cgg tcc acg gga     1345
Ala Gly Thr Ala Gly Trp Gly Ser Ala Ala Asp Gly Arg Ser Thr Gly
    430                 435                 440 ggc aac gca gcg gcg gag gcc ggg gca gcc cag agc ggg cgg gcc gcg     1393
Gly Asn Ala Ala Ala Glu Ala Gly Ala Ala Gln Ser Gly Arg Ala Ala
445                 450                 455                 460 ccg agg cag ccg agc ggc ggc acg gca ccg gag agc acc gca cca ccg     1441
Pro Arg Gln Pro Ser Gly Gly Thr Ala Pro Glu Ser Thr Ala Pro Pro
                465                 470                 475 aac agc ggg ggc agc ggt cgg gca gat gcc gca cca aca gag gag gtt     1489
Asn Ser Gly Gly Ser Gly Arg Ala Asp Ala Ala Pro Thr Glu Glu Val
            480                 485                 490 ggg gtc ggc tcg ggc ctc tgg cga ggg aga tat gtt tgt ggg ccc tgc     1537
Gly Val Gly Ser Gly Leu Trp Arg Gly Arg Tyr Val Cys Gly Pro Cys
        495                 500                 505 ggg gag agt gtt ccg gag cat ccg atg aat cca tgt ttt ggg gac ggc     1585
Gly Glu Ser Val Pro Glu His Pro Met Asn Pro Cys Phe Gly Asp Gly
    510                 515                 520 act gca tgg att tgt tcg gat gat ggg ggg agt ttg ccg gct ggt tgc     1633
Thr Ala Trp Ile Cys Ser Asp Asp Gly Gly Ser Leu Pro Ala Gly Cys
525                 530                 535                 540 tat gat ggt gga acg gat gga gtg gtt tgc tgt gga gtt tgt gga ggc     1681
Tyr Asp Gly Gly Thr Asp Gly Val Val Cys Cys Gly Val Cys Gly Gly
                545                 550                 555 aac tcg tgt tgt tgc ggg cga gta gag tgc aca tgt ggg ggt gga gcg     1729
Asn Ser Cys Cys Cys Gly Arg Val Glu Cys Thr Cys Gly Gly Gly Ala
            560                 565                 570 gga ctg cta tcc tgc tgc tgt ggc tca tac agc tgg agt tag             1771
Gly Leu Leu Ser Cys Cys Cys Gly Ser Tyr Ser Trp Ser
        575                 580                 585 tttagaagca agttagttaa ttaaaaa                                       1798

<210> SEQ ID NO 94
<211> LENGTH: 2758
<212> TYPE: DNA
<213> ORGANISM: Avian pneumovirus
<220> FEATURE:
<221> NAME/KEY: CDS
<222> LOCATION: (14)..(1771)
```

<400> SEQUENCE: 94

```
gggacaagtc aac atg gag gtc aag gta gag aat gtt ggt aag tca cag       49
            Met Glu Val Lys Val Glu Asn Val Gly Lys Ser Gln
            1               5                   10 gag ctt aaa gtc aaa gtc aag aat ttt ata aaa agg tct gat tgc aag       97
Glu Leu Lys Val Lys Val Lys Asn Phe Ile Lys Arg Ser Asp Cys Lys
        15                  20                  25 aaa aaa ctt ttt gcc ttg att tta ggg cta gtc agc ttt gaa ctc act      145
Lys Lys Leu Phe Ala Leu Ile Leu Gly Leu Val Ser Phe Glu Leu Thr
        30                  35                  40 atg aat ata atg ctg tct gtc atg tat gtg gag tca aat gag gcc cta      193
Met Asn Ile Met Leu Ser Val Met Tyr Val Glu Ser Asn Glu Ala Leu
45                  50                  55                  60 agt tta tgt agg atc caa ggg act cct gct cca agg gat aat aag aca      241
Ser Leu Cys Arg Ile Gln Gly Thr Pro Ala Pro Arg Asp Asn Lys Thr
                65                  70                  75 aac aca gaa aac gca aca aag gaa aca aca ctc cac aca acg acc aca      289
Asn Thr Glu Asn Ala Thr Lys Glu Thr Thr Leu His Thr Thr Thr Thr
            80                  85                  90 aca agg gat cca gag gtg agg gaa aca aaa acc acc aag ccc cag gcc      337
Thr Arg Asp Pro Glu Val Arg Glu Thr Lys Thr Thr Lys Pro Gln Ala
        95                  100                 105 aat gaa gga gca aca aac cca agc agg aac ctc acc acc aag gga gac      385
Asn Glu Gly Ala Thr Asn Pro Ser Arg Asn Leu Thr Thr Lys Gly Asp
110                 115                 120 aaa cac caa acg aca aga gca aca aca gag gca gaa ctg gaa aaa caa      433
Lys His Gln Thr Thr Arg Ala Thr Thr Glu Ala Glu Leu Glu Lys Gln
125                 130                 135                 140 agc aaa caa acc aca gag cca ggc acc agc acc caa aag cac acc ccc      481
Ser Lys Gln Thr Thr Glu Pro Gly Thr Ser Thr Gln Lys His Thr Pro
                145                 150                 155 aca aga cca agc agc aaa tcc ccc acc aca aca caa gca ata gca caa      529
Thr Arg Pro Ser Ser Lys Ser Pro Thr Thr Thr Gln Ala Ile Ala Gln
            160                 165                 170 ctg aca aca cca aca acc cca aaa gca agc aca gca ccc aag aac aga      577
Leu Thr Thr Pro Thr Thr Pro Lys Ala Ser Thr Ala Pro Lys Asn Arg
        175                 180                 185 cag gca aca acc aaa aaa acc gaa acg gac acc aca aca gca agc aga      625
Gln Ala Thr Thr Lys Lys Thr Glu Thr Asp Thr Thr Thr Ala Ser Arg
        190                 195                 200 gca agg aac acc aac aac ccc aca gag aca gca aca aca act ccc aaa      673
Ala Arg Asn Thr Asn Asn Pro Thr Glu Thr Ala Thr Thr Thr Pro Lys
205                 210                 215                 220 gca aca aca gaa aca ggc aag agc aaa gag ggg cca aca cag cac aca      721
Ala Thr Thr Glu Thr Gly Lys Ser Lys Glu Gly Pro Thr Gln His Thr
                225                 230                 235 acc aaa gaa cag ccc gag aca aca gca gga gag aca aca acc cca cag      769
Thr Lys Glu Gln Pro Glu Thr Thr Ala Gly Glu Thr Thr Thr Pro Gln
        240                 245                 250 cca aga aga aca gcc agc agg cca gcc cca aca aca aaa atc gaa gag      817
Pro Arg Arg Thr Ala Ser Arg Pro Ala Pro Thr Thr Lys Ile Glu Glu
        255                 260                 265 gag gca gaa acc acc aaa acc aga aca acc aaa agc acc caa aca agc      865
Glu Ala Glu Thr Thr Lys Thr Arg Thr Thr Lys Ser Thr Gln Thr Ser
270                 275                 280 aca ggc cca cca aga cca acg ggg ggc gca ccc agc ggg gca gcg acg      913
Thr Gly Pro Pro Arg Pro Thr Gly Gly Ala Pro Ser Gly Ala Ala Thr
285                 290                 295                 300
```

```
gag ggc agc ggg aga gcc gcg gcg gcg ggg ggg ccg agc gcg gcg agg      961
Glu Gly Ser Gly Arg Ala Ala Ala Ala Gly Gly Pro Ser Ala Ala Arg
            305                 310                 315 gga caa gtc aac atg gag gtc aag gta gag aat gtt ggc aag tca cag     1009
Gly Gln Val Asn Met Glu Val Lys Val Glu Asn Val Gly Lys Ser Gln
        320                 325                 330 gag ctt aaa gtc aaa gtc aag aat ttt ata aaa agg tct gat tgc aag     1057
Glu Leu Lys Val Lys Val Lys Asn Phe Ile Lys Arg Ser Asp Cys Lys
    335                 340                 345 aaa aaa ctt ttt gcc ttg att tta ggg cta gtc agc ttt gaa ctc act     1105
Lys Lys Leu Phe Ala Leu Ile Leu Gly Leu Val Ser Phe Glu Leu Thr
350                 355                 360 atg aat ata atg ctg tct gtc atg tat gtg gag tca aat gag gcc cta     1153
Met Asn Ile Met Leu Ser Val Met Tyr Val Glu Ser Asn Glu Ala Leu
365                 370                 375                 380 agt tta tgt agg atc caa ggg act cct gct cca agg gat aat aag aca     1201
Ser Leu Cys Arg Ile Gln Gly Thr Pro Ala Pro Arg Asp Asn Lys Thr
            385                 390                 395 aac aca gaa aac gca aca aag gaa aca aca ctc cac aca acg acc aca     1249
Asn Thr Glu Asn Ala Thr Lys Glu Thr Thr Leu His Thr Thr Thr Thr
        400                 405                 410 aca agg gat cca gag gtg agg gaa aca aaa acc acc aag ccc cag gcc     1297
Thr Arg Asp Pro Glu Val Arg Glu Thr Lys Thr Thr Lys Pro Gln Ala
    415                 420                 425 aat gaa gga gca aca aac cca agc agg aac ctc acc acc aag gga gac     1345
Asn Glu Gly Ala Thr Asn Pro Ser Arg Asn Leu Thr Thr Lys Gly Asp
430                 435                 440 aaa cac caa acg aca aga gca aca aca gag gca gaa ctg gaa aaa caa     1393
Lys His Gln Thr Thr Arg Ala Thr Thr Glu Ala Glu Leu Glu Lys Gln
445                 450                 455                 460 agc aaa caa acc aca gag cca ggc acc agc acc caa aag cac acc ccc     1441
Ser Lys Gln Thr Thr Glu Pro Gly Thr Ser Thr Gln Lys His Thr Pro
            465                 470                 475 aca aga cca agc agc aaa tcc ccc acc aca aca caa gca ata gca caa     1489
Thr Arg Pro Ser Ser Lys Ser Pro Thr Thr Thr Gln Ala Ile Ala Gln
        480                 485                 490 ctg aca aca cca aca acc cca aaa gca agc aca gca ccc aag aac aga     1537
Leu Thr Thr Pro Thr Thr Pro Lys Ala Ser Thr Ala Pro Lys Asn Arg
    495                 500                 505 cag gca aca acc aaa aaa acc gaa acg gac acc aca aca gca agc aga     1585
Gln Ala Thr Thr Lys Lys Thr Glu Thr Asp Thr Thr Thr Ala Ser Arg
510                 515                 520 gca agg aac acc gac agc ccc acg ggg acg gcg acg gca act ccc aag     1633
Ala Arg Asn Thr Asp Ser Pro Thr Gly Thr Ala Thr Ala Thr Pro Lys
525                 530                 535                 540 gcg gca gcg gag gcg ggc aag agc aaa gag ggg cca aca cag cac aca     1681
Ala Ala Ala Glu Ala Gly Lys Ser Lys Glu Gly Pro Thr Gln His Thr
            545                 550                 555 acc aaa gaa cag ccc ggg gca aca gca gga gag aca gca acc cca cag     1729
Thr Lys Glu Gln Pro Gly Ala Thr Ala Gly Glu Thr Ala Thr Pro Gln
        560                 565                 570 cca aga aga aca gcc agc agg cca gcc cca aca aca aaa atc                 1771
Pro Arg Arg Thr Ala Ser Arg Pro Ala Pro Thr Thr Lys Ile
    575                 580                 585 gaagaggagg cagaaaccac caaaaccaga acaaccaaaa gcacccaaac aagcacaggc     1831
ccaccaagac caacgggggg cgcacccagc ggggcagcga cggagggcag cgggagagcc     1891
gcggcggcgg gggggccgag cgcggcgagc gcaggcggca ggcggcggac cgaggcagcc     1951
gcggagcggg accggcggac ccgggccggg gccgggccca ccgcaggtgg ggcccgcgcg     2011
```

```
cggaccgccg ccgcctcgga gcgcggcgcg gacacggcgg gcagcgcagg gggggtccc    2071 gggggggacg gggcgaccgg aggcctcagc ggcggagcgc cggccgagcg ggggacgcc    2131 agcgggggga cggccgcggc cggtcccggg acggcaccg aggcggacgg gagggcgccc    2191
ccggcggccg ccctggcggg gcgcaccacg gagtcggccg cgggcgcggc ggggacagc    2251 ggcagggcag ggaccgcggg atgggggagc gcagcggacg gacggtccac gggaggcaac    2311
gcagcggcgg aggccggggc agcccagagc gggcgggccg cgccgaggca gccgagcggc    2371
ggcacggcac cggagagcac cgcaccaccg aacagcgggg gcagcggtcg ggcagatgcc    2431
gcaccaacag aggaggttgg ggtcggctcg ggcctctggc gagggagata tgtttgtggg    2491
ccctgcgggg agagtgttcc ggagcatccg atgaatccat gttttgggga cggcactgca    2551
tggatttgtt cggatgatgg ggggagtttg ccggctggtt gctatgatgg tggaacggat    2611
ggagtggttt gctgtggagt ttgtggaggc aactcgtgtt gttgcgggcg agtagagtgc    2671
acatgtgggg gtggagcggg actgctatcc tgctgctgtg gctcatacag ctggagttag    2731
tttagaagca agttagttaa ttaaaaa                                        2758

<210> SEQ ID NO 95
<211> LENGTH: 1798
<212> TYPE: DNA
<213> ORGANISM: Avian pneumovirus
<220> FEATURE:
<221> NAME/KEY: CDS
<222> LOCATION: (14)..(1771)

<400> SEQUENCE: 95
gggacaagtc aac atg g

```
Ala Arg Pro Ser Ser Lys Ser Pro Thr Thr Thr Gln Ala Thr Ala Gln
            160                 165                 170 ccg aca aca cca aca gcc cca aaa gca agc aca gcc ccc aag aac aga         577
Pro Thr Thr Pro Thr Ala Pro Lys Ala Ser Thr Ala Pro Lys Asn Arg
        175                 180                 185 cag gca aca acc aaa aaa acc gaa acg gac acc aca aca gca agc aga         625
Gln Ala Thr Thr Lys Lys Thr Glu Thr Asp Thr Thr Thr Ala Ser Arg
        190                 195                 200 gca agg aac acc aac aac ccc aca gag aca gca aca aca act ccc aaa         673
Ala Arg Asn Thr Asn Asn Pro Thr Glu Thr Ala Thr Thr Thr Pro Lys
205                 210                 215                 220 gca aca aca gaa aca ggc aag ggc aaa gag ggg cca aca cag cac aca         721
Ala Thr Thr Glu Thr Gly Lys Gly Lys Glu Gly Pro Thr Gln His Thr
                    225                 230                 235 acc aaa gaa cag ccc gag aca aca gca cga gag aca aca acc cca cag         769
Thr Lys Glu Gln Pro Glu Thr Thr Ala Arg Glu Thr Thr Thr Pro Gln
                240                 245                 250 cca aga aga aca gcc agc agg cca gcc cca aca aca aaa atc gaa gag         817
Pro Arg Arg Thr Ala Ser Arg Pro Ala Pro Thr Thr Lys Ile Glu Glu
            255                 260                 265 gag gca gaa acc acc aaa acc aga aca acc aaa aac acc caa aca agc         865
Glu Ala Glu Thr Thr Lys Thr Arg Thr Thr Lys Asn Thr Gln Thr Ser
270                 275                 280 aca ggc cca cca aga cca aca aga agc aca cca agc aaa aca gcg aca         913
Thr Gly Pro Pro Arg Pro Thr Arg Ser Thr Pro Ser Lys Thr Ala Thr
285                 290                 295                 300 gaa aac aac aag aga acc aca aca aca aag aga ccg aac aca gcg agc         961
Glu Asn Asn Lys Arg Thr Thr Thr Thr Lys Arg Pro Asn Thr Ala Ser
                    305                 310                 315 aca gac agc aga caa cag acc aga ata acc gca gag caa gac caa caa        1009
Thr Asp Ser Arg Gln Gln Thr Arg Ile Thr Ala Glu Gln Asp Gln Gln
                320                 325                 330 acc caa acc agg gcc aaa ccc acc aca aat ggg gcc cac ccg caa acc        1057
Thr Gln Thr Arg Ala Lys Pro Thr Thr Asn Gly Ala His Pro Gln Thr
            335                 340                 345 acc acc acc cca gag cac aac aca gac aca aca aac agc aca aaa gga        1105
Thr Thr Thr Pro Glu His Asn Thr Asp Thr Thr Asn Ser Thr Lys Gly
350                 355                 360 agt ccc aag gag gac aaa acg acc aga gac ccc agc agc aaa aca cca        1153
Ser Pro Lys Glu Asp Lys Thr Thr Arg Asp Pro Ser Ser Lys Thr Pro
365                 370                 375                 380 acc gag caa gag gac gcc agc aag gga acg gcc gcg gcc aac ccc gga        1201
Thr Glu Gln Glu Asp Ala Ser Lys Gly Thr Ala Ala Ala Asn Pro Gly
                    385                 390                 395 ggc agc gcc gag gca gac agg aga gca ccc ccg gca acc acc cca acg        1249
Gly Ser Ala Glu Ala Asp Arg Arg Ala Pro Pro Ala Thr Thr Pro Thr
                400                 405                 410 ggg cgc acc aca gaa tcg gcc gcg ggc aca acg ggg gac gac agc ggg        1297
Gly Arg Thr Thr Glu Ser Ala Ala Gly Thr Thr Gly Asp Asp Ser Gly
            415                 420                 425 gcg gaa acc aca aga cgg aga agc gca gcg gac aga cgg tcc acg ggg        1345
Ala Glu Thr Thr Arg Arg Arg Ser Ala Ala Asp Arg Arg Ser Thr Gly
430                 435                 440 ggc agc aca gca gcg gag gcc ggg aca gcc cag agc gga cgg gcc acg        1393
Gly Ser Thr Ala Ala Glu Ala Gly Thr Ala Gln Ser Gly Arg Ala Thr
445                 450                 455                 460 ccg aag cag ccg agc ggc ggc acg gca gca ggg aac act gca cca ccg        1441
Pro Lys Gln Pro Ser Gly Gly Thr Ala Ala Gly Asn Thr Ala Pro Pro
                    465                 470                 475
```

```
aac aac gaa agc agc ggt cgg gca gat gcc gca cca gca gag gaa gtt    1489
Asn Asn Glu Ser Ser Gly Arg Ala Asp Ala Ala Pro Ala Glu Glu Val
            480                 485                 490 ggg gtc ggc tca agc atc tgg cga ggg aga tat gtt tgt ggg ccc tgc    1537
Gly Val Gly Ser Ser Ile Trp Arg Gly Arg Tyr Val Cys Gly Pro Cys
            495                 500                 505 aga gag agt gtt ctg gag cat ccg atg aat cca tgt ttt ggg gac ggc    1585
Arg Glu Ser Val Leu Glu His Pro Met Asn Pro Cys Phe Gly Asp Gly
            510                 515                 520 act gca tgg att tgt tcg gat ggt gga ggg aat ttg ccg gct ggt tgt    1633
Thr Ala Trp Ile Cys Ser Asp Gly Gly Gly Asn Leu Pro Ala Gly Cys
525                 530                 535                 540 tat gat agt gga gca gat ggg gtg gtt tgc tgt gga att tgt gga ggc    1681
Tyr Asp Ser Gly Ala Asp Gly Val Val Cys Cys Gly Ile Cys Gly Gly
                    545                 550                 555 aac tcg tgt tgt tgc ggg cga gta gag tgc acg tgt ggg ggt gga gcg    1729
Asn Ser Cys Cys Cys Gly Arg Val Glu Cys Thr Cys Gly Gly Gly Ala
                560                 565                 570 gga cta cta tcc tgc tgc tgt ggc tca tac aac tgg agt tag            1771
Gly Leu Leu Ser Cys Cys Cys Gly Ser Tyr Asn Trp Ser
            575                 580                 585 tttaagagca agttagttaa ttaaaaa                                      1798

<210> SEQ ID NO 96
<211> LENGTH: 182
<212> TYPE: PRT
<213> ORGANISM: Avian pneumovirus

<400> SEQUENCE: 96

Met Ile Thr Leu Asp Val Ile Lys Ser Asp Gly Ser Ser Lys Thr Cys
1               5                   10                  15

Thr His Leu Lys Lys Ile Ile Lys Asp His Ser Gly Lys Val Leu Ile
            20                  25                  30

Val Leu Lys Leu Ile Leu Ala Leu Leu Thr Phe Leu Thr Val Thr Ile
        35                  40                  45

Thr Ile Asn Tyr Ile Lys Val Glu Asn Asn Leu Gln Ile Cys Gln Ser
    50                  55                  60

Lys Thr Glu Ser Asp Lys Lys Asp Ser Ser Asn Thr Thr Ser Val
65                  70                  75                  80

Thr Thr Lys Thr Thr Leu Asn His Asp Ile Thr Gln Tyr Phe Lys Ser
                85                  90                  95

Leu Ile Gln Arg Tyr Thr Asn Ser Ala Ile Asn Ser Asp Thr Cys Trp
            100                 105                 110

Lys Ile Asn Arg Asn Gln Cys Thr Asn Ile Thr Thr Tyr Lys Phe Leu
        115                 120                 125

Cys Phe Lys Ser Glu Asp Thr Lys Thr Asn Asn Cys Asp Lys Leu Thr
    130                 135                 140

Asp Leu Cys Arg Asn Lys Pro Lys Pro Ala Val Gly Val Tyr His Ile
145                 150                 155                 160

Val Glu Cys His Cys Ile Tyr Thr Val Lys Trp Lys Cys Tyr His Tyr
                165                 170                 175

Pro Thr Asp Glu Thr Gln
            180

<210> SEQ ID NO 97
<211> LENGTH: 174
<212> TYPE: PRT
<213> ORGANISM: Avian pneumovirus
```

-continued

<400> SEQUENCE: 97

```
Met Thr Ser Thr Val Asn Leu Gly Ser Asp Thr Ala Ser Lys Arg Thr
1               5                   10                  15

Val Ile Lys Ser Arg Cys Asn Ser Cys Cys Arg Ile Leu Val Ser Cys
            20                  25                  30

Val Ala Val Ile Cys Ala Ile Leu Ala Leu Ile Phe Leu Val Ala Thr
        35                  40                  45

Ile Gly Leu Ser Val Lys Leu Ala Phe Thr Val Gln Glu Val His Asn
    50                  55                  60

Cys Lys Gln Lys Leu Ser Gly Ala Ser Thr Thr Thr Ala Ala Ile Tyr
65                  70                  75                  80

Thr Thr Pro Ser Thr Met Ile Glu Ala Leu Gln Thr Asn Gln Leu Lys
                85                  90                  95

Leu Thr Thr Asn Glu Arg Arg Ser Thr Pro Pro Asp Cys Leu Val Glu
            100                 105                 110

Lys Lys Leu Cys Glu Gly Glu Val Arg Tyr Leu Lys Thr Lys Gly Cys
        115                 120                 125

Leu Gly Ala Arg Glu Gly Glu Asp Leu Asn Cys Ile Asp Leu Val Val
    130                 135                 140

Glu Cys Val Gly Lys Pro Cys Gly His Asn Glu Asp Tyr Lys Glu Cys
145                 150                 155                 160

Ile Cys Thr Asn Asn Gly Thr Ala Thr Lys Cys Cys Tyr Asn
                165                 170
```

<210> SEQ ID NO 98
<211> LENGTH: 175
<212> TYPE: PRT
<213> ORGANISM: Avian pneumovirus

<400> SEQUENCE: 98

```
Met Thr Ser Thr Val Asn Leu Gly Ser Ser Thr Ser Ser Arg Trp Thr
1               5                   10                  15

Ile Ala Lys Ser Gln Cys Met Leu Cys Leu Arg Thr Met Met Asn Cys
            20                  25                  30

Ala Val Val Ile Cys Ala Val Leu Val Leu Ile Phe Leu Val Ala Thr
        35                  40                  45

Ile Gly Leu Ser Val Lys Leu Ala Val Thr Ile Lys Glu Arg Asn Thr
    50                  55                  60

Cys Gln Leu Arg Leu Ser Glu Leu Ser Thr Thr Thr Ala Pro Ile Leu
65                  70                  75                  80

Arg Ser Thr Asn Gln Pro Tyr Leu Gly Gly Ser Thr Ser Thr Pro Lys
                85                  90                  95

Leu Thr Thr Val Thr Ser Ile Thr Asp Leu Thr His Gln Cys Pro Gln
            100                 105                 110

Arg Lys Glu Leu Cys Asn Gly Thr Ile Thr Tyr Ile Asn Ser Asp Gly
        115                 120                 125

Cys Leu Asp Glu Lys Glu Gly Glu Ser Ile Asp Cys Ile Glu Leu Ile
    130                 135                 140

Ala Arg Cys Val Glu Thr Leu Cys Asp Pro Asn Pro Asn Tyr Asn His
145                 150                 155                 160

Cys Met Cys Thr Lys Asn Ser Thr Gly Leu Trp Cys Cys Tyr Asn
                165                 170                 175
```

<210> SEQ ID NO 99

-continued

```
<211> LENGTH: 64
<212> TYPE: PRT
<213> ORGANISM: Avian pneumovirus

<400> SEQUENCE: 99

Met Glu Asn Thr Ser Ile Thr Ile Glu Phe Ser Ser Lys Phe Trp Pro
1               5                   10                  15

Tyr Phe Thr Leu Ile His Met Ile Thr Thr Ile Ile Ser Leu Leu Ile
                20                  25                  30

Ile Ile Ser Ile Met Ile Ala Ile Leu Asn Lys Leu Cys Glu Tyr Asn
                35                  40                  45

Val Phe His Asn Lys Thr Phe Glu Leu Pro Arg Ala Arg Val Asn Thr
            50                  55                  60

<210> SEQ ID NO 100
<211> LENGTH: 81
<212> TYPE: PRT
<213> ORGANISM: Avian pneumovirus

<400> SEQUENCE: 100

Met Asn Asn Thr Ser Thr Ile Ile Glu Phe Thr Gly Glu Phe Trp Thr
1               5                   10                  15

Tyr Phe Thr Leu Ala Phe Met Met Leu Thr Ile Gly Phe Phe Phe Ile
                20                  25                  30

Val Thr Ser Leu Val Ala Ala Ile Leu Asn Lys Leu Cys Asp Phe Asn
                35                  40                  45

Asp His His Thr Asn Ser Leu Asp Ile Arg Thr Arg Leu Arg Asn Asp
            50                  55                  60

Thr Gln Leu Ile Thr Arg Ala His Glu Gly Ser Ile Asn Gln Ser Ser
65                  70                  75                  80

Asn

<210> SEQ ID NO 101
<211> LENGTH: 92
<212> TYPE: PRT
<213> ORGANISM: Avian pneumovirus

<400> SEQUENCE: 101

Met Asp Pro Asn Met Thr Ser His Gln Ile Thr Leu Glu Ile Asn Met
1               5                   10                  15

Thr Ser Ser Arg Ile Gly Thr His Thr Thr Pro Ala Pro Thr Ala Pro
                20                  25                  30

Leu Leu Ala Cys Ala Val Ile Asn Thr Val Cys Ala Leu Ile Met Ala
                35                  40                  45

Cys Ser Arg Ser Thr Ala Thr Ser Gly Ile Val Ser Ser Gln Cys
            50                  55                  60

Thr Val His Pro Asn His Pro Pro Ser Tyr Gly Val Asn Val Thr
65                  70                  75                  80

Gly Leu Pro Gly Asn Leu Tyr Ser Arg Asn Thr Thr
                85                  90
```

AVIAN PNEUMOVIRUS GENES, RECOMBINANT AVIAN PNEUMOVIRUSES AND METHODS OF MAKING

This application is a continuation-in-part of international application number PCT/US03/38123 filed Dec. 2, 2003 and claims the benefit of U.S. provisional application No. 60/430,301 filed Dec. 2, 2002, the contents of which are fully incorporated by reference herein.

BACKGROUND OF THE INVENTION

1. Field of the Invention

The invention relates to the fields of immunology and molecular biology.

2. Related Art

Avian pneumovirus (APV), also known as turkey rhinotracheitis virus, was first reported in South Africa in 1978 (Buys & Du Preez, *Turkeys* 28:36 (1980)) and, subsequently, was isolated in Europe, Israel and Asia (Alexander, in Barnes et al., eds., *Diseases of Poultry*, Iowa State University Press, Ames, Iowa (1997), pp. 541-569; Cavanagh and Barett, *Virus Res.* 11:241-256 (1988); Jones et al., *Vet. Rec.* 119:599-600 (1986); McDougall and Cook, *Vet. Rec.* 118:206-207 (1986); Wilding et al., *Vet. Rec.* 118:735 (1986)). The United States was considered free of APV until 1996, when it was isolated for the first time in Colorado from an outbreak of upper respiratory tract disease in turkeys (Cook et al., *Avian Pathol.* 28:607-617 (1999); Kleven, in *Proceedings of the U.S. Animal Health Association* 101$^{st}$ *Annual Meeting*, U.S. Animal Health Association, Washington, D.C. Report of the Committee: transmissible diseases of poultry and other avian species (1997), pp. 486-491). This first isolate was called APV/Colorado (APV/CO). Subsequently, APV infection was reported in turkeys in Minnesota, from which the virus has spread to the neighboring states of North and South Dakota (Goyal et al., North Central Avian Disease Conference, Minneapolis, Minn. (October, 1999); Panigrahy et al., *Avian Dis.* 44:17-22 (2000)). APV has emerged as a major problem for turkey industries in Minnesota. In 1999, 37% of the turkey flocks in Minnesota were positive for APV antibodies, causing economic losses of approximately $15 million per year (Gulati et al., *J. Clin. Microbiol.* 38:4010-4014 (2000)).

APV belongs to the genus *Metapneumovirus* within the subfamily Pneumovirinae of the family Paramyxoviridae (Pringle, *Arch. Virol.* 143:1449-1459 (1998)). The genome of *Metapneumovirus* is a non-segmented, single-stranded, negative-sense RNA with a gene order of 3'-Leader-N-P-M-F-M2-SH-G-L-Trailer-5'. APV was assigned to a new genus because its genome contains eight genes arranged in a different order from the ten genes of members of genus *Pneumovirus*, such as respiratory syncytial virus (RSV) (Collins et al., "Parainfluenza viruses," in *Fields Virology*, Fields et al., eds., Lippincott-Raven, Philadelphia, Pa. (1996), pp. 1205-1241; Ling et al., *J. Gen. Virol.* 73:1709-1715 (1992); Randhawa et al., *J. Virol.* 71:9849-9854 (1997)). The newly discovered human metapneumovirus (hMPV) is the only mammalian virus that has been included tentatively in the genus *Metapneumovirus* (Van den Hoogen et al., *Nat. Med.* 7:719-724 (2001); Van den Hoogen, et al., *Virology* 295:119-132 (2002); Njenga et al., *Virus Res.* 91:163-169 (2003)).

On the basis of level of genetic variation in the attachment (G) protein, European APV isolates have been divided into two subgroups, designated A and B (Juhasz and Easton, *J. Gen Virol.* 75:2873-2880 (1994)). These two subgroups were also shown to be antigenically distinct (Bayon-Auboyer et al., *Arch. Virol.* 144:1091-1109 (1999)). Until late 1996, all known APV isolates belonged to either the A or the B subgroup. Surprisingly, the APV isolates from the U.S. were shown to cross-neutralize poorly with European subgroup A and B viruses, suggesting that they belong to a different subgroup. A new subgroup, C, has been proposed for the U.S. isolates of APV (Cook et al., *Avian Pathol.* 28:607-617 (1998); Kleven, in *Proceedings of the U.S. Animal Health Association* 101$^{st}$ *Annual Meeting*, U.S. Animal Health Association, Washington, D.C. Report of the Committee: transmissible diseases of poultry and other avian species (1997), pp. 486-491; Seal, *Virus Res.* 58:45-52 (1998); Seal, *Health Res. Rev.* 1:67-72 (2000); Shin et al., *J. Clin. Microbiol.* 40:1687-1693 (2002)). Recently, a subgroup D strain of APV has been reported (Bayon-Auboyer et al., *J. Gen. Virol.* 81:2723-2733 (2000)). The U.S. isolates have been shown to be different from Subgroup D strains (Toquin et al., *Avian Dis.* 44:977-982 (2000)).

The nucleotide sequences of all the eight mRNAs of APV subgroup A have been reported (Randhawa et al., *J. Virol.* 71:9849-9854 (1997) and references therein). However, the nucleotide and deduced amino acid sequences of only N, P, M, F and M2 genes of APV/CO have been reported (Dar et al., *Virus Res.* 79 (1-2):15-25 (2001); Seal, *Virus Res.* 58:45-52 (1998); Seal et al., *Virus Res.* 66:139-147 (2000); Genbank accession—AF176592).

At present, there is no satisfactory vaccine available for APV and also no method available to genetically manipulate the genome of APV.

BRIEF SUMMARY OF THE INVENTION

In accordance with the invention, there are provided isolated nucleic acid molecules which are at least 95% identical to the coding region of the SH gene (SEQ ID NO:87) of APV/CO. Further provided are isolated nucleic acid molecules encoding the SH protein (SEQ ID NO:88) of APV/CO. The nucleic acid molecules and polypeptides of the present invention are useful for making immunological formulations against, and in the detection of, APV/CO.

In accordance with another aspect of the invention, there are provided methods of making recombinant APV comprising constructing a cDNA encoding the antigenome of APV, transfecting the cDNA into cells, and culturing the cells under conditions suitable to produce the recombinant APV. Also provided are recombinant APV produced by this method.

In accordance with another aspect, there are provided methods of making a live-attenuated APV and APV produced by this method, comprising: constructing a cDNA encoding the antigenome of APV with one or more attenuating mutations, transfecting the cDNA into cells, and culturing the sells under conditions suitable to produce the recombinant APV. The live-attenuated APVs of the present invention are useful as an immunological formulation.

In accordance with yet another aspect of the invention, there are provided methods of diagnosing APV, comprising detecting APV RNA or protein expression in a biological sample.

BRIEF DESCRIPTION OF THE FIGURES

FIG. 2 shows comparative alignments of genomic termini of APV sequences. Comparative alignment of the nucleotide sequences (genomic-sense) of the 3' leader region is shown in (A) and the 5' trailer region in (B) of APV/CO (SEQ ID NO:1), APV-A (SEQ ID NO:2), and HMPV isolates 00-1

(SEQ ID NO:3), CAN97-83 (SEQ ID NO:47) and CAN98-75 (SEQ ID NO:48). Perfectly conserved nucleotides relative to APV/CO are indicated by dots. Dashes were included in the HMPV 00-1 sequences since they were primer-based. Complementarity between the 3' and 5' ends of APV/CO genomic RNA is shown in (C). The complementary nucleotides are marked by vertical lines.

FIG. 3 shows the confirmation of the gene-order through genome-walk by sequential RT-PCR along APV-genomic RNA: The 3' to 5' order of the genes in the genomic RNA of APV/CO is shown. The transcription-signals gene-start (GS) and semi-conserved gene-end (GE) signals of each gene are indicated. Sequence of intergenic region: M-F (SEQ ID NO:4), F-M2 (SEQ ID NO:5), M2-SH (SEQ ID NO:6) and SH-G (SEQ ID NO:7) are shown in bold italics.

FIG. 4 shows an initial sequence of the SH gene (SEQ ID NO:8) and putative SH protein (SEQ ID NO:9) of APV/CO. FIG. 4a shows the results of a subsequent sequencing of the APV/CO SH gene (SEQ ID NO: 87) and the putative SH protein (SEQ ID NO: 88) based on this sequence. The nucleic acid sequences of FIGS. 4 and 4a are greater than 95% identical, with the initial sequence found to possess a six nucleotide insertion. In FIG. 4a: The gene-start (GS) and the gene-end (GE) transcription signals of the SH gene are indicated in italics. In the SH protein: the potential N-linked glycosylation sites are underlined; the most hydrophobic region that corresponds to the probable transmembrane domain is shown in bold italics.

Figure 1:
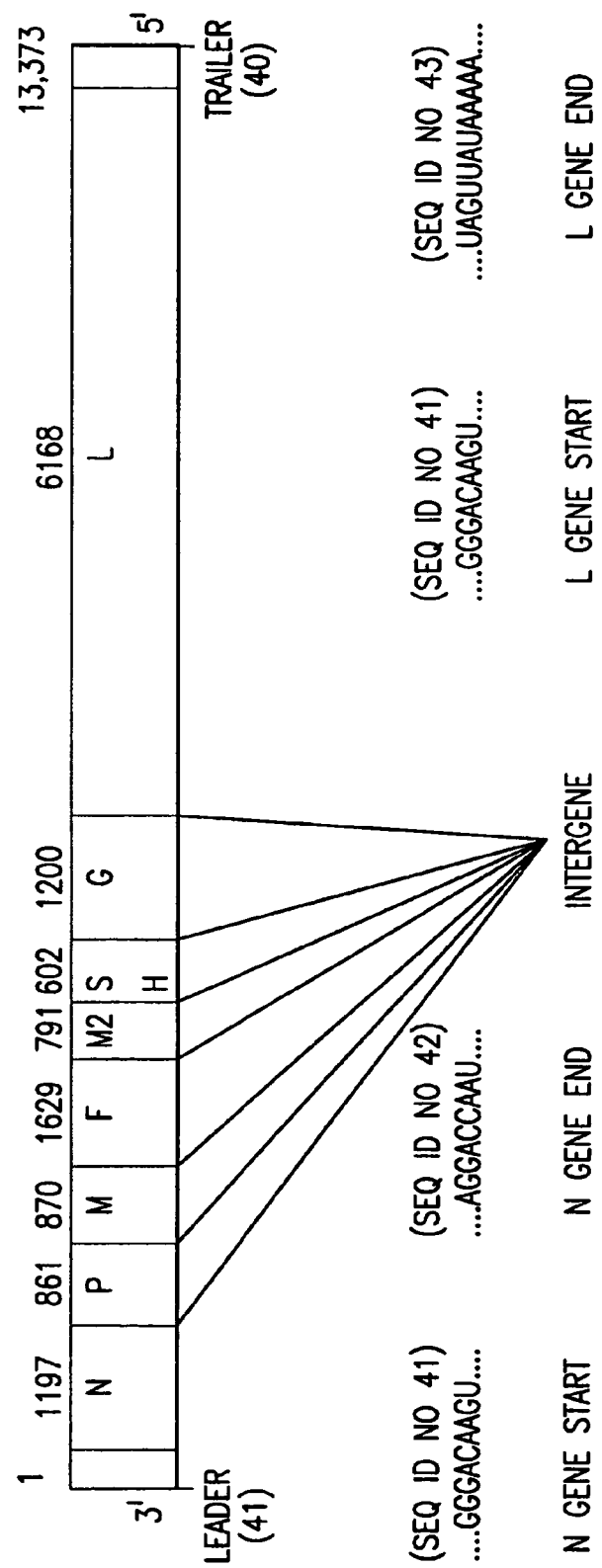
FIG. 1 is a schematic genetic map of APV subgroup A. The gene order, gene start, and gene end sequences are shown.
Figure 5:
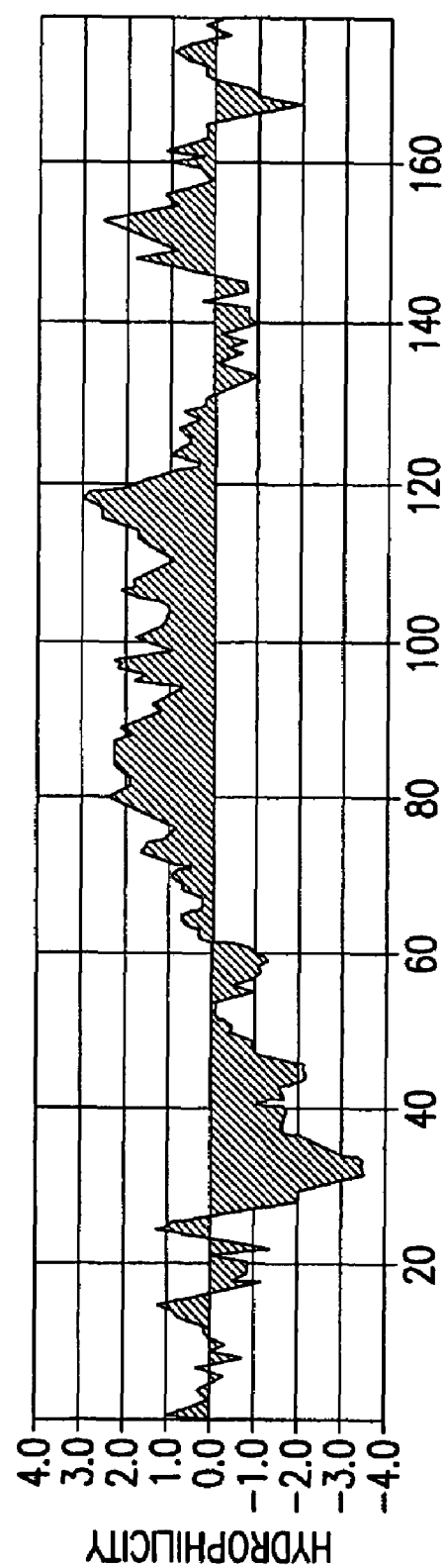

FIG. 5 and 5a show the hydrophilicity profile of APV/CO SH protein from FIG. 4a. The distribution of the hydrophobic and hydrophilic domains along the amino acid sequence was determined using the algorithm of Kyte and Doolittle (1982) with a window size of 7 residues. The Y axis denotes hydrophilicity (hydrophobicity is indicated by negative values) and X axis indicates amino acid position.

Figure 6:
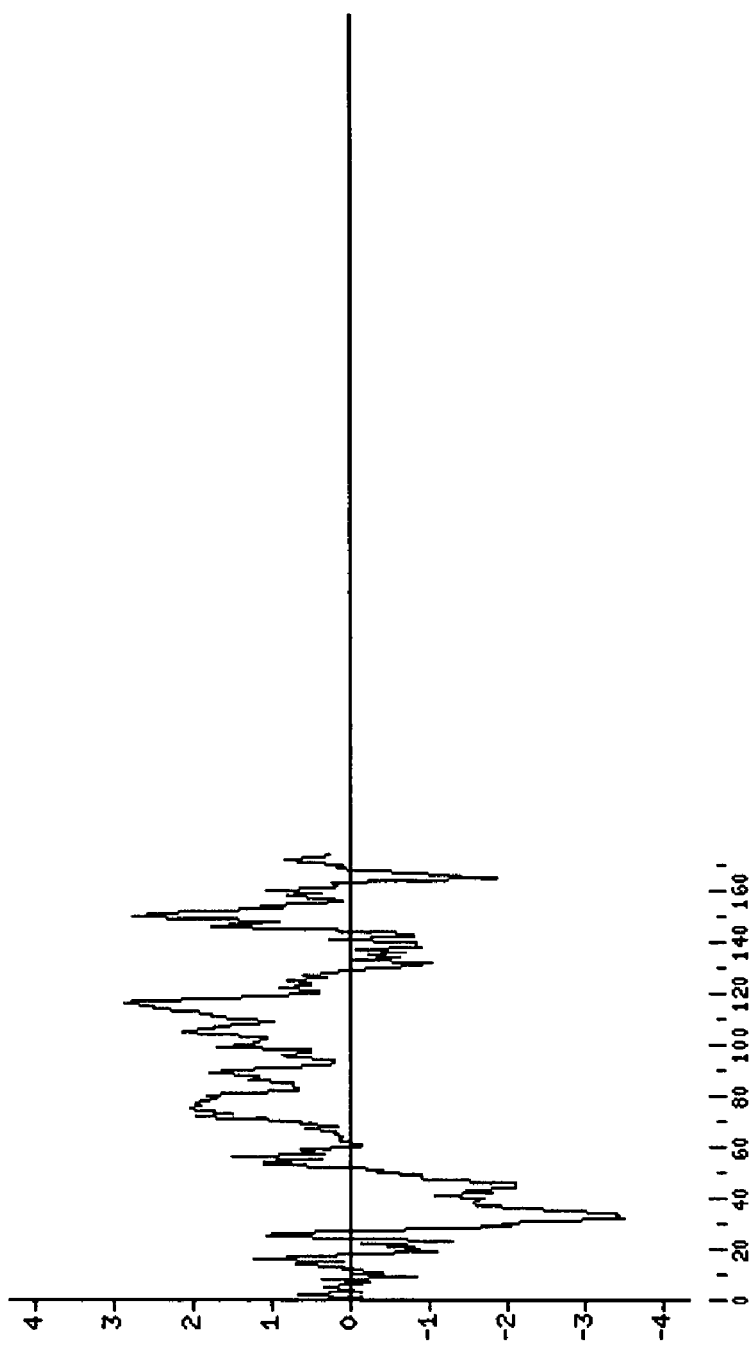

FIG. 6 shows the comparative alignment of the predicted amino acid sequence of putative SH protein of APV/CO (SEQ ID NO:9) with Human metapneumovirus (HMPV) (SEQ ID NO:10), APV subgroups A (APV/A) (SEQ ID NO:11). APV subgroups B (APV/B) (SEQ ID NO:12), human respiratory syncytial virus (HRSV) (SEQ ID NO:13), bovine respiratory syncytial virus (BRSV) (SEQ ID NO:14), and Pneumonia virus of mice (PVM) (SEQ ID NO: 15). FIG. 6a shows the comparative alignment of the predicted amino acid sequence of SH protein of APV/CO (SEQ ID NO:88) with APV subgroups A (APV/A) (SEQ ID NO:97) and B (APV/B) (SEQ ID NO:98), Human metapneumovirus (HMPV) (SEQ ID NO:96), bovine (BRSV) (SEQ ID NO:100) and human respiratory syncytial virus (HRSV) (SEQ ID NO:99) and Pneumonia virus of mice (PVM) (SEQ ID NO:101) generated using Clustal W sequence alignment. Gaps are represented by dashes and periods indicate the positions of identical aa residues compared to APV/CO.

Figure 7:
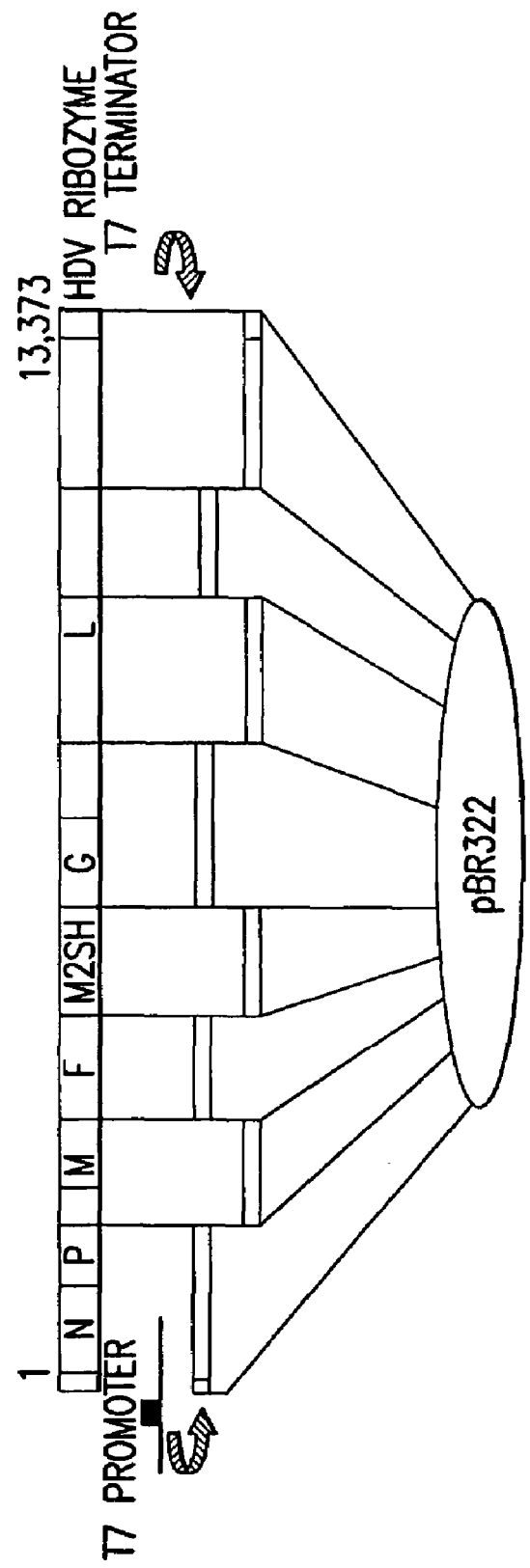

FIG. 7 shows the general scheme for the assembly of cDNA fragments of APV/CO genes in pBR 322.

Figure 8:
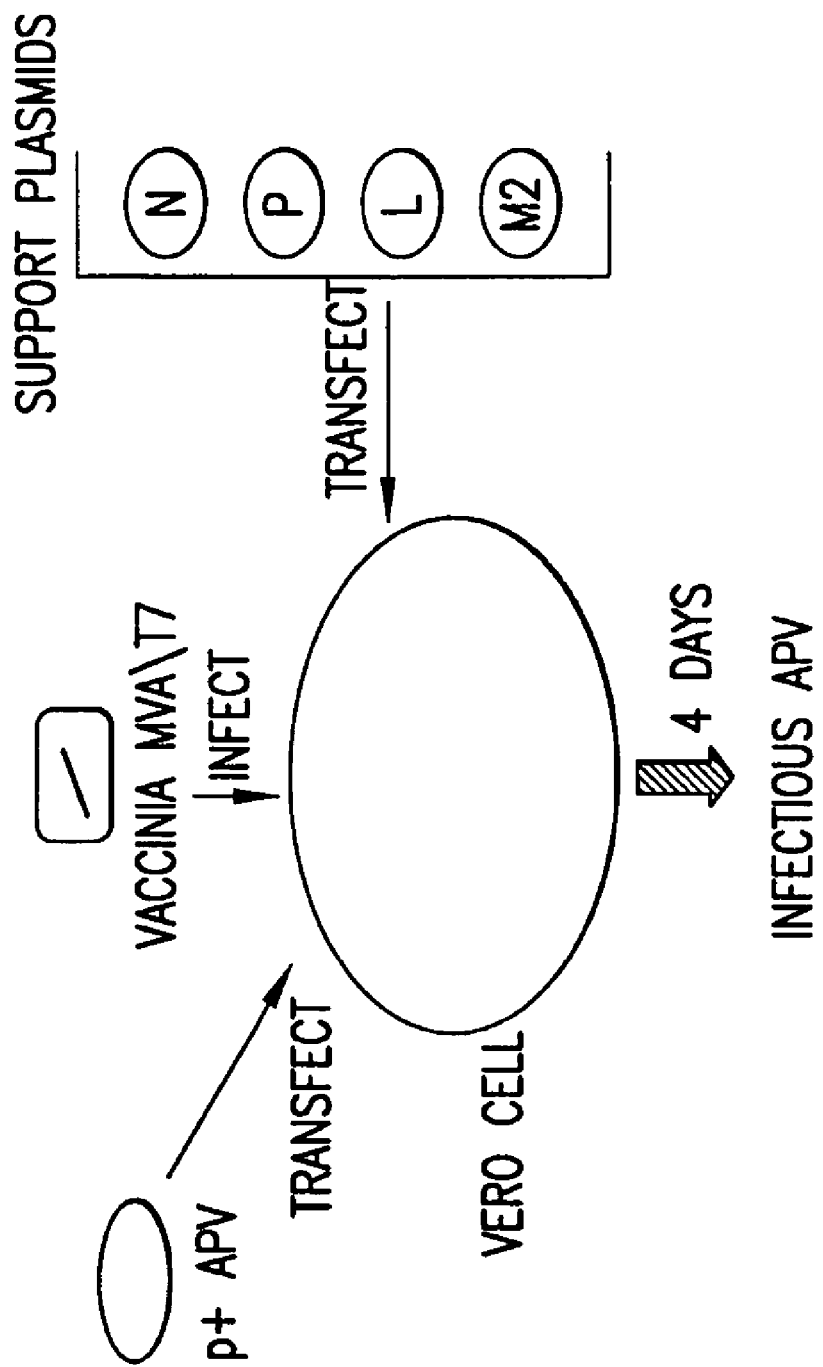

FIG. 8 shows the transfection procedure for the recovery of infectious APV entirely from cloned cDNA. The full length APV cDNA along with support plasmids is transfected into Vero cells infected with a vaccinia virus (MVA-t7) to obtain infectious APV.

FIG. 9 shows the construction of F cleavage site mutant of recombinant APV/CO.

Figure 10:
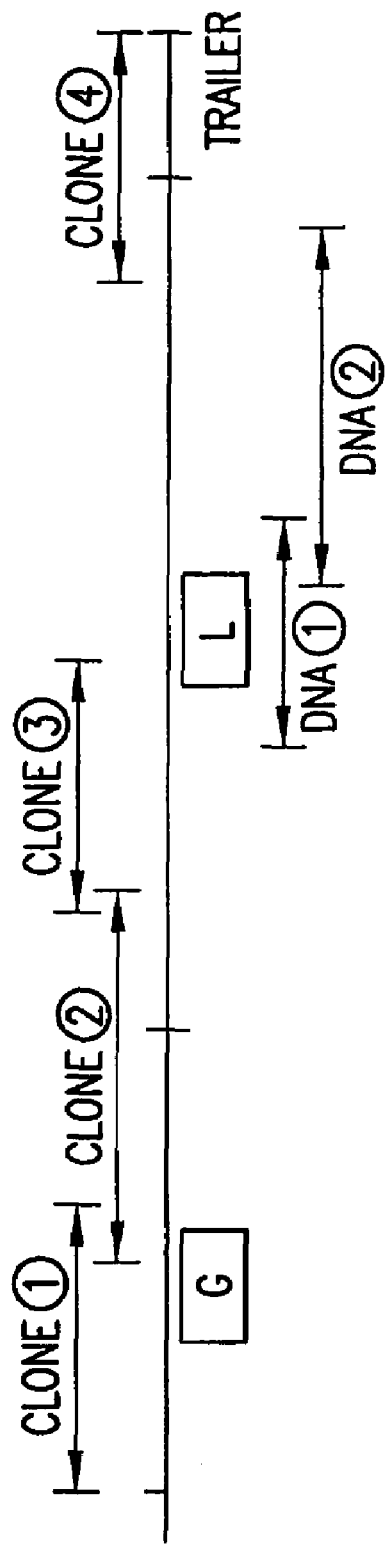

FIG. 10 shows the orientation of APV overlapping nucleic acid material of ATCC Deposit Numbers PTA-5668, PTA-5669, PTA-5670, PTA-5671, PTA-5672, PTA-5673, which are labeled as Clones 1-4, DNA 1 and DNA 2, respectively.

FIG. 11 shows a comparative alignment of the predicted amino acid sequences of three different strains of APV-C, APV/CO, Mn-1a and Mn-2a. Proposed intra-cellular, transmembrane, and extra-cellular domains of the G proteins are indicated above the sequences. Perfectly conserved amino acids relative to APV/CO are indicated by dots, and potential N-linked glycosylation sites are underlined. The amino acid residues forming the highly divergent domain have been highlighted in bold (amino acids 300-450).

Figure 12:
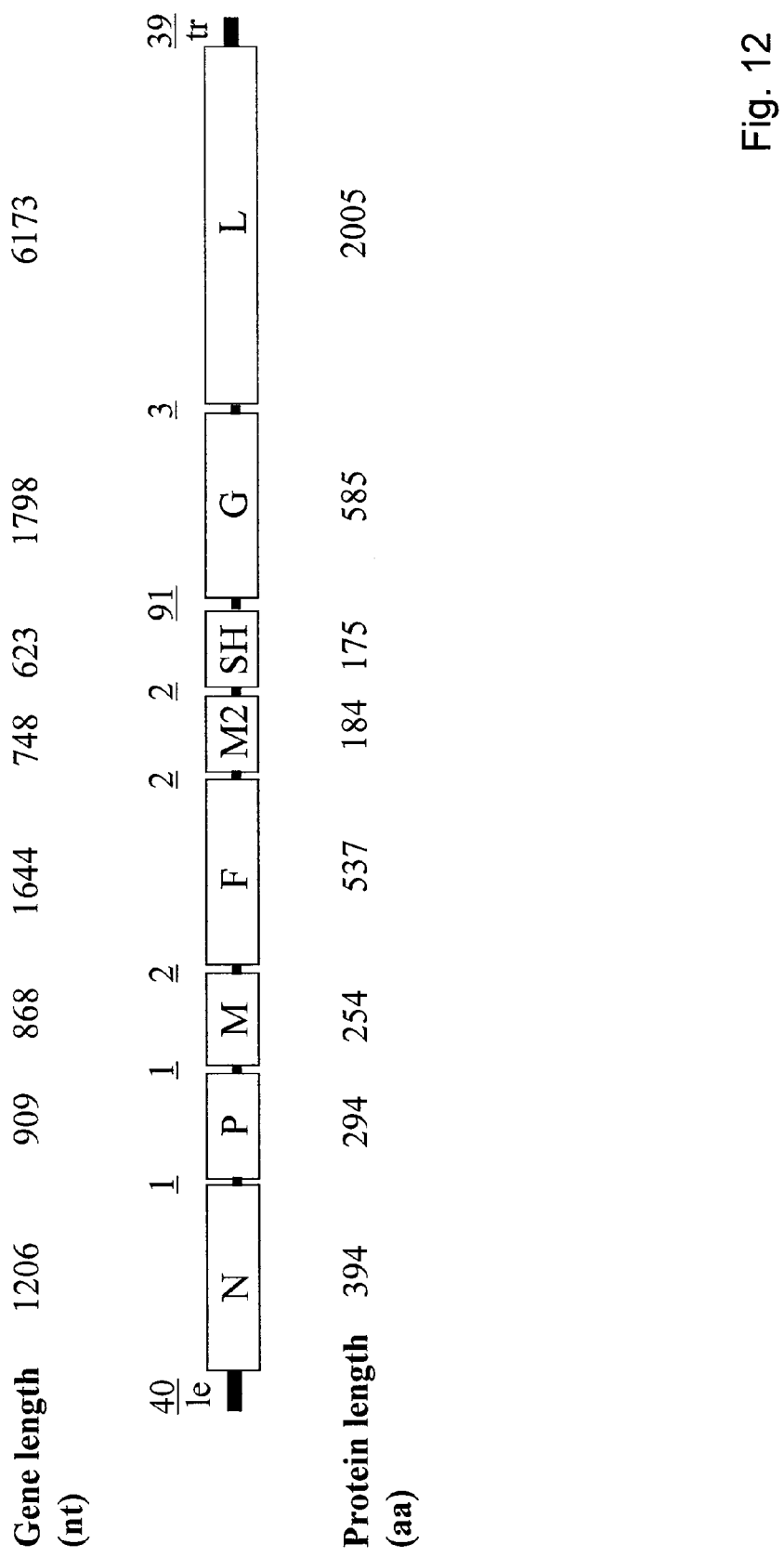

FIG. 12 show the structure of the APV/CO genome. Individual genes are indicated by boxes. The gene length and protein length are indicated above and below each gene, respectively. The nucleotide lengths of the 3' leader, 5' trailer, and intergenic regions are underlined.

FIG. 13 shows a complete gene map of APV/CO genome (in antigenome-sense). The last nucleotide of the gene-end, the first nucleotide of the gene-start, and the first and last nucleotides of the leader and trailer are numbered. Conserved sequence motifs at the gene-end and the gene-start of each gene are indicated in bold upper case, and a consensus is given below. Translational stop and start codons are underlined. Intergenic sequences are shown between the gene-end and gene-start sequences. In the case of the SH-G intergenic region (91 nucleotides), only the first and last five nucleotides are shown, and the number of the remaining nucleotides is indicated.

Figure 14:
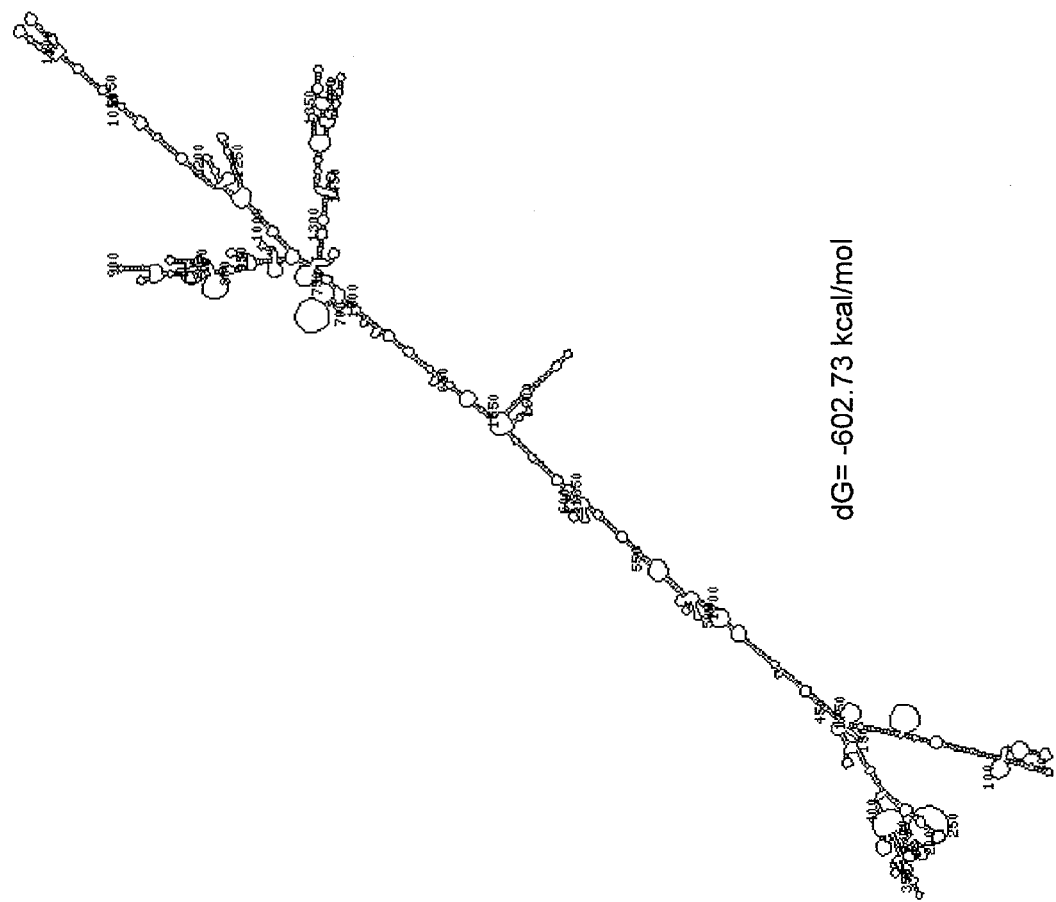

FIG. 14 shows a secondary structure prediction of the G gene (cDNA sense) of APV-C. The MFOLD software program was used to predict the secondary structure and a representative model with its stability (kcal/mol) is shown.

DETAILED DESCRIPTION OF THE INVENTION

The present inventors have identified the coding and amino acid sequence of the small hydrophobic (SH) gene of the avian pneumovirus strain Colorado (APV/CO). The sequences of the SH gene and deduced protein are shown in FIG. 4a (SEQ ID NOs:87 and 88). The SH gene sequence reported in SEQ ID NO:87 is greater than 95% identical to the sequence reported in SEQ ID NO:8; the invention therefore encompasses both sequences and the putative protein sequences based upon them. The SH gene of APV/CO reported in FIG. 4a is 622 nucleotides in length. Comparison of the deduced amino acid sequence of the SH protein of APV/CO with the corresponding published sequences of other members of genera metapneumovirus showed 24% identity with the newly discovered human metapneumovirus (hMPV). Additionally, the predicted amino acid sequences for the G glycoprotein genes of APV subgroup C members APV/CO, Mn-1a, and Mn-2a have also been identified and are shown in FIG. 11 (SEQ ID NOs:56, 57, and 58). The complete nucleotide sequence of the APV/CO G gene is 1758 nucleotides in length, encoding a polypeptide of 585 amino acids. Though the G protein of APV-CO showed structural and biochemical features similar to those of the HMPVs, it showed only 21 to 25% amino acid identity with those of the HMPVs and less in comparison with other APVs. Also provided are the nucleotide sequences of transcription-signals and the N-P, P-M, M-F, F-M2, M2-SH, SH-G, and G-L intergenic regions, and the 3' leader and 5' trailer regions of APV/CO (FIG. 13).

In accordance with an aspect of the present invention, there is provided an isolated nucleic acid molecule comprising a nucleotide sequence encoding the SH protein (SEQ ID NO: 88) or a nucleotide sequence of the SH gene (SEQ ID NO:87). Isolated nucleic acid molecules of the present invention include polynucleotides comprising the exact sequence shown in SEQ ID NO:87, and polynucleotides which comprise a sequence substantially different from those described above but which, due to the degeneracy of the genetic code, still encode the SH protein. Of course, the genetic code is well known in the art. Thus, it would be routine for one skilled in the art to generate the degenerate variants described herein.

Unless otherwise indicated, each "nucleotide sequence" set forth herein is presented as a sequence of deoxyribonucleotides (abbreviated A, G, C and T) or ribonucleotides (A, G, C and U). However, by "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U).

Polynucleotides useful in the present invention may be in the form of RNA or in the form of DNA, which DNA includes cDNA, genomic DNA, and synthetic DNA. The DNA may be double stranded or single-stranded, and if single stranded may be the coding strand or non-coding (anti-sense) strand.

The polynucleotide which encodes for the polypeptide of SEQ ID NO:88 may include: only the coding sequence for the polypeptide; the coding sequence for the polypeptide and additional coding sequence such as a leader or secretary sequence or a proprotein sequence; the coding sequence for the polypeptide (and optionally additional coding sequence) and non-coding sequence, such as intron or non-coding sequence 5' and/or 3' of the coding sequence for the predicted SH polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of SEQ ID NO:88. The variant of the polynucleotide may be a naturally occurring allelic variant of the polynucleotide or a non-naturally occurring variant of the polynucleotide. As known in the art, an allelic variant is an alternate form of a polynucleotide sequence which may have a substitution, deletion or addition of one or more nucleotides, which does not substantially alter the function of the encoded polypeptide.

The present invention also includes polynucleotides, wherein the coding sequence for the polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for proprotein which is the protein plus additional 5' amino acid residues. A mature protein having a prosequence is a proprotein and is an inactive form of the protein. Once the prosequence is cleaved an active mature protein remains.

Thus, for example, the polynucleotide may encode for a SH protein alone, or for a protein having a prosequence or for a protein having both prosequence and a presequence (leader sequence).

The polynucleotides useful in the present invention may also have the coding sequence fused in frame to a marker sequence which allows for purification of the polypeptide of the present invention. The marker sequence may be a hexa-histidine tag supplied by a pQE-9 vector to provide for purification of the polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I. et al., *Cell* 37:767 (1984)).

The term "gene" means the segment of DNA involved in producing a polypeptide chain; it includes regions preceding and following the coding region (leader and trailer) as well as intervening sequences (introns) between individual coding segments (exons).

Further embodiments of the invention include isolated nucleic acid molecules comprising a polynucleotide having a nucleotide sequence at least 90% identity, and more preferably at least 95%, 97%, 98% or 99% identity to (a) a nucleotide sequence encoding the SH polypeptide having the complete amino acid sequence in FIG. 4*a* (SEQ ID NO:88); (b) a nucleotide sequence having the complete coding region of the SH gene in FIG. 4*a* (SEQ ID NO:87); (c) a nucleotide sequence having the complete sequence of the SH gene in FIG. 4*a* (SEQ ID NO:87); (d) a nucleotide sequence encoding any of the SH analogs or deletion mutants described below; or (e) a nucleotide sequence which is fully complementary to any of the nucleotide sequences in (a), (b), (c) or (d).

Preferred, are nucleic acid molecules having sequences at least 90%, 95%, 96%, 97%, 98% or 99% identical to the nucleic acid sequence shown in FIG. 4*a* (SEQ ID NO:87) which encode a polypeptide having SH protein activity. By "a polypeptide having SH activity" is intended polypeptides exhibiting activity similar, but not necessarily identical, to an activity of the wild-type SH protein or an activity that is enhanced over that of the wild-type SH protein, as measured in a particular biological assay. Particular preferred are polypeptides which are specifically antigenic, that is, induce an immune response which is specific for the wild-type SH protein.

Of course, due to the degeneracy of the genetic code, one of ordinary skill in the art will immediately recognize that a large number of the nucleic acid molecules having a sequence at least 90%, 95%, 96%, 97%, 98%, or 99% identical to the reference nucleic acid sequence will encode a polypeptide "having SH protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having SH protein activity. This is because the skilled artisan is fully aware of amino acid substitutions that are either less likely or not likely to significantly effect protein function (e.g., replacing one aliphatic amino acid with a second aliphatic amino acid). Thus, the invention further includes variations of the SH polypeptide which show substantial SH polypeptide activity or which include regions of SH protein which are antigenic. Such mutants include deletions, insertions, inversions, repeats, and type substitutions (for example, substituting one hydrophilic residue for another, but not strongly hydrophilic for strongly hydrophobic as a rule). Small changes or such "neutral" amino acid substitutions will generally have little effect on activity.

Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

For example, guidance concerning how to make phenotypically silent amino acid substitutions is provided in Bowie, J. U. et al., "Deciphering the Message in Protein Sequences: Tolerance to Amino Acid Substitutions," *Science* 247:1306-1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that maintain functionality. As the authors state, these studies have revealed that proteins are surprisingly tolerant of amino acid substitutions. The authors further indicate which amino acid changes are likely to be permissive at a certain position of the protein. For example, most buried amino acid residues require nonpolar side chains, whereas few features of surface side chains are generally conserved. Other such phenotypically silent substitutions are described in Bowie, J. U. et al., *Science* 247:1306-1310 (1990) and the references cited therein.

The present invention further relates to an SH polypeptide which has the deduced amino acid sequence of FIG. 4*a* (SEQ ID NO:88), as well as fragments, analogs and derivatives of such polypeptide. The terms "fragment," "derivative" and "analog" when referring to a polypeptide of the invention, means a polypeptide which retains essentially the same biological function or activity as such polypeptide, preferably antigenicity. Thus, an analog includes a protein which can be activated by cleavage of the protein portion to produce an active polypeptide.

The fragment, derivative or analog of the polypeptide of FIG. 4*a* (SEQ ID NO:88) may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the polypeptide is fused with another compound, such as a compound to increase the half-life of the polypeptide (for example, polyethylene glycol), or (iv) one in which the additional amino acids are fused to the polypeptide, such as a leader or secretary sequence or a sequence which is employed for purification of the polypeptide or a protein sequence. Such fragments, derivatives and analogs are deemed to be within the scope of those skilled in the art from the teachings herein.

By a fragment of an isolated the SH polypeptide, for example, is intended to encompass polypeptide fragments contained in SEQ ID NO:88 or encoded by SEQ ID NO:87. Protein fragments may be "free-standing," or comprised within a larger polypeptide of which the fragment forms a part or region, most preferably as a single continuous region. Polypeptide fragments can be at least 20, 30, 40, 50, 60, 70, 80, 90, 100, 110, 120, 130, 140, or 150 amino acids in length. In this context "about" includes the particularly recited ranges, larger or smaller by several (5, 4, 3, 2, or 1) amino acids, at either extreme or at both extremes.

Even if deletion of one or more amino acids from the N- or C-terminus of a protein results in modification of loss of one or more biological functions of the protein, other functional activities (e.g., biological activities, ability to multimerize, ability to raise antibodies) may still be retained. For example, the ability of shortened SH mutants to induce and/or bind to antibodies which recognize the complete form of the polypeptides generally will be retained when less than the majority of the residues of the complete polypeptide are removed from the N- or C-terminus. Whether a particular polypeptide lacking N-terminal residues of a complete polypeptide retains such immunologic activities can readily be determined by routine methods described herein and otherwise known in the art. It is not unlikely that an SH mutant with a large number of deleted terminal amino acid residues may retain some biological or immunogenic activities. In fact, peptides composed of as few as six amino acid residues may often evoke an immune response.

A further embodiment of the invention relates to a polypeptide which comprises the amino acid sequence of a SH polypeptide having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions. Of course, it is highly preferable for a peptide or polypeptide to have an amino acid sequence which comprises the amino acid sequence of a SH polypeptide, which contains at least one, but not more than 20, 19, 18, 17, 16, 15, 14, 13, 12, 11, 10, 9, 8, 7, 6, 5, 4, 3, 2 or 1 amino acid substitutions. Also provided are polynucleotides encoding such polypeptides.

The polypeptides and polynucleotides of the present invention are preferably provided in an isolated form, and preferably are purified to homogeneity. By "isolated" is intended a polynucleotide or polypeptide removed from its native environment. Thus, a polynucleotide or polypeptide produced and/or contained within a recombinant host cell is considered isolated for purposes of the present invention. Also intended are polypeptides that have been purified, partially or substantially, from a recombinant host cell or a native source. Recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

The polypeptides of the present invention include the polypeptide of SEQ ID NO:88 as well as polypeptides which have at least 90%, 95%, 96%, 97%, 98%, 99% identity to the polypeptide of SEQ ID NO:88 and also include portions of such polypeptides with such portion of the polypeptide generally containing at least 30 amino acids and more preferably at least 40, 50, 60, 70, 80 or 100 amino acids.

By a polypeptide having an amino acid sequence at least, for example, 95% "identical" to a reference amino acid sequence polypeptide is intended that the amino acid sequence of the polypeptide is identical to the reference sequence except that the polypeptide sequence may include up to five amino acid alterations per each 100 amino acids of the reference amino acid. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide or polynucleotide is at least 90%, 95%, 96%, 97%, 98% or 99% identical to another polypeptide or polynucleotide can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (*Comp. App. Biosci.* 6:237-245 (1990)). In a sequence alignment the query and subject sequences are either both nucleotide sequences or both amino acid sequences. The result of said global sequence alignment is in percent identity. Another known computer programs for determining percent identity is the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid or nucleotide sequence and that gaps in homology of up to 5% of the total number of amino acid or nucleotide residues in the reference sequence are allowed.

The present invention is also directed to recombinant nucleic acid molecules comprising APV/CO genes and/or intergenetic sequences. Since the sequence of the intergenic sequences of APV/CO and the sequence of the SH gene are provided here, and the sequences of the N, P, M, F and M2 genes are known, one of ordinary skill can construct a recombinant nucleic acid molecule comprising one or more of these genes or intergenetic sequences. Especially preferred are isolated nucleic acid molecules comprising the SH gene in combination with one or more of the following sequences: the 5' trailer sequence; the N gene; the P gene; the M gene; the F gene; the M2 gene; the M-F intergenetic sequence; the F-M2 intergenetic sequence; the M2-SH intergenic sequence; and the SH-G intergenic sequence.

The present invention also relates to vectors which include the isolated nucleic molecules of the present invention, host cells which are genetically engineered with the recombinant vectors, and the production of APV polypeptides or fragments thereof by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the APV genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence (promoter) to direct cDNA synthesis. As representative examples of such promoters, there may be mentioned: LTR or SV40 promoter, the *E. coli*. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline, kanamycin or ampicillin resistance in *E. coli*.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli, Streptomyces, Salmonella typhimurium*; fungal cells, such as yeast; insect cells such as *Drosophila* S2 and *Spodoptera* Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pBS, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia); Eukaryotic: pWL-NEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L. et al., *Basic Methods in Molecular Biology* (1986)). Preferably, the host cell is an ompT-deficient prokaryotic cell. Particularly preferred ompT-deficient prokaryotic cells are gram-negative bacteria, *Psudomonas, Klebsiella, E. coli* and *Salmonella*.

The constructs in host cells can be used in a conventional manner to produce the gene product encoded by the recombinant sequence. Alternatively, the polypeptides of the invention can be synthetically produced by conventional peptide synthesizers.

APV proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., *Molecular Cloning: A Laboratory Manual*, Second Edition, Cold Spring Harbor, N.Y. (1989), the disclosure of which is hereby incorporated by reference.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

The polypeptide can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the APV protein. Finally, high performance liquid chromatography (HPLC) can be employed for final purification steps.

Reverse genetics systems for bovine RSV (Yunus et al., *Virus Genes* 23:157-164 (2001)) and NDV strains Badette C and LaSota (Huan et al., *J. Gen. Virol.* 82:1729-1736 (2001)) are known. APV is closely related to bovine RSV and DNV in genome organization; therefore, the reagents and techniques used for the development of reverse genetics systems for bovine RSV and NDV should be directly applicable for the development of a similar system for APV.

The ability to recover infectious APV from cDNA greatly facilitates vaccine development and molecular biologic studies, which can provide fundamental information on APV. With regard to vaccine development, this makes it possible to (i) identify attenuating mutations, (ii) create new types of attenuating mutations, including deletion of the viral genome, (iii) combine attenuating mutations to create a stable vaccine virus, and (iv) modify vaccine virus to accommodate antigenic drift in circulating virus. In addition, it becomes possible to insert foreign sequences into the APV genome for coexpression. For example, the G genes of APV subgroups A and B viruses, the gene for protective antigen of another avian pathogen or the genes for cytokines can be inserted into the APV genome for coexpression. Also, direct engineering of infectious APV will lead the way for basic studies of APV molecular biology and pathogenesis. For the first time, it will be possible to study the function of each APV gene in an authentic virus system. Lastly, these studies may provide information useful for studies involving non-U.S. APV isolates and human metapneumovirus.

APV causes a severe respiratory tract disease in turkeys. It is considered to be one of the most important emerging viral diseases in the United States and is of great economic threat to the U.S. poultry industry. APV has become a major problem for the turkey industry in Minnesota. Economic losses due to APV infection in the Minnesota turkey industry alone have been estimated at $15 million annually. Recent studies have shown that APV has already spread to several neighboring states, suggesting that the virus will probably spread to other states across the nation. Since U.S. APV isolates are antigenically and genetically different from those from other parts of the world, it is necessary to understand the molecular biology and pathogenesis of the U.S. isolates and develop effective vaccines for control of the virus.

At present there are no satisfactory live-attenuated or inactivated vaccines available for the prevention of APV infection in the United States (Goyal et al., North Central Avian Disease Conference, Minneapolis, Minn., October 1999)). Therefore, an alternative safe and efficacious vaccine would be beneficial to the U.S. turkey industry. Live attenuated vaccines are inexpensive and have been proven effective against many viral infections; but, live-attenuated vaccines are made empirically, and the molecular basis of attenuation is in most cases, not understood. Since the genomes typically contain many changes, the ability to directly engineer mutations into cDNA makes it possible to generate defined attenuated strains where cDNA serves as a stable vaccine "seed." Another limitation of currently used, live-attenuated vaccines is their reversion to virulence. This limitation can be overcome by designing attenuating mutations in the genome that are less likely to revert to virulence. Due to recent technological advances, it is now possible to design attenuated vaccine strains of nonsegmented negative-stranded RNA viruses by direct genetic manipulation at the cDNA level. To date, complete infectious recombinant virus has been recovered from full-length cDNA for several nonsegmented negative-strand viruses (Baron and Barrett; *J. Virol.* 71:1265-1271 (1997); Clarke et al., *J. Virol.* 74:4831-4838 (2000); Collins et al., *PNAS (USA)* 92:11563-11567 (1995); Garcin et al., *EMBO J.* 14:6087-6094 (1995); Gassen et al., *J. Virol.* 74:10737-44 (2000); Hoffman and Banerjee, *J. Virol* 71:4272-4277 (1997); Peeters et al., *J. Virol* 73:5001-5009 (1999); and Radecke et al., *EMBO J.* 14:5773-5784 (1995)).

A recent breakthrough in the field of nonsegmented negative-strand RNA viruses is the establishment of a system to recover infectious virus entirely from cloned DNA. This new technology has made it possible to introduce mutations into viral genomes and hence, allow reverse genetics. This has significant implications for our understanding of fundamental aspects of the replication of these viruses and the development of vaccines. To date, several nonsegmented negative-strand RNA viruses have been rescued from cDNA clones. However, a reverse genetics rescue system is not currently available for APV. Therefore, we are proposing to develop a rescue system for APV. Availability of a rescue system for APV will enable us to understand the pathogenesis of this virus and develop immunological formulations.

Thus, in accordance with another aspect of the invention, there are provided cDNA molecules encoding the APV antigenome. These cDNA molecules are useful in constructing recombinant APV, as well as live-attenuated APV for use as immunological formulations.

In accordance with another aspect of the invention, there are also provided method of producing recombinant APV viruses using a cDNA molecule encoding the APV antigenome. Recombinant APV viruses may be produced by constructing a cDNA encoding the APV antigenome, transfecting the cDNA into a host cell, and culturing the host cell under conditions suitable to express the APV cDNA and produce APV.

In accordance with another aspect of the invention, there are provided methods of producing live-attenuated APV. Live-attenuated APV is produced by constructing a cDNA molecule encoding the APV antigenome with one or more attenuating mutations incorporated therein, transfecting the cDNA into a host cell, and culturing the host cell under conditions suitable to express the APV cDNA and produce APV. Also provided are viruses produced by such methods.

An attenuating mutation refers to a nucleotide mutation or amino acid coded for in view of such a mutation which results in a decreased probability of causing disease in its host (i.e., a loss of virulence), in accordance with standard terminology in the art. The attenuating mutation may be a substitution, deletion or insertion.

In an embodiment of the invention, random mutations are made in the cDNA molecule encoding the APV antigenome. Viruses produced by this method are tested for virulence. The sequence of the RNA genome isolated from the attenuated virus is determined and compared to a control sequence of either the prototype strain or parent strain. Nucleotide sequence variations between the virulent strain and the attenuated strain can be identified.

The ability to generate viral progeny through plasmid-mediated introduction of a viral genome can also be used to produce viruses with defined molecular changes. In this embodiment of the invention, stable virus stocks can be produced that contain altered sequences that confer desired properties on the virus, for example, reduced virulence. This approach can also be used to assess the effect of molecular changes on various properties of the virus, i.e. antigenic type, virulence, or attenuation by introducing desired sequence changes into the viral genome, producing virus progeny from the genome, and recovering the virus progeny for characterization. In addition, this approach can be used to construct a virus with heterologous sequences inserted into the viral genome that are concurrently delivered by the virus to generate an immune response against other diseases.

Construction of viral genomes with defined molecular changes can be accomplished using standard techniques such as oligonucleotide-directed, linker-scanning or polymerase chain reaction-based mutagenesis techniques known to those skilled in the art (Zoller and Smith, *DNA* 3:479-488; (1984); Botstein and Shortle, *Science* 229:1193 (1985)). Ligation of the genome into a suitable vector for transfer may be accomplished through standard techniques known to those skilled in the art.

Transfection of cells with the RNA transcript coded by the full length genomic cDNA can be achieved by any suitable means, such as, for example, by treating the cells with DEAE dextran, treating the cells with Lipofectin, treating cells with calcium-phosphate and by electroporation. APV-permissive cells are cells which, upon transfection with the viral cDNA antigenome, are capable of producing viral particles. Examples of such cells include, but are not limited to, Vero cells, QT23, chicken embryo fibroblast and tracheal organ culture.

Another aspect of the invention relates to a method for inducing an immunological response in a bird which comprises inoculating the bird with a live-attenuated APV adequate to produce antibody and/or T cell immune response to protect said bird from APV infection. Yet another aspect of the invention relates to a method of inducing immunological response in a bird which comprises delivering one or more APV proteins via a vector directing expression of the APV polynucleotide encoding such proteins in vivo in order to induce such an immunological response to produce antibody to protect such bird from APV infection.

Further aspects of the invention relates to an immunological formulation (composition) which, when introduced into a bird, induces an immunological response in that mammal to APV wherein the composition comprises a live-attenuated APV, an APV polypeptide or an APV polynucleotide construct. The immunological formulation may further comprise a suitable carrier. The immunological formulation can be administered intraperitoneally, parenterally, intranasally, epidurally or orally. The immunological formulation may be administered by any convenient route, for example by infusion or bolus injection, by absorption through epithelial or mucocutaneous linings (e.g., oral mucosa, oculonasal, rectal and intestinal mucosa, etc.). It is preferable that the immunological formulation be administered parenterally (including subcutaneous, intramuscular, intravenous, intradermal etc. injection). Formulations suitable for parenteral administration include aqueous and non-aqueous sterile injection solutions which may contain anti-oxidants, buffers, bacteriostats and solutes which render the formulation isotonic with the blood of the recipient; and aqueous and non-aqueous sterile suspensions which may include suspending agents or thickening agents. The formulations may be presented in unit-dose or multi-dose containers, for example, sealed ampules and vials and may be stored in a freeze-dried condition requiring only the addition of the sterile liquid carrier immediately prior to use. The immunological formulation may also include adjuvant systems for enhancing the immunogenicity of the formulation, such as oil-in water systems and other systems known in the art. The dosage will depend on the specific activity of the immunological formulation and can be readily determined by routine experimentation.

In another aspect of the invention, there are provided methods of diagnosis of APV infection in birds. Preferred birds include chickens and turkeys. Particularly preferred are turkeys. It is believed that APV genes and levels of APV protein can be detected in certain body fluids (e.g., sera, plasma, urine, and spinal fluid) and body tissues (especially tissues derived from the lung) from birds (especially chickens and turkeys).

Thus, the present invention provides a method for diagnosis of APV infection in birds, comprising assaying the presence of one or more APV RNA sequences or the expression of one or more APV proteins in a biological sample derived from a putatively infected bird. Higher levels of APV RNA or protein compared to a negative control is indicative of APV infection. The diagnostic method can be used to detect one or more APV RNA sequences and/or proteins.

Any APV gene or protein sequence can be detected using these techniques, including: the 3' leader sequence, N, P, M, F, M2, SH, G, L, and the 5' trailer sequence. Particularly preferred are SH and G. In addition, intergenic RNA sequences of APV can be detected, including the N-P, P-M, M-F, F-M2, M2-SH, SH-G, and G-L sequence.

By "assaying the presence of APV RNA or the expression level of APV proteins" is intended qualitatively or quantitatively measuring or estimating the level of the APV RNA or protein in a biological sample either directly (e.g., by determining or estimating absolute RNA or protein) or relatively (e.g., by comparing to the APV RNA or protein level in a second biological sample).

By "biological sample" is intended any biological sample obtained from an individual, cell line, tissue culture, or other source which contains APV RNA or protein. Biological samples include mammalian body fluids (such as sera, plasma, urine, synovial fluid and spinal fluid) which contain APV protein, and tissues or cells which become infected with APV, such as lung tissue, pneumocytes, sinus, harderian glands, or trachea.

Total cellular RNA can be isolated from a biological sample using the single-step guanidinium-thiocyanate-phenol-chloroform method described in Chomczynski and Sacchi, *Anal. Biochem.* 162:156-159 (1987). Levels of APV RNA are then assayed using any appropriate method. These include Northern blot analysis (Harada et al., *Cell* 63:303-312 (1990)), S1 nuclease mapping (Fujita et al., *Cell* 49:357-367 (1987)), the polymerase chain reaction (PCR), reverse transcription in combination with the polymerase chain reaction (RT-PCR) (Makino et al., *Technique* 2:295-301 (1990)), and reverse transcription in combination with the ligase chain reaction (RT-LCR).

Assaying APV protein levels in a biological sample can occur using antibody-based techniques. For example, APV protein expression in tissues can be studied with classical immunohistological methods (Jalkanen, M., et al., *J. Cell. Biol.* 101:976-985 (1985); Jalkanen, M., et al., *J. Cell. Biol.* 105:3087-3096 (1987)). Other antibody-based methods useful for detecting APV protein gene expression include immunoassays, such as the enzyme linked immunosorbent assay (ELISA) and the radioimmunoassay (RIA).

Suitable labels are known in the art and include enzyme labels, such as, glucose oxidase, and radioisotopes, such as iodine ($^{125}$I, $^{121}$I), carbon ($^{14}$C), sulfur ($^{35}$S), tritium ($^{3}$H), indium ($^{112}$In), and technetium ($^{99m}$Tc); luminescent labels, such as luminol; and fluorescent labels, such as fluorescein and rhodamine, and biotin.

Having generally described the invention, the same will be more readily understood by reference to the following examples, which are provided by way of illustration and are not intended as limiting.

EXAMPLES

Example 1

Cloning of the 3' Leader and 5' Trailer Sequences of APV/CO

The nucleotide sequence of the 3' and 5' extragenic leader and trailer regions was determined for the genomic viral RNA (vRNA) of APV/CO (SEQ ID NO:1). To obtain the sequence of the 3' leader and 5' trailer regions, vRNA was extracted from purified virions and amplified with consensus primers based upon HMPV isolate 00-1 leader and trailer regions. Briefly, to obtain the 3' leader sequence, the APV/CO genomic RNA was reverse-transcribed with a positive-sense consensus 3' end leader primer, le-For (5' GGAGGAC-GAGAAAAAAAC-GC 3') (SEQ ID NO: 79). The resulting cDNA was subjected to PCR with le-For primer and a N gene-specific negative-sense primer, N-540 (5' GATTGT-TGATGCCAGCTTCGTGAA 3') (SEQ ID NO: 80). The PCR product was cloned, and the clones were hybridized with a N gene-specific radio-labeled probe, spanning regions 55-540 nucleotides. The 3' leader sequence was obtained from nucleotide sequencing of numerous hybridization-positive clones. However, to confirm the leader sequence and to determine the presence of primer sequence at the 3' end of the genome, the GeneRacer kit (Invitrogen) was utilized. Briefly, viral RNA was polyadenylated at its 3' end using poly (A) polymerase (Invitrogen) and reverse-transcribed with an oligo dT primer. PCR was performed using a GeneRacer 3' forward primer (supplied with the kit) and the above-described N-540 primer. The amplified cDNA was either directly sequenced or cloned, and several clones were sequenced to obtain the nucleotide sequence of the 3' leader region of the APV-C genome. The sequence of the 5' trailer region was obtained in a similar manner. The APV/CO genomic RNA was reverse-transcribed with an L gene-specific positive-sense primer, L-5787 (5' GTTGGAGGCAG-CAGGGTCATAGAATC 3') (SEQ ID NO: 81), and PCR was performed with L-5787 and a negative-sense consensus 5' end trailer primer, tr-Rev (5' GGAGGACGAGAAAAAAACCG-TAT 3') (SEQ ID NO: 82). The resulting RT-PCR product was either directly sequenced, or cloned and then sequenced, thus giving the nucleotide sequence of the 5' trailer region of APV-CO. The sequence of the 5' trailer region was further confirmed, using the 5' RACE method described by Krishnamurthy & Samal (*J. Gen. Virol.* 79: 2419-2424 (1998)). The cDNA from the above RT reaction was tailed with dCTP using terminal deoxynucleotidyl transferase (Invitrogen), and PCR-amplified with L-5787 and an oligo dG anchor primer (Invitrogen). The PCR product was then cloned, and several clones from independent 5' RACE reactions were sequenced to obtain the nucleotide sequence of the 5' trailer region of the APV-C genome.

The 3' leader of APV/CO is 40 nucleotides in length, which is one nucleotide shorter than those of APV subgroup A (Randhawa et al., *J. Virol.* 71:9849-9854 (1997)) and human metapneumovirus (van den Hoogen et al., *Virology* 295:119-132 (2002)). Twenty-nine of the 40 nucleotides are identical between APV/CO and the human metapneumovirus. The results show that the leader region of APV/CO is more closely related to the human metapneumovirus than to the leader region of APV subgroup A.

The 5' trailer region of APV-CO was 39 nucleotides in length. Both the Canadian isolates of HMPV showed greater sequence similarity to the trailer region of APV/CO than did that of APV-A.

It was observed that both the leader and trailer regions of APV-CO showed higher degrees of resemblance to those of HMPV than to those of APV-A. The leader and trailer regions of APV/CO were also highly complementary to each other; 11 of the first 13 nt and 18 of the terminal 30 nt were exact complements.

Example 2

Cloning of the SH Gene and M-F, F-M2, M2-SH, SH-G Intergenic Regions of APV/CO

The APV/CO isolate was obtained from National Veterinary Services Laboratories (Ames, Iowa) and propagated in Vero cells. The cells were harvested 4-5 days post-infection when maximum cytopathic effect in the form of extensive syncytia was observed. The infected cells were scraped into the medium and lysed by three cycles of freezing and thawing to release the intracellular virus. The cell-lysate was clarified by centrifugation at 3000×g for 15 minutes. The supernatants from infected cells were made 10% with respect to PEG 8000 and incubated for 3 h at 4° C. The virus was pelleted by centrifugation at 3000×g for 30 min at 4° C. The virus pellet was resuspended in PBS and stored at 4° C. APV genomic RNA was extracted from purified APV by TRIzol reagent (Invitrogen Corporation) according to the supplier's protocol except that one additional extraction with phenol plus chloroform was added to the procedure.

The "genome-walking" strategy was employed for obtaining the sequences of the SH gene and M-F, F-M2, M2-SH & SH-G intergenic regions of APV/CO. The genome-walking technique was based on sequential cDNA synthesis from the known genes at the 3' end of the negative-sense genomic RNA traversing into the regions of the genome located at the 5' end. Briefly, we used APV genomic RNA and gene specific positive sense primers within M, F or M2 genes in Reverse Transcription-PCR (RT-PCR) reactions. The first RT-PCR reaction with the M gene primer (5'-GGTGCAGGAGTTCAGGTAATAGTGGAG-3'; (SEQ ID NO:16) Genbank accession: AF262571) yielded M-F intergenic sequence and the second RT-PCR with an F gene primer (5'-GCATGGTGGCCTTATCACCACTGGGTGCT-3' (SEQ ID NO:17); Genbank accession: AF187152) yielded the F-M2 intergenic sequence. In order to obtain the SH gene sequence, a third reverse transcription reaction was initiated within the M2 gene with the positive sense primer (5'-GCG-GAGAACATGGCCTGATCTTCCTGA-3' (SEQ ID NO:18); Genbank accession: AF176592). The first strand cDNA was purified using a nucleotide removal kit (Qiagen). The purified cDNA was tailed with C nucleotides in a tailing reaction catalyzed by terminal deoxynucleotidyl transferase enzyme (Invitrogen Corporation). A PCR was set up with dC-tailed cDNA template and the positive sense M2 forward primer and a poly dG-anchor reverse primer (Invitrogen Corporation). The amplified PCR product was cloned into a TA cloning vector (Invitrogen Corporation) and transformed using DH10B cells (Invitrogen Corporation). The resulting colonies were hybridized with a radiolabelled M2 cDNA probe. Several hybridization-positive clones, each containing a long insert, were selected and sequenced. Several of the positive clones yielded the entire SH gene, including the M2-SH and SH-G intergenic regions.

The cDNA synthesis initiated at the M gene yielded lead to the sequence for M-F intergenic region. Similarly, cDNA synthesis initiated within the F gene yielded the sequence for F-M2 intergenic region. Subsequently, cDNA initiated within the M2 gene traversed the M2-SH intergenic region into the SH gene, followed by the SH-G intergenic region and entered the G gene. The M-F, F-M2, M2-SH intergenic regions of APV/CO are each two nucleotides in length and identical in sequence, 3'-UU-5' (FIG. 3). However, the SH-G intergenic region was considerably longer consisting of 91 nucleotides (FIG. 3). Thus, during the cloning of the SH gene we traversed the APV genome in the order 3'-M-F-M2-SH-G-5' (FIG. 3). These data confirmed the presence and the location of the SH gene and showed that the gene order of the APV/CO isolate indeed conforms to the genus *Metapneumovirus* (Pringle, *Arch. Virol.* 143:1449-1459 (1998)).

The nucleotide and deduced amino acid sequence of the SH gene of APV/CO is shown in FIG. 4*a*. The SH gene, from gene start (GS) to gene end (GE), is 622 nucleotides in length (SEQ ID NO:87). The SH gene starts with a conserved GS sequence, 3'-CCCUGUUCA-5' (part of SEQ ID NO. 1) and ends in a semi-conserved GE sequence of 3'-UCAAUAAAU-UUU-5' (SEQ ID NO 46) (nucleotides GGGACAAGT-CAAC<u>ATG</u>GAGCCCCTGAAAGTCTCTGGAAGTG GAGGGATACCGATGAAGACAAGGCT-TAATATCATACTTGAG AAGTCAATCAATAAAATCT-TGATCATTTTAGGATTACTATTA ACTGCCTCAACTG-TAATTACAATCACACTCACAGTGGAGTAT ATAAGAGTAGAAAATGAATTG-CAACTTTGCAAGATGGAAGC AGAGGTGGCCAAGA-CAACTCCGGAACCACCAACACAGCCAA CGAAGA-CAACTCCTACACTAACCAGAACCAGATCAACCACC GCATCCCTCAAAACCAGAC-CAGTTTCAAGGACCACTCATCCC ACCAATC-CCAGCTGCTGGAGAGAGGAGGAAAAGTGCCAGA ATATCACAGCTAAATGGTCCAAT-TGTTTTGGCACATCTCTAC CTGTGAGGGTGAACTG-CACGGTACTAAGAGAATTGTGTGAT GAGCAGCCAG-GCAATCACACAACAGTTCAAGTATCAAGGAG GTGTACATGCATATATGCATTAAATTGG-GATTGTAGTTATGC TTGAGAGAGAGACTACAC TAGCCGACCCTAATGAGGTCCAC AGAAAAAGAT-TAAAAGCATAAACCAATTTTTTAGTTATTTAA AAA of SEQ ID NO:87). The results showed that the gene-start sequences were perfectly conserved in all the APV/CO genes; whereas, the gene-end sequences were less conserved in all the APV/CO genes.

The longest ORF, which is in the most favorable context, encodes a polyprotein of 175 amino acids (molecular weight=19.54 kilodaltons), is the putative SH protein of APV/CO (SEQ ID NO:88). Two other downstream ORFs encoding smaller proteins of 164 amino acids and 114 amino acids were also identified. The putative ORF of the SH protein APV/CO is the second longest in the genus *pneumovirus*, after hMPV SH protein, which is 183 amino acids long. The ORF of the SH protein of APV/CO is longer than the ORF of SH protein of APV/A by one amino acid (Ling et al., 1992; Genbank accession: CAD42709). In contrast, the SH protein of PVM, HRSV, and BRSV are comparatively shorter, consisting of 92, 73 and 64 amino acids, respectively (Collins et al., *J. Gen. Virol.* 71:1571-1576 (1990); Easton and Chambers, *Virus Res.* 48:27-33 (1997); Samal and Zamora, *J. Gen. Virol.* 72:1715-1720 (1991)).

The amino acid (aa) composition of the SH protein of APV/CO is relatively similar to that of the hMPV, APV/A, RSV and BRSV with a high percentage (22%) of threonine and serine residues (Collins et al., *J. Gen. Virol.* 71:1571-1576 (1990); Easton and Chambers, *Virus Res.* 48:27-33 (1997); Samal and Zamora, *J. Gen. Virol.* 72:1715-1720 (1991); Van den Hoogen et al., *Nat. Med.* 7:719-724 (2001)). The putative SH protein of APV/CO contains 9 cysteine residues, whereas the corresponding proteins of hMPV and APV/A contain 10 and 16 cysteine residues, respectively (van den Hoogen et al., *Virology* 295:119-132 (2002)). The putative SH protein of APV/CO contains 3 potential N-linked glycosylation sites (FIG. 4a).

The hydrophilicity profile for putative SH protein of APV/CO showed a hydrophilic N-terminus followed by a hydrophobic domain, which can serve as a potential membrane-spanning domain (amino acid 28 to 51 for APV/CO), and a predominantly hydrophilic C terminus (FIG. 5a). As with other pneumovirus SH proteins, this result is consistent with the APV/CO SH protein being a type II glycoprotein, having an uncleaved signal-anchor sequence proximal to the N-terminus with the C-terminus being extracellular. Comparison of the hydrophilicity profile for the putative SH protein of APV/CO with the hydrophilicity profiles of SH proteins of hMPV, APV/A, and APV/B revealed similar characteristics (Ling et al., *J. Gen. Virol.* 73:1709-1715 (1992), Van den Hoogen et al., *Virology* 295:119-132 (2002)).

Clustal W alignment (FIG. 6a) showed that the SH protein of APV/CO shares a higher amino acid sequence identity with the SH protein of hMPV than with the SH proteins of APV/A, APV/B and BRSV (Collins et al., *J. Gen. Virol.* 71:1571-1576 (1990); Easton and Chambers, *Virus Res.* 48:27-33 (1997); Samal and Zamora, *J. Gen. Virol.* 72:1715-1720 (1991)). It was somewhat surprising to find that the SH protein of APV/CO shares a higher sequence identity with a mammalian *Metapneumovirus* than with its avian counterparts.

A phylogenetic tree based on SH protein sequences of APV/CO and other members of genus *Pneumovirus* was constructed. These results agree with the previous finding based on a phylogenetic relationship deduced on the basis of more conserved proteins, M2-1 and L of hMPV, that the mammalian metapneumovirus is closely related to APV/CO among the metapneumoviruses, isolated thus far (Van den Hoogen et al., *Nat. Med.* 7:719-724 (2001)).

The G protein has been most often used to define the antigenic polymorphisms in *Pneumovirus* (Collins et al., "Parainfluenza viruses," in *Fields Virology*, Fields et al., eds., Lippincott-Raven, Philadelphia, Pa. (1996), pp. 1205-1241). The highest sequence divergence in terms of low amino acid (aa) and nucleotide (nt) sequence identity especially in G-ectodomain among different strains, has been extensively used to draw phylogenetic relationships. Based on G sequence and its reactivity to monoclonal antibodies, two antigenic subgroups A and B have been defined for BRSV and HRSV strains, respectively (Anderson et al., *J. Inf. Dis.* 151: 626-633 (1985); Johnson et al., *PNAS (USA)* 84:5625-5629 (1987); Mallipeddi and Samal, *J. Gen. Virol.* 74:2001-2004 (1993)). Similarly, in Avian Metapneumovirus, based on 38% nt identity and 56% predicted aa identity in the G gene of different groups of European isolates, two subgroups A and B of APV have been defined in Europe (Juhasz & Easton, *J. Gen Virol.* 75:2873-2880 (1994)). Based on polymorphisms observed in the nt and aa sequences of N, P, M, F and M2 genes of 15 U.S. strains, a 89-94% nt sequence identity and 81-95% aa sequence identity (Shin et al., *J. Clin. Microbiol.* 40:1687-1693 (2002); Njenga et al., *Virus Res.* 91:163-169 (2003)) was found, indicating that these APV isolates are closely related. The above five genes from the U.S. viruses had 41-77% nt sequence identity and 52-78% aa sequence identity with European subgroups A or B viruses, thus suggesting that the APV-US viruses are genetically distinct from the European subgroups A or B and hence classified as subgroup C or APV/C (Shin et al., *J. Clin. Microbiol.* 40:1687-1693 (2002); Njenga et al., *Virus Res.* 91:163-169 (2003). This study reveals that the sequence of APV/CO SH protein shares a very low aa sequence identity with that of European subgroups A or B, thus supporting the classification of APV/CO into subgroup C. Similarly, comparative sequence similarity analysis of F gene from two APV strains isolated in France in 1985 showed low nt (56.6%) and aa (31.2%) sequence identity with APV/A, APV/B, and APV/C viruses, thus leading to the proposed existence of a forth, subgroup APV/D (Bayon-Auboyer et al., *Arch. Virol.* 144:1091-1109 (1999); Bayon-Auboyer et al., *J. Gen. Virol.* 81:2723-2733 (2000)).

Example 3

Sequence Analysis of the G Genes of APV-C Strains APV/CO, Mn-1a, and Mn-2a

The nucleotide and deduced amino acid sequences of the G genes of APV/CO, Mn-1a, and Mn-2a were determined using G mRNA as a template. All RT reactions of mRNAs isolated from virus-infected cells were performed using the Proto-Script first strand cDNA synthesis kit (New England Biolabs, Massachusetts). Three separate RT reactions were performed for each virus using an oligo dT primer (supplied with the kit) and two G gene-specific reverse primers, G-1589 (5' CAGT-GCCGTCCCCAAAACAT 3') (SEQ ID NO: 83) and G-1640 (5' CATCATAGCAACCAGC-CGGC 3') (SEQ ID NO: 84), which were designed based on the sequence obtained from viral genomic RNA. PCR was performed with TaKaRa LA Taq polymerase and GC buffer II (TaKaRa, Japan), and G-513 and G-1589 primers. The following cycle parameters were used in the PCR: initial denaturation at 94° C. for 1 m, 30 cycles of 94° C./30 s, 60° C./30 s and 72° C./2 m, and a final elongation step of 72° C. for 5 m. This yielded a single 1.1 kb PCR product. The entire RT-PCR was performed three times, each time with a new viral mRNA preparation, and each time a single RT-PCR product of 1.1 kb was amplified. The 1.1 kb RT-PCR product was either directly sequenced or was cloned and subsequently sequenced. The nucleotide sequencing procedures utilized BigDye terminator cycle-sequencing kit (Applied Biosystems) in the presence of 5% v/v DMSO or 1M (final concentration) of betaine in the sequencing reaction mixture. This sequence, along with the sequences at the 5' and 3' ends obtained from the RT reactions with genomic RNA, yielded the complete nucleotide sequence of the G gene.

The complete nucleotide sequence derived from RT-PCR of the viral genomic and mRNAs revealed that the G gene of APV/CO was 1798 nucleotides in length from gene-start to gene-end, and the major ORF was 1758 nucleotides (nt) long, encoding a polypeptide of 585 amino acids (aa). The gene length and the predicted protein length of G genes of Mn-1a and Mn-2a strains of APV-C were exactly the same as those of the APV/CO (Table 1).

TABLE 1

Features of G proteins of the metapneumoviruses

| Virus | Length of ORF (aa) | Molecular Weight (kDa) | G + C content | Percentage Proline | Serine + Threonine | No. of cysteine residues |
|---|---|---|---|---|---|---|
| APV/CO | 585 | 58.8 | 61.7 | 7.2 | 23.1 | 18 |
| APV-Mn1a | 585 | 58.3 | 62.9 | 7.2 | 22.2 | 18 |
| APV-Mn2a | 585 | 61.6 | 54.0 | 7.7 | 27.4 | 18 |
| APV-A | 391 | 43.0 | 48.5 | 6.7 | 23.5 | 20 |

TABLE 1-continued

Features of G proteins of the metapneumoviruses

| Virus | Length of ORF (aa) | Molecular Weight (kDa) | G + C content | Percentage Proline | Serine + Threonine | No. of cysteine residues |
|---|---|---|---|---|---|---|
| APV-B | 414 | 44.6 | 49.5 | 8.5 | 24.6 | 20 |
| APV-D | 389 | 41.8 | 49.7 | 9.5 | 23.9 | 20 |
| HMPV-00-1 | 236 | 25.8 | 47.0 | 8.5 | 33.9 | 1 |
| CAN97-83 | 219 | 23.7 | 46.4 | 7.8 | 32.0 | 1 |
| CAN98-75 | 236 | 25.5 | 46.6 | 5.5 | 33.9 | 2 |

The G gene of APV/CO possesses the gene-start signal 5' GGGACAAGU 3' (mRNA sense) (SEQ ID NO: 85). The gene-end signal 5' UAGUUAAUUAAAAA 3' (SEQ ID NO: 86) for the G gene of APV/CO was observed 13 nt downstream of the termination codon. Four potential secondary ORFs [ORF2—146-1771 nt (541 aa); ORF3—155-1771 nt (538 aa); ORF4—167-1771 nt (534 aa) and ORF5—1312-1608 nt (99 aa)] were observed in the G gene of APV/CO. ORFs 2, 3 and 4 possessed the exact carboxy-terminal as that of the major ORF. The signal peptide prediction also showed that a eukaryotic cleavage sequence was present between 46-47 aa residues. These observations denote that the polypeptides encoded from these secondary ORFs could probably be secreted forms of APV-C G protein. The G genes of APV-C strains Mn-1a and Mn-2a G also exhibited similar characteristics.

The predicted molecular mass of the G protein of APV/CO was 58,754 daltons, having a net charge of 8.27 at neutral pH and an isoelectric point of 8.28. The G+C residue content of the entire G gene of APV/CO was 61%. However, the G+C residue content of the G gene of Mn-2a was slightly lower (54%) than that of Mn-1a (62%) or APV-CO. Sequence alignment of the G genes of APV/CO and Mn-1a revealed 21 synonymous nucleotide substitutions (20 A→G and 1 C→T) across the length of the gene, resulting in 11 amino acid changes in the G protein of Mn-1a. On the other hand, the G gene of Mn-2a showed extensive sequence divergence from that of APV/CO and contained 195 nucleotide substitutions (190 synonymous and 5 non-synonymous), which ultimately resulted in 110 amino acid changes in the G protein of Mn-2a. The majority (60%) of these changes lay within amino acid 300 to 450 on the predicted protein, thus forming a highly-divergent domain on the G protein (FIG. 11).

The G protein of APV/CO contained 7.2% proline and 23.1% serine and threonine residues. The Mn-2a strain contained higher serine-threonine content (27.4%), while Mn-1a had values similar to APV-CO. The G ORF of APV/CO and Mn-2a contained five potential N-linked glycosylation sites; whereas, Mn1a contained four N-linked glycosylation sites (FIG. 11).

Hydropathy analysis of the G protein of APV/CO showed characteristics of an anchored type II membrane glycoprotein. The predicted hydrophobicity profile of APV/CO G protein included an amino-terminal intra-cellular domain (amino acids 1-31), followed by a hydrophobic TM domain (amino acids 32-54) and the extracellular domain (amino acids 55-585), consisting mainly of hydrophilic residues. Both Mn-1a and Mn-2a exhibited the same hydrophobicity profiles as that of APV/CO.

Though the G protein of APV/CO showed structural and biochemical features similar to those of the HMPVs, it showed only 21 to 25% amino acid identity with those of the HMPVs. However, the levels of amino acid identity with the G protein of other APVs were still lower, ranging only 14-16% (Table 2).

TABLE 2

Percent amino acid identity between the putative ORF's of APV-C and those of other metapneumoviruses.

| | N | P | M | F | M2 | SH | G | L |
|---|---|---|---|---|---|---|---|---|
| APV-A | 70 | 53 | 78 | 72 | 70 | 18 | 14 | 64 |
| APV-B | 70 | 52 | 77 | 71 | 65 | 13 | 14 | — |
| APV-D | — | — | — | — | — | — | 16 | — |
| HMPV-00-1 | 88 | 66 | 86 | 81 | 85 | 24 | 23 | 80 |
| CAN97-83 | 88 | 67 | 87 | 81 | 84 | 23 | 25 | 80 |
| CAN98-75 | 88 | 67 | 87 | 80 | 85 | 20 | 21 | 80 |

—: sequence not available

Among the U.S. strains, the G protein of APV/CO showed 98% and 81% amino acid identities with those of the strains Mn-1a and Mn-2a, respectively. The G proteins of strains Mn-1a and Mn-2a exhibited 79% amino acid identity between themselves. In addition, sequence comparison of the three membrane-associated glycoproteins (F, SH and G) of the three US APV strains revealed that the G protein is the most variable glycoprotein (Table 3).

TABLE 3

Percent amino acid identity between the membrane glycoproteins of the US isolates of APVs.

| | APV/CO vs Mn-1a | | APV/CO vs Mn-2a | | Mn-1a vs Mn-2a | |
|---|---|---|---|---|---|---|
| | nt | aa | nt | aa | nt | aa |
| F | 99.8 | 99.4 | 99 | 98 | 99 | 98 |
| SH | 100 | 100 | 99 | 98 | 99 | 98 |
| G | 99 | 98 | 87 | 81 | 86 | 79 |

Example 4

Sequence Analysis of the L Gene of APV/CO

Two different methods are used to determine the sequence of L gene. (a) RT-PCR of genomic RNA isolated from purified APV. APV is purified by the methods used for other paramyxoviruses. Briefly, Vero cells infected with APV/CO are harvested when maximum CPE is observed. The cells are scraped into the medium and lysed by several cycles of freezing and thawing. The cell lysates are centrifuged at 3000×g for 15 min to remove cell debris. Supernatants from infected cells are made 10% with respect to PEG 8000 and incubated for 3 hrs at 4° C. The virus is be pelleted by centrifugation at 4500×g for 30 min at 4° C. and resuspended in 1 mL of TNE buffer (50 mM Tris-HCl, 150 mM NaCl, 1 mM EDTA, pH 7.5). Genomic RNA is isolated from purified APV by TRIzol reagent (Invitrogen Corporation) according to the manufac turer's protocol, except that one additional extraction with chloroform is included.

The "genome-walking" strategy used for obtaining sequences of SH and G genes is employed to determine the sequence of L gene. Briefly, an mRNA-sense primer specific to the 5' region of the G gene is used to synthesize cDNA from the genomic RNA with a Thermoscipt RT kit (Invitrogen Corporation). The single-stranded cDNA is then purified using a nucleotide removal kit (Qiagen). A homopolymer (dc) tail is added to the 3' end of the purified cDNA using terminal deoxynucleotide transferase, and an aliquot is used in PCR-mediated amplification using the G gene-specific primer and Oligo(dG) anchor primer (Invitrogen Corporation). The amplified product is cloned into TA cloning vector (Invitrogen Corporation) and is used to transform DH10B cells. The resultant colonies are hybridized with a radioactively labeled DNA probe derived from the 3' end region of the G gene. Several positive clones containing large size inserts are sequenced. Sequences from several clones are compared to obtain the correct sequence. This process of genome walking is repeated to obtain the entire sequence of the L gene. In each round of genome walking, approximately 1 kb of new sequence is obtained; therefore, it will take four to five rounds of cDNA cloning to obtain the entire L gene sequence.

Determination of L Gene Sequence from mRNA

It is imperative that the L gene sequence obtained by genome walking be confirmed by sequencing the L mRNA. Vero cells are infected with APV/CO at a multiplicity of 1 PFU/cell. Total cellular is be isolated from cells at 24 h post-infection, using guanidinium thiocyanate and centrifugation through CsCl (Chirgwin et al., *Biochem.* 18:5294-5299 (1979)). Poly $(A)^+$RNA is isolated using Oligo-dT-cellulose chromatography (Aviv and Leder *PNAS* (*USA*) 69:1408-1412 (1972)). A cDNA library is constructed using Oligo-dT primer (Invitrogen Corporation). The library is screened by hybridization with a radioactively-labeled gene specific probe obtained by the RT-PCR of genomic RNA. Both strands of the L gene-specific inserts are sequenced.

TABLE 4

ATCC deposits of the following nucleic acid material were made:

| | Nucleotides Contained | ATCC Deposit Number |
|---|---|---|
| Clone Number | | |
| 1 | G > Forward to G < 615 | PTA-5668 |
| 2 | G > 538 to L < 713 | PTA-5669 |
| 3 | L > 703 to L < 2880 | PTA-5670 |
| 4 | L > 5007 to APV trailer | PTA-5671 |
| DNA Number | | |
| 1 | L > 2775 to L < 4000 | PTA-5672 |
| 2 | L > 3740 to L < 5650 | PTA-5673 |

As shown in Table 4 and in FIG. 10, APV clones 1-4 and DNA PCR products DNA 1 and DNA 2 are overlapping. Therefore, one can obtain the complete sequence of the L gene by utilizing the deposited nucleic acid material, ATCC Deposit Numbers PTA-5668, PTA-5669, PTA-5670, PTA-5671, PTA-5672, PTA-5673, the sequence information of which is fully incorporated by reference herein.

With the completion of the entire genomic sequence of APV-CO, the aa identity of each protein of APV/CO was compared with the corresponding proteins of other MPVs (Table 4). All eight proteins of APV/CO invariably showed higher levels of aa identity with the corresponding proteins of HMPVs than to those of the APVs. The N protein was the most identical protein between the HMPVs and APV/CO, while the M protein was the most identical among the APVs. The latter observation is consistent with the finding that antigenic cross-reactivity among APV-A, APV-B and APV-C occurs at the M protein and not the N protein (Lwamba et al., *Avian Dis.* 46: 725-729 (2002)). The M, M2, F and L proteins were the other proteins showing greater than 80% aa identity between APV-CO and the HMPVs. Among the membrane glycoproteins, F and SH proteins were more conserved within APV-C strains than the G protein.

TABLE 5

Comparison of the putative ORFs of APV/CO with other pneumoviruses.

| | Protein Length (aa) | | | | | | | | Complete Genome |
|---|---|---|---|---|---|---|---|---|---|
| Virus | N | P | M | F | M2 | SH | G | L | Length (nt) |
| APV-C | 394 | 294 | 254 | 537 | 184 | 175 | 585 | 2005 | 14150 |
| APV-A | 391 | 278 | 254 | 538 | 186 | 174 | 391 | 2004 | 13373 |
| APV-B | 391 | 279 | 254 | 538 | 186 | 175 | 414 | — | — |
| APV-D | — | — | — | — | — | — | 389 | — | — |
| HMPV-00-1 | 394 | 294 | 254 | 539 | 187 | 183 | 236 | 2005 | 13378† |
| CAN97-83 | 394 | 294 | 254 | 539 | 187 | 179 | 219 | 2005 | 13335 |
| CAN98-75 | 394 | 294 | 254 | 539 | 187 | 177 | 236 | 2005 | 13280 |
| RSV-A | 391 | 241 | 256 | 574 | 194 | 64 | 298 | 2165 | 15225 |
| RSV-B | 391 | 241 | 256 | 574 | 195 | 65 | 299 | 2166 | 15191 |
| BRSV | 391 | 241 | 256 | 574 | 186 | 81 | 257 | 2162 | 15140 |
| PVM | 393 | 295 | 257 | 537 | 176 | 92 | 396 | — | — |

—: Sequence not available

†Sequences at the termini are primer-based sequences

RSV: Respiratory syncytial virus;

BRSV: Bovine respiratory syncytial virus;

PVM: Pneumonia virus of mice

Example 5

Development of a Reverse Genetics System for Production of Infectious APV/CO from Cloned cDNA A cDNA that will transcribe the antigenomic (positive-strand) APV RNA in cells expressing the viral N, P, L and M2-1 proteins is constructed. Although synthesis of antigenomic RNA is not an absolute requirement, this approach has generally been used for recovery of negative-strand RNA viruses. The rationale for using the antigenomic RNA was that, unlike the genomic RNA, it would not be able to hybridize to the N, P, M2-1 and L mRNAs supplied to form RNP and initiate the first round of transcription.

A cDNA clone encoding the entire antigenome of APV/CO is constructed from cDNA fragments that are synthesized by RT-PCR from virion-derived genomic RNA (FIG. 8). Genomic RNA is extracted from purified APV/CO using TRIzol reagent according to the manufacturer's instructions (Invitrogen Corporation). RT is carried out using Superscript II RT (Invitrogen) and PCR is accomplished using proofreading Pfu DNA polymerase (Stratagene). The number of PCR cycles is limited to twenty to further minimize misincorporation of nucleotides. The leader end is constructed to join the promoter for T7 RNA polymerase that includes three transcribed G residues for optimal activity. The presence of these non-viral G residues has been shown not to interfere with the rescue of other paramyxoviruses (Collins et al., *PNAS (USA)* 92:11563-11567 (1995); and Whelan et al., *PNAS (USA)* 92:8388-8392 (1995)). To generate a nearly exact 3' end, the trailer end is constructed to join hepatitis delta virus (HDV) antigenome ribosome sequence followed by tandem terminators of T7 transcription (Pringle, *Arch. Virol.* 143:203-210 (1998)).

pBR322 is used as the plasmid vector to assemble APV cDNA fragments since large-size inserts are more stable in this low copy number plasmid. Analysis of the complete genome sequence of APV/CO will identify unique restriction sites that are present in the APV genome but are absent in the pBR322 vector. Some of these restriction sites are chosen to assemble the cDNA fragments. Although the APV minigenome has been shown not to obey the "rule of six" (Randhawa et al., *J. Virol.* 71:9849-9854 (1997)), the exact number of nucleotides present in the genome of APV/CO is maintained in the full-length cDNA. Two unique restriction site markers are introduced into M-F and F-M2 intergenic regions of the antigenomic cDNA by incorporating changes into oligonucleotide primers used in RT-PCR. This facilitates assembly and are used as sequence markers to identify the recombinant virus.

Initially, each cDNA fragment is cloned separately and the correct sequence is confirmed by DNA sequencing. All the APV cDNA fragments are then ligated successively to form the full-length APV cDNA. If a cDNA fragment is found to contain misincorporation of nucleotide(s), it is recloned and resequenced. Alternatively, smaller fragments are joined using other unique restriction sites. DH10B cells (Invitrogen Corporation) are used to carry the full-length APV cDNA clone. These cells cause minimum rearrangement of large size plasmids. Also, the cells are grown at 30° C. to further reduce rearrangement.

Cloning of the cDNA fragments bearing the open reading frames of N, P, and M2-1 genes in pTM-1 plasmid is discussed below. The remaining L gene cDNA fragment is cloned into pTM-1 vector. The cloned gene is sequenced to entirety. The Vero cells are used for transfection experiments because these cells are highly permissive for APV and vaccinia virus. In addition, these cells can be transfected efficiently by Lipofectamine method (Invitrogenv Corporation). The cells are transfected under the transfection conditions that were used to rescue infectious human and bovine respiratory syncytial viruses (Collins et al., *PNAS (USA)* 92:11563-11567 (1995), Yunus et al., *Virus Genes* 23:157-164 (2001)).

Briefly, confluent monolayers of Vero cells in six-well dishes are infected with 1 focus-forming unit per cell of recombinant vaccinia virus strain MVA that expresses T7 RNA polymerase (MVA-T7). The MVA strain is a host-range mutant that grows permissively in avian cell; whereas, in mammalian cells, the virus expresses T7 RNA polymerase, but there is no production of infectious virus due to a block at a later stage in virion maturation (Pringle, *Arch. Virol.* 143:1449-1459 (1998)). A mixture of four plasmids containing the APV N, P, L, and M2 (ORFI) under the control of the T7 promoter (0.4. 0.3, 0.2, and 0.1*g per well, respectively) and a fifth plasmid [p(+)APV] encoding the full-length APV antigenome (1*g) are transfected with Lipofectamine as recommended by the supplier (Invitrogen Corporation). Cells are incubated in a $CO_2$-incubator at 32° C. Twelve hours later, the medium is replaced with optiMEM medium (Invitrogen Corporation) containing 2% bovine fetal serum and 40*g of cytosine arabinoside per ml to inhibit the replication of vaccinia virus. After 3 days, clarified medium supernatants are passaged onto fresh Vero cells and overlaid with methylcellulose for staining with antiserum to APV by horseradish peroxidase method (36) or 1% agarose for plaque isolation. Control transfections include cells that received the support plasmids but no p(+)APV and cells that received p(+)APV, but no support plasmids. Different transfection methods are tested to achieve the highest level of APV recovery. Several APV-like plaques are picked from plates that have been overlaid with metylcellulose. Each plaque is further purified by two plaque-to-plaque isolations. Stocks of each plaque isolate are made in Vero cells for characterization. A schematic of the transfection procedure is shown in FIG. 8.

First, is ascertained that the recovered virus is APV. A plaque neutralization test is performed using hyperimmune serum against wild-type APV/CO. Methyl cellulose overlay and neutral red staining is used in the plaque assay. Wild-type APV/CO is used as a positive control and wild-type vaccinia virus is used as a negative control. The size of the plaques derived from recovered APV is compared with those of the wild-type APV/CO.

To verify that the two sequence markers inserted into the full-length cDNA are present in the recovered APV, reverse transcription of genomic RNA purified from wild-type and recombinant APV, using primers from upstream of each restriction site, is carried out. The reverse transcription products are amplified by PCR using an additional primer downstream of each restriction site. The presence of the sequence marker in the recombinant virus is verified by digestion of the PCR products with appropriate restriction enzymes. The PCR products representing the recombinant APV contain the expected restriction sites, while those representing the wild-type APV do not contain the restriction sites. To further confirm the sequence markers, the PCR products are cloned and sequenced. This confirms that the recovered APV was produced from cDNA clones and was not a laboratory contamination of wild-type APV/CO.

The replication behavior of the recovered APV is compared to that of the wild-type APV/CO. Briefly, Vero cell monolayers in 25-$cm^2$ culture flasks are infected with 2 PFU either virus per cell. One flask every 12 hours is transferred to −70° C. The samples are subsequently thawed and titrated in parallel by plaque assay. Only 2 PFU of APV per cell are used because APV does not grow to high titer. This will indicate any differences in the replication behavior between the recombinant and wild-type APV.

Example 6

Construction of Expression Plasmids cDNA fragments bearing the open reading frames of N, P and M2-1 genes were generated by RT-PCR from APV/CO genomic RNA using primers based on published nucleotide sequence of these genes. The cDNA fragment were cloned in an expression plasmid (pT<−1) which has an encephalomyocarditis virus (EMCV) internal ribosome entry site (IRES) downstream of the T7 RNA polymerase promoter and makes use of the translation start codon contained in Nco I site of IRES. The cloned genes were sequenced to their entirely and were found to be correct. Correct expression also has been obtained for these genes using TNT T7 coupled reticulocyte lysate system (Promega).

Example 7

Generation of Recombinant APV with Mutations in the Fusion Protein Cleavage Site and Evaluation of the Pathogenecity of Mutant APV in Turkeys The amino acid sequence at the F protein cleavage site has been thought to be a major determinant of paramyxovirus virulence (Nagai et al., *Virol.* 72:494-508 (1976)). Cleavage of the precursor protein $F_0$ to $F_1$ and $F_2$ by host cell proteases is required for progeny viruses to become infective (Collins et al., in *Fields Virology*, Fields et al., eds., Lippincott-Raven, Philadelphia, Pa., pp. 1205-1241 (1996)). In closely-related NDV, the virulent strains have multibasic residues Arg-Gln-Lys-Arg (SEQ ID NO:19) at the cleavage site, which are substrates for proteases found in most tissues. The $F_0$ protein of antivirulent NDV strains has dibasic residues Arg-Gln-Gly-Arg (SEQ ID NO:20) at the cleavage site, which are cleaved by proteases found only in the respiratory tract. Therefore, the avirulent NDV strains replicate only in the respiratory tract and do not spread to other tissues. The APV US isolates have an F protein cleavage site sequence of Arg-Lys-Ala-Arg (SEQ ID NO:21), which is similar to the multibasic residues found at the cleavage site of virulent NDV strains. Therefore, one can mutate the F protein cleavage site sequence of APV/CO to Arg-Gln-Gly-Arg (SEQ ID NO:20), which are present at the F protein cleavage sites of avirulent NDV strains LaSota and B1. This particular mutant APV may replicate only in limited tissues and not cause disease in turkeys.

Mutations are introduced into APV F gene cDNA fragments separately and then assembled into the full-length cDNA. The two unique restriction sites introduced in M-F and F-M2 intergenic regions will be used to replace the wild-type F gene fragment with an F gene fragment that contains mutations at the cleavage site. The F protein cleavage site mutant will be generated by sequential PCR mutagenesis (Byrappa et al., *Genome Res.* 5:404-407 (1995)). All PCR amplifications are carried out using proofreading Pfu DNA polymerase. The mutated fragment is sequenced in its entirety to confirm that the correct mutations were present. The wild-type gene fragment in the full-length cDNA clone is then replaced with the mutated F gene fragment and sequenced again to reconfirm the mutations in the full-length cDNA. The strategy for construction is shown in FIG. 8.

Recovery of the mutant APV strains is carried out as described above. Recovered viruses are biologically cloned by plaque purification before amplification and analysis. If a problem should arise in recovery of the mutant virus due to inefficient cleavage of the F protein, then acetylated trypsin (0.01 mg/ml) is added to the medium to facilitate growth. If necessary, trypsin is also added to the overlay medium in the plaque assay. To confirm the presence of the mutation in the genome of the recovered virus, the region of the F protein containing the cleavage site is amplified by RT-PCR, cloned into TA cloning vector and sequenced. The stability of the mutations is also examined after several passages (at least 15 passages).

To compare the viral proteins synthesized by the wild-type and mutant viruses, Vero cells are infected with a multiplicity of infection of 2 PFU and labeled by incubation with [$^{35}$S] methionine from 12 to 15 hours post infection. APV-specific proteins are immunoprecipitated from infected cell lysates using polyclonal APV antiserum. Total and immunoprecipitated proteins are analyzed by SDS-PAGE. The uncleaved FO (68,000 Da) and the cleaved FI (53,000 Da) and F (1 5,000 Da) forms of the fusion protein of wild-type and mutant viruses are analyzed. If necessary, the F proteins are also characterized by Western blot analysis.

To study the pathogenicity and persistence of APV, sixty 2-week-old turkey poults are allotted equally to four groups. Each bird in Group I is inoculated with 0.2 ml of $10^5$ TCID$^{50}$ of APV/CO wild-type virus through the oculonasal route. The birds in Groups II and III are inoculated with the same amount of virus via the oculonasal route, with recombinant APV and "F" cleavage site mutant APV respectively. Birds in Group IV are kept as uninfected controls. Three poults from each group are euthanized at 1, 7, 14, 21 and 28 days post-inoculation (PI). The birds are observed daily for clinical signs. A score of 0-6 is used to describe the clinical signs (Cook et al., *Avian Pathol.* 18:511-522 (1989)) as follows: 0=no clinical signs, 1=unilateral nasal discharge, 2=bilateral nasal discharge, 3=unilateral watery eyes, 4=bilateral watery eyes, 5=moderate sinus swelling, 6=severe sinus swelling. Swabs and sections from sinuses, harderian glands, trachea and lungs are collected at necropsy for virus isolation and viral RNA detection. Blood is collected from euthanized poults on days 14, 21 and 28 PI for serologic examination.

To study the tissue distribution of wild-type, recombinant and mutant APV in turkey poults, sixty 2-week-old turkey poults are allotted to four groups equally. Each bird in Groups I to III are inoculated with 0.2 ml of $10^5$ TCID$_{50}$ of the respective APV strains (APV wild-type, recombinant APV and mutant APV). Birds in Group IV are kept as uninfected controls. Three poults are euthanized at 3, 5, 7, 14 and 21 days PI. Sections from sinuses, harderian glands, trachea, lungs, thymus, bursae, liver, spleen, ileum, jejunum, brain and bone marrow are collected for virus isolation, viral RNA detection and histopathology. Blood is collected from euthanized birds at 3, 5, 7, 14 and 21 days PI for serologic examination.

Virus isolation is attempted from 1:10 diluted sample supernatants in 9- to 11-day-old chicken embryos inoculated via the allantoic route (Cook, *Rev. Sci. Tech. Off. Int. Epiz* 19:602-612 (2000)). For viral RNA detection, the total viral RNA is extracted from the samples using TRIzol (Invitrogon) reagent, and RT-PCR is conducted using primers specific for the M gene of APV. For serologic estimation of APV antibodies, an indirect ELISA employing homologous, purified APV viruses and virus neutralization tests in Vero cells is performed, essentially as described earlier by O'Loan et al., *J. Virol. Meth.* 25:271-282 (1989). For histological evaluation of the tissues, the sections from sinuses and tissues are fixed in 10% neutral buffered formaldehyde, processed through graded alcohols, and embedded in paraffin. Four to five micrometer thick sections are out and stained by hematoxylin and eosin before analyzing the histological changes.

It will be clear that the invention may be practiced otherwise than as particularly described in the foregoing description and examples.

Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

What is claimed is:

1. A live-attenuated avian pneumovirus containing one or more attenuating mutations in the F protein cleavage site, wherein the sequence of the mutated F protein cleavage site is Arg-Gln-Gly-Arg (SEQ ID NO:20).

2. The avian pneumovirus of claim 1 wherein the avian pneumovirus is strain Colorado (AVP/CO).

\* \* \* \* \*